United States Patent
Ou-Yang

(10) Patent No.: US 6,636,037 B1
(45) Date of Patent: Oct. 21, 2003

(54) SUPER SENSITIVE EDDY-CURRENT ELECTROMAGNETIC PROBE SYSTEM AND METHOD FOR INSPECTING ANOMALIES IN CONDUCTING PLATES

(75) Inventor: Tian-He Ou-Yang, Ames, IA (US)

(73) Assignee: Innovative Materials Testing Technologies, Ames, IA (US)

( * ) Notice: Subject to any disclaimer, the term of this patent is extended or adjusted under 35 U.S.C. 154(b) by 0 days.

(21) Appl. No.: 09/540,370

(22) Filed: Mar. 31, 2000

(51) Int. Cl.[7] .............................................. G01N 27/82
(52) U.S. Cl. ...................... 324/240; 324/232; 324/234
(58) Field of Search .................................. 324/240, 239, 324/229, 228, 232, 236, 237, 238, 242, 243, 217, 235, 262, 233, 234; 174/35 R, 35 CE

(56) References Cited

U.S. PATENT DOCUMENTS

| | | | | |
|---|---|---|---|---|
| 3,996,510 A | * | 12/1976 | Guichard | 324/236 |
| 5,414,356 A | * | 5/1995 | Yoshimura et al. | 324/239 |
| 5,572,120 A | * | 11/1996 | Takaishi et al. | 324/207.21 |
| 5,955,954 A | * | 9/1999 | Keller | 324/260 |
| 6,002,251 A | * | 12/1999 | Sun | 324/240 |

* cited by examiner

*Primary Examiner*—Jay Patidar
(74) *Attorney, Agent, or Firm*—Schwegman, Lundberg, Woessner & Kluth, P.A.

(57) ABSTRACT

Devices and methods for improved inspections of conducting structures of different shapes. An eddy-current probe includes an excitation coil unit, a magnetic detector within the probe, a signal-conditioning/preamplifier circuit within the probe, and a signal channel. The excitation coil unit is shielded on substantially all sides except an emission face that transmits an alternating magnetic signal to a conducting (e.g., metal) object, such that the metal object modifies the alternating magnetic signal. The magnetic detector within the probe is also shielded on substantially all sides except a reception face, such that the alternating magnetic signal as modified by the metal object is received into the shielded magnetic detector and converted into a first electrical signal. The signal-conditioning/preamplifier circuit within the probe is shielded on substantially all sides and provided with electrical power. The shielded preamplifier provides detection for very small signals, such as from magnetic probing of aircraft skin metals. Other embodiments include a traveling-wave excitation structure and a multiple-phase driving circuit, some of which include the shielded preamplifier, and others of which are not shielded. An eddy scope is described that provides a multiple-phase excitation signal to various different probes.

34 Claims, 37 Drawing Sheets

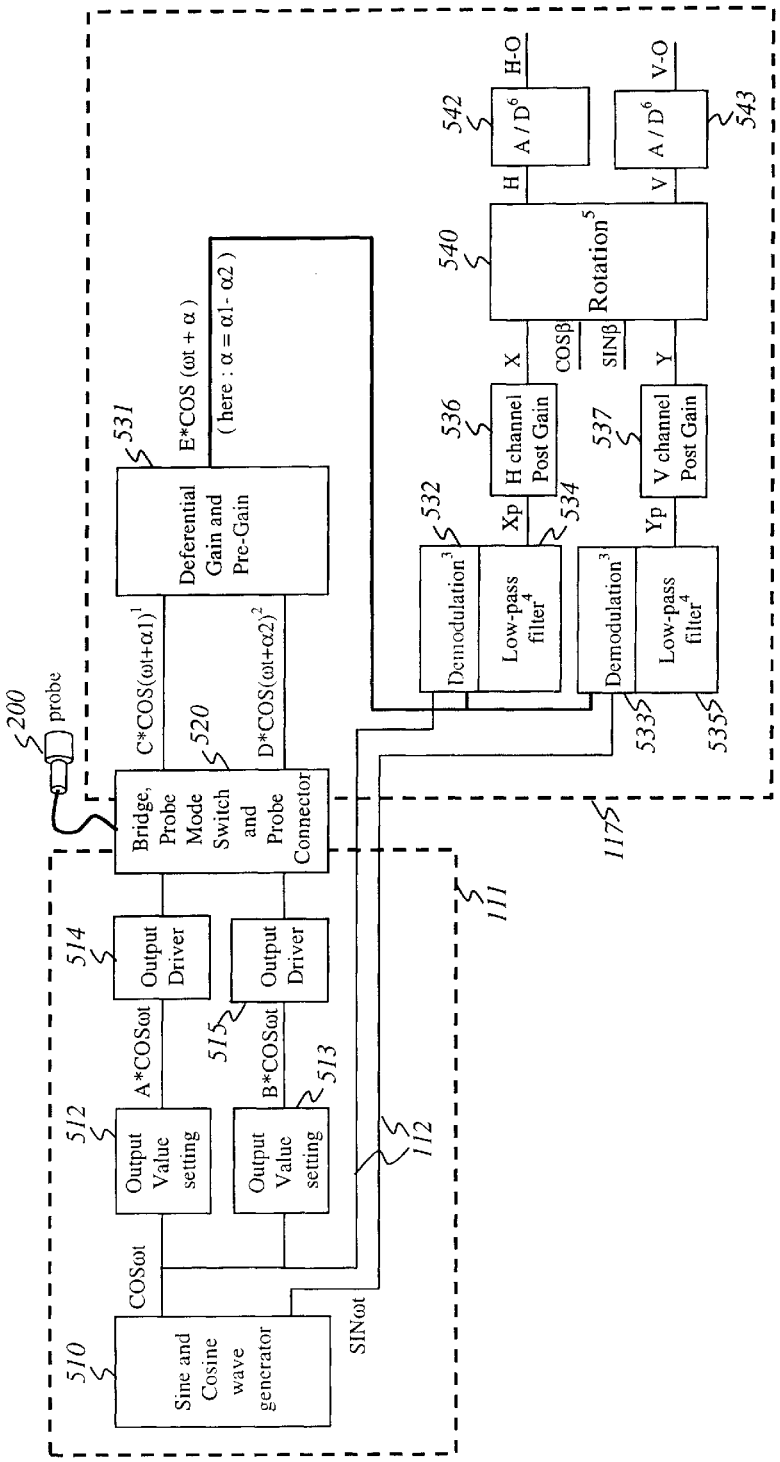

FIG. 1B

1. C/A & α1: magnitude and phase changes in testing channel due to probe condition.
2. D/B & α2: magnitude and phase changes in reference channel due to probe condition.
3. After Demodulation: $Xm = COSωt * E*COS(ωt+α) = 1/2 E*[COS(2ωt+α) + COSα]$
   $Ym = COSωt * E*SIN(ωt+α) = 1/2 E*[SIN(2ωt+α) + SINα]$
4. After low-pass filter: $Xp = 1/2 E * COSα$
   $Yp = 1/2 E * SINα$
5. After Rotation: $H = X * COSβ - Y * SINβ$
   $V = Y * COSβ + X * SINβ$
6. After A/D: H-O are H-Channel digital data output, or real component of the output
   V-O are V-Channel digital data output, or imaginary component of the output

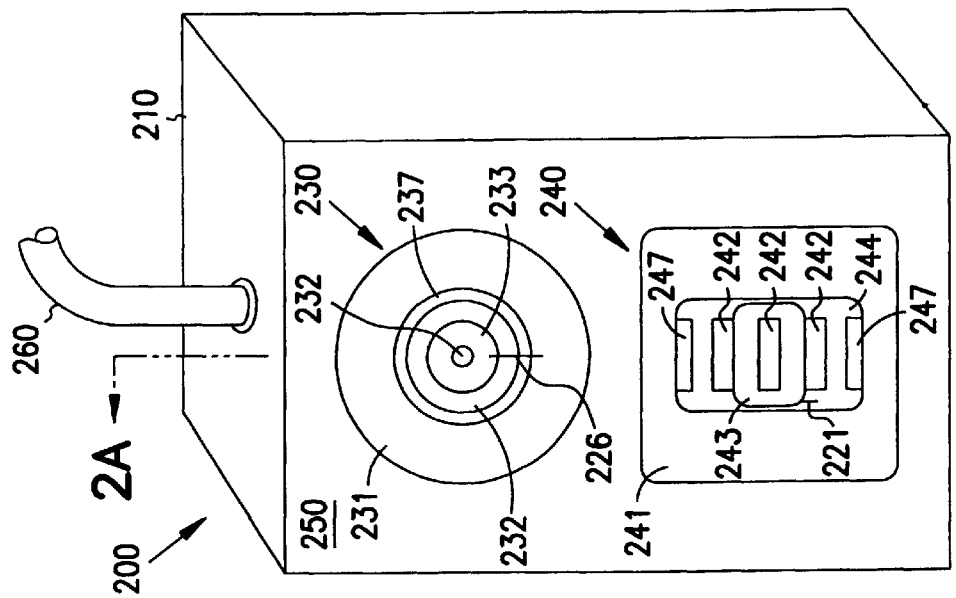
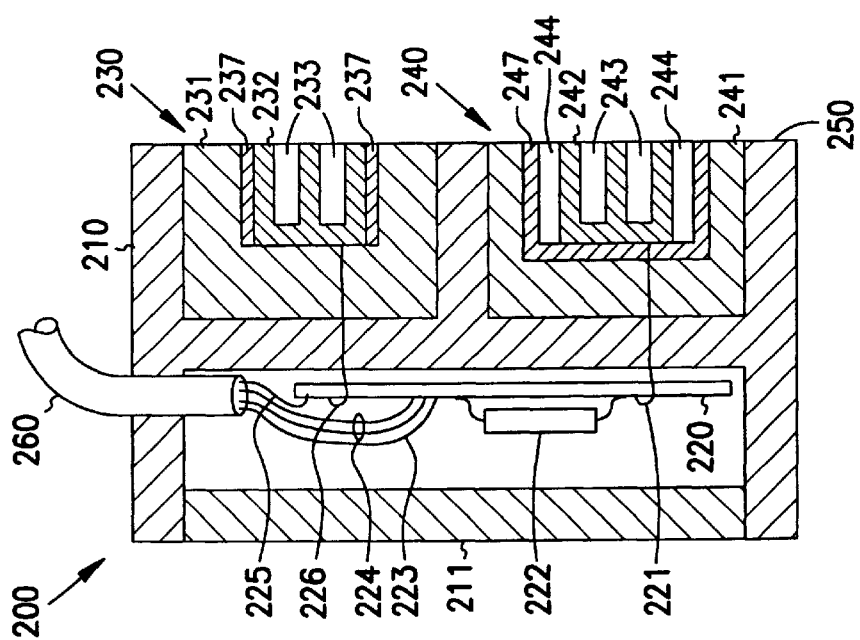

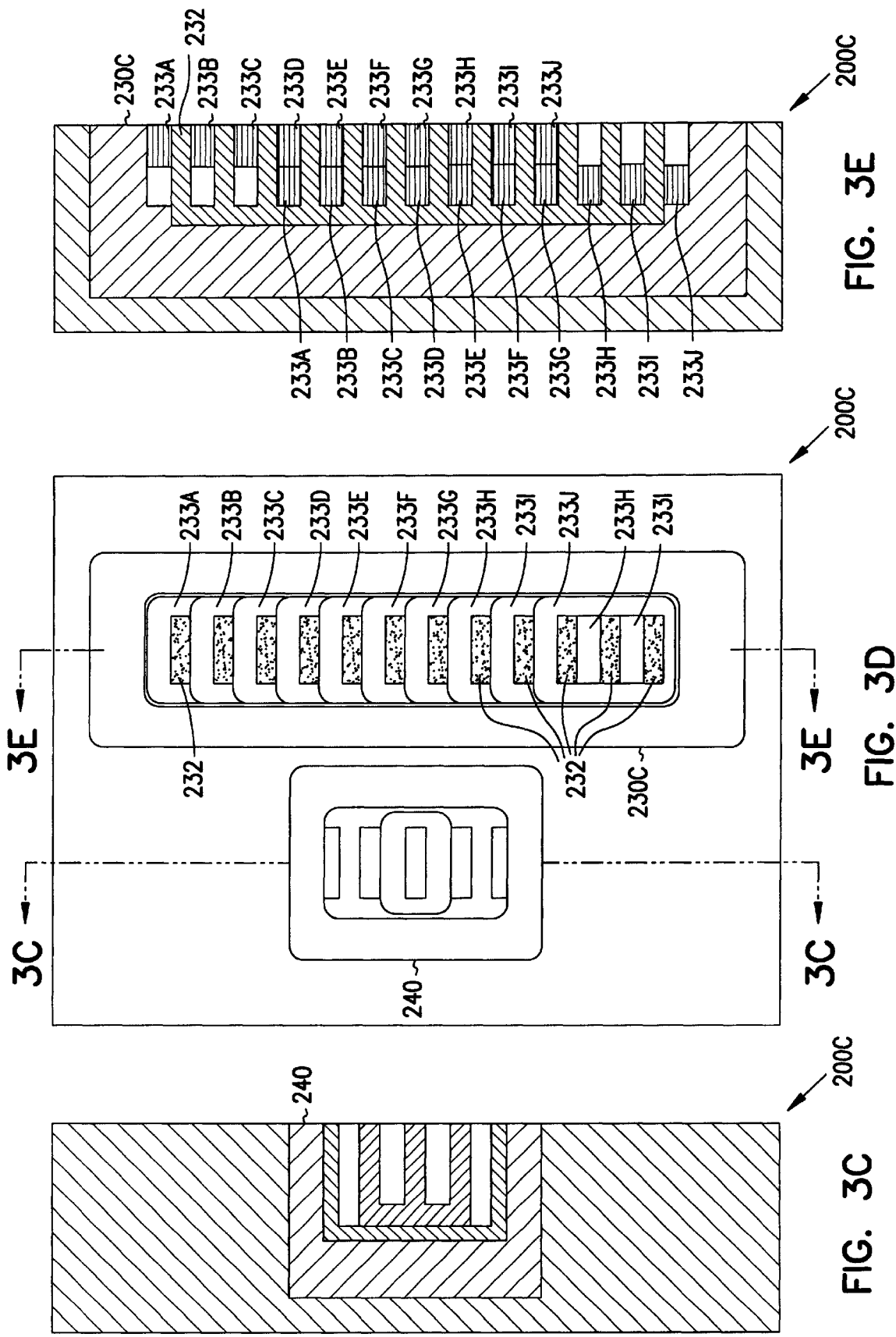

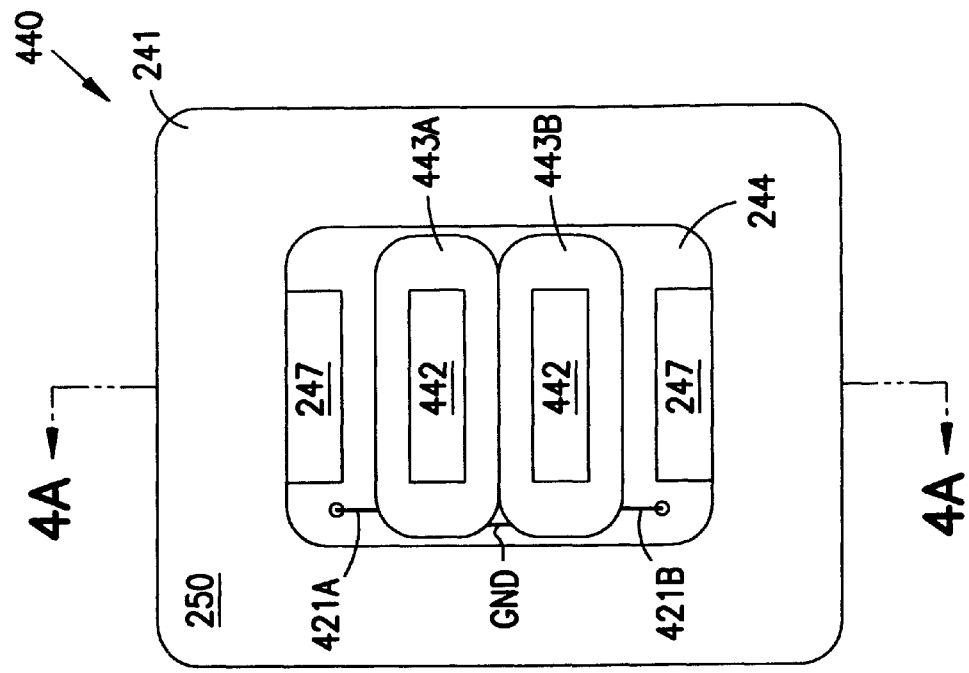
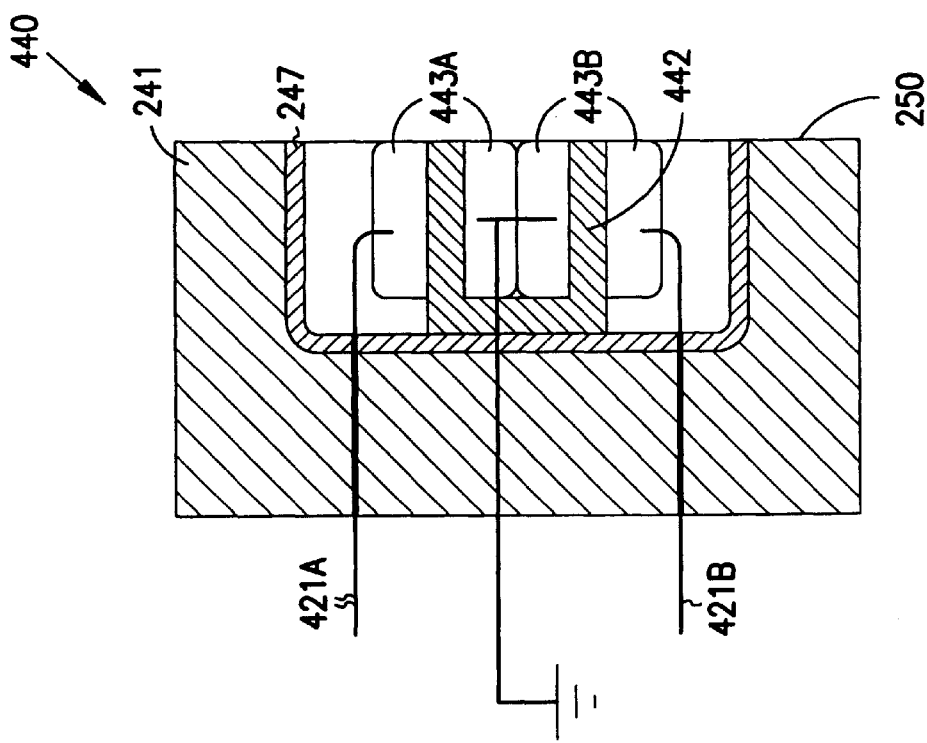
FIG. 4B
FIG. 4A

Scanning on a 0.33"
clear aluminum plate

Scanning on a 0.33"
aluminum plate
with a discontinuity
below

Adding a 0.182"
thick plate to make
total thickness to be
0.51"

10% thinning on
bottom of the
0.063" thick
Specimen #5**

FIG. 6D DEMO #2-1 - Detecting 10% Corrosion Thinning on Specimen #5

Add a 0.09" thick plate
Total thickness 0.153"
Relative thinning
is 4%

FIG. 6E DEMO #2-2 - Detecting 4% Corrosion Thinning on Specimen #5

Thicker top plate,
Total thickness 0.245"
Relative thinning
is 2.45%

FIG. 6F DEMO #2-3 - Detecting 2.45% Corrosion Thinning on Specimen #5

-13.17% thinning on the bottom of the 0.063" thick Specimen #1

FIG. 7D   DEMO #3-1 - Detecting 3.17% Corrosion Thinning on Specimen #1

Total thickness is 0.153"
Relative thinning is 1.33%

Total thickness is 0.245"
Relative thinning
is 0.8%

FIG. 7F  DEMO #3-3 - Detecting 0.82% Corrosion Thinning on Specimen #1

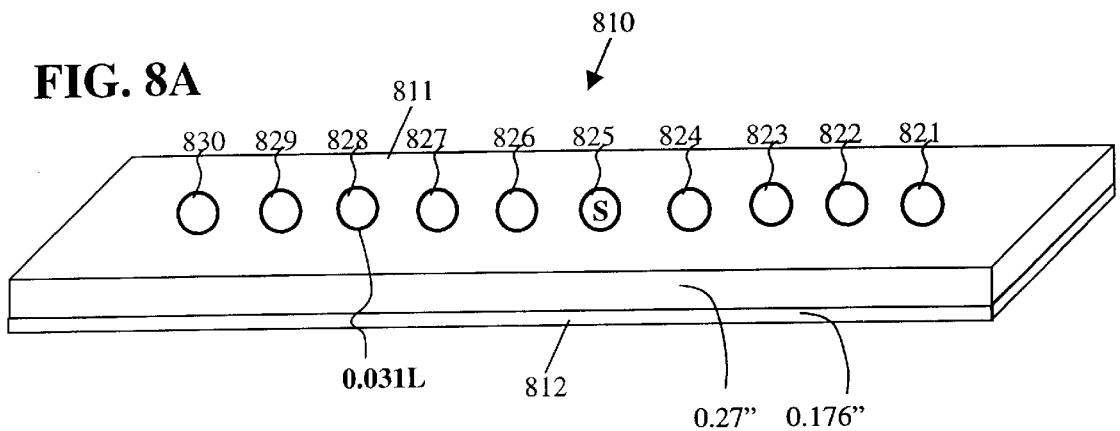
FIG. 8A
Lockheed Georgia Specimen #B4-1:
Total thickness - 0.446"
Ten fasteners: nine titanium + one steel.
A 0.031" long fatigue crack on fastener hole #8 on the bottom surface of the lower layer, or 0.446" below the surface of inspection
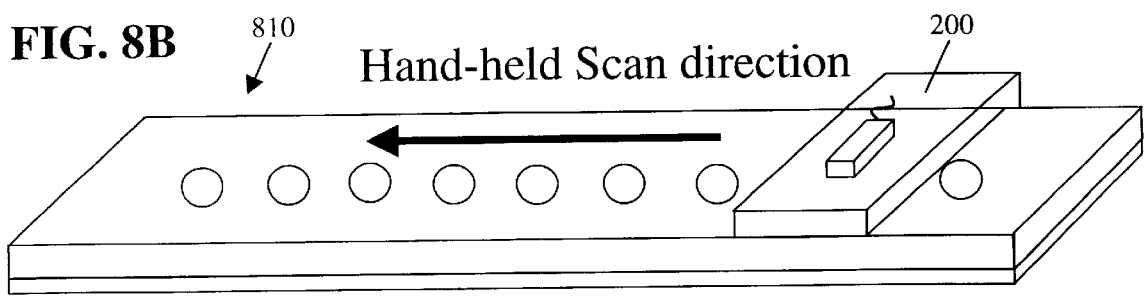
FIG. 8B Hand-held Scan direction

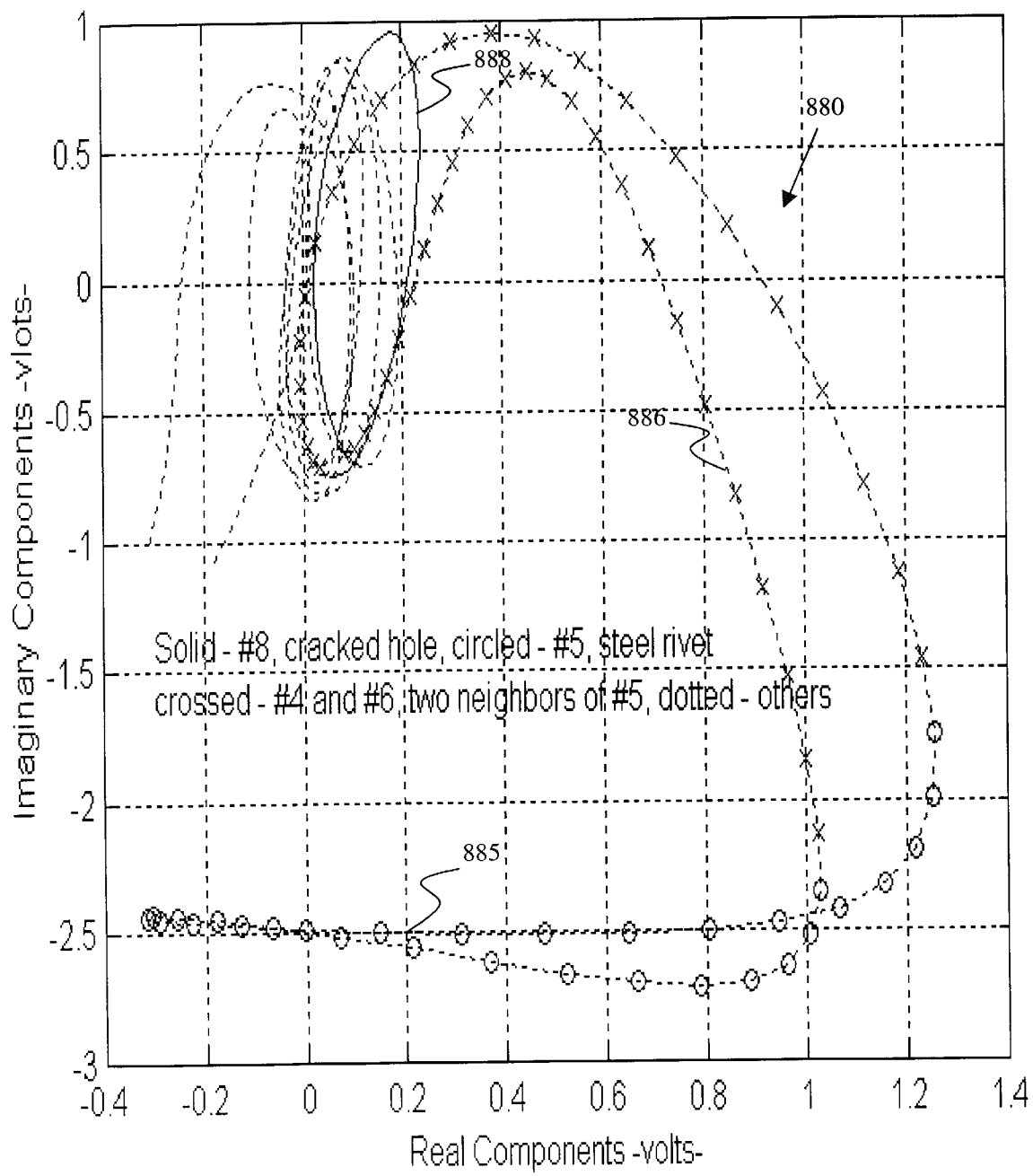

Crack length = 0.148"

Four-Phase Power Output

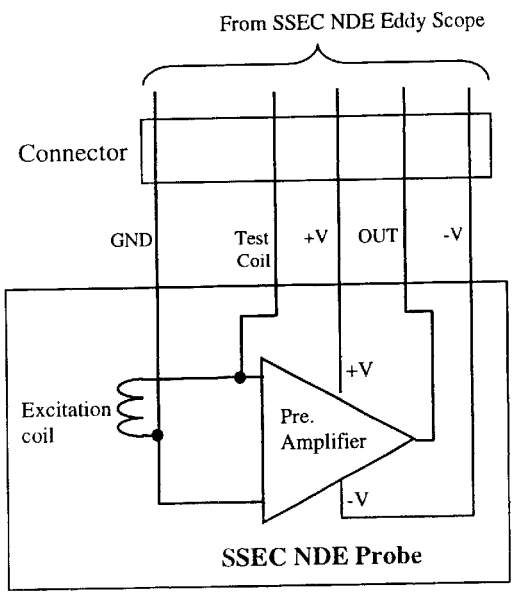
FIG 11A  Absolute probe 1100A with one excitation coil
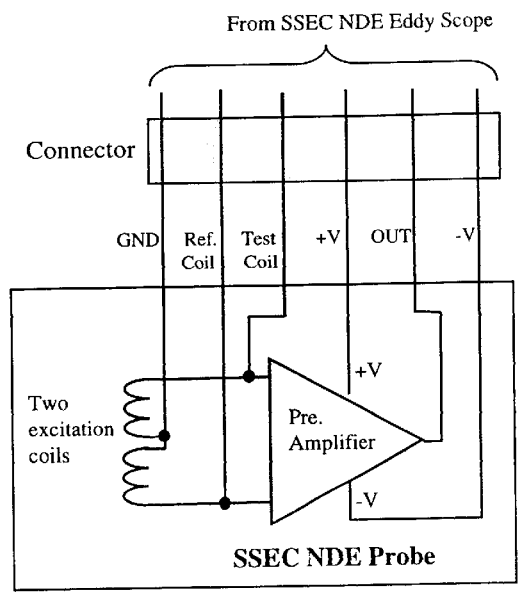
FIG 11B  Differential probe 1100B with two excitation coils
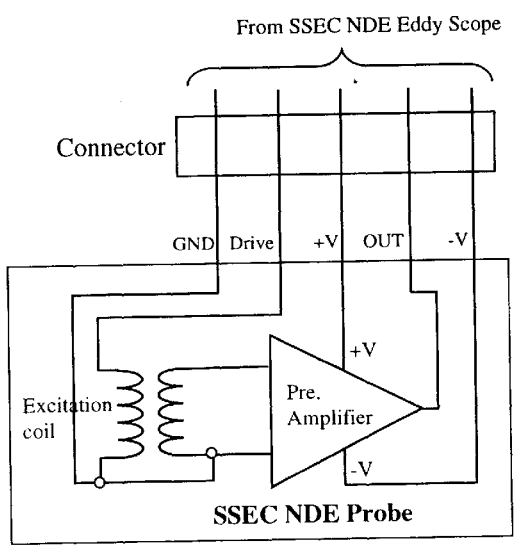
FIG. 11C  Reflection-absolute probe 1100C with one excitation coil and one pickup coil
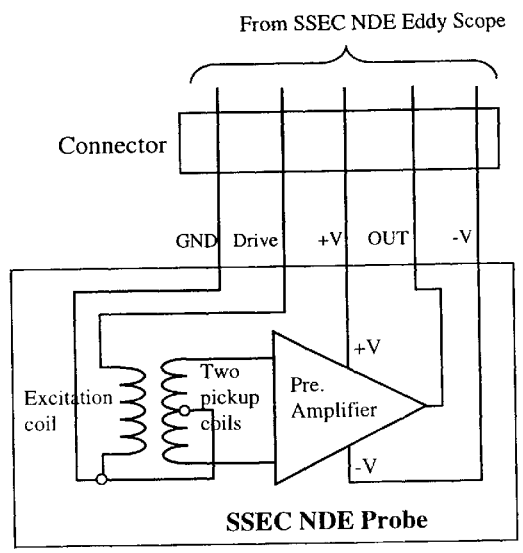
FIG. 11D  Reflection-differential probe 1100D with one excitation coil and two pickup coils

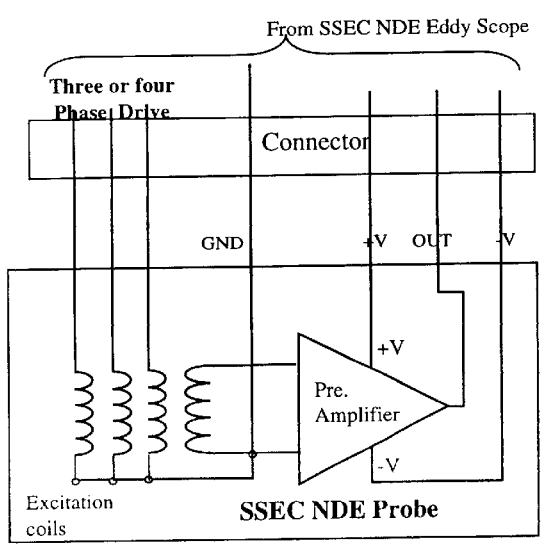
FIG. 11E Rotating-magnetic-field probe 1100E with one absolute pickup coil
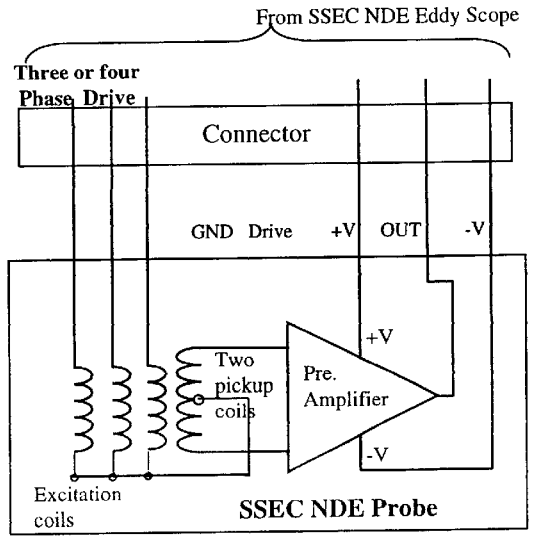
FIG. 11F Rotating-magnetic-field probe 1100F with a pair of differential pickup coils
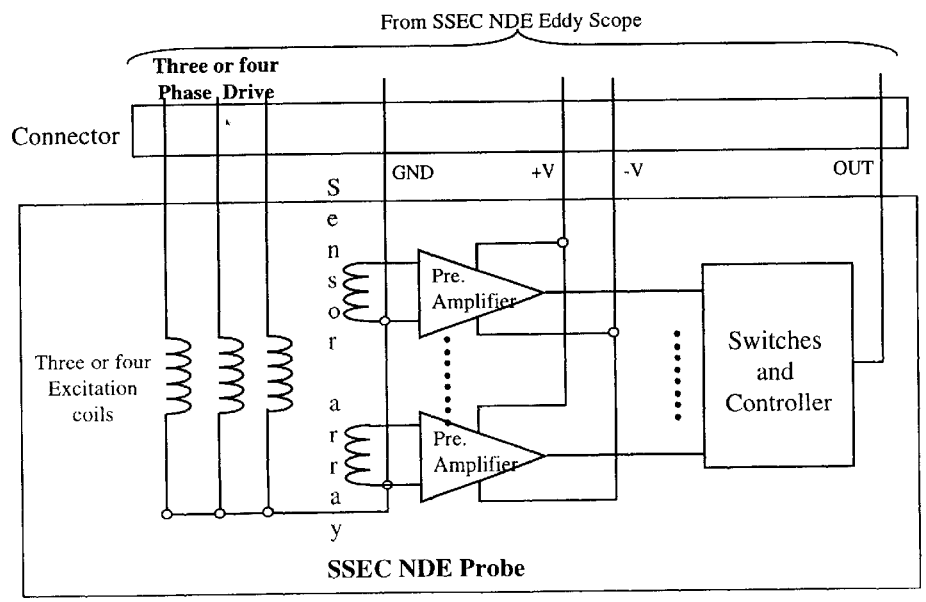
FIG. 11G Rotating-magnetic-field probe 1100G with a sensor array of absolute pickup coils

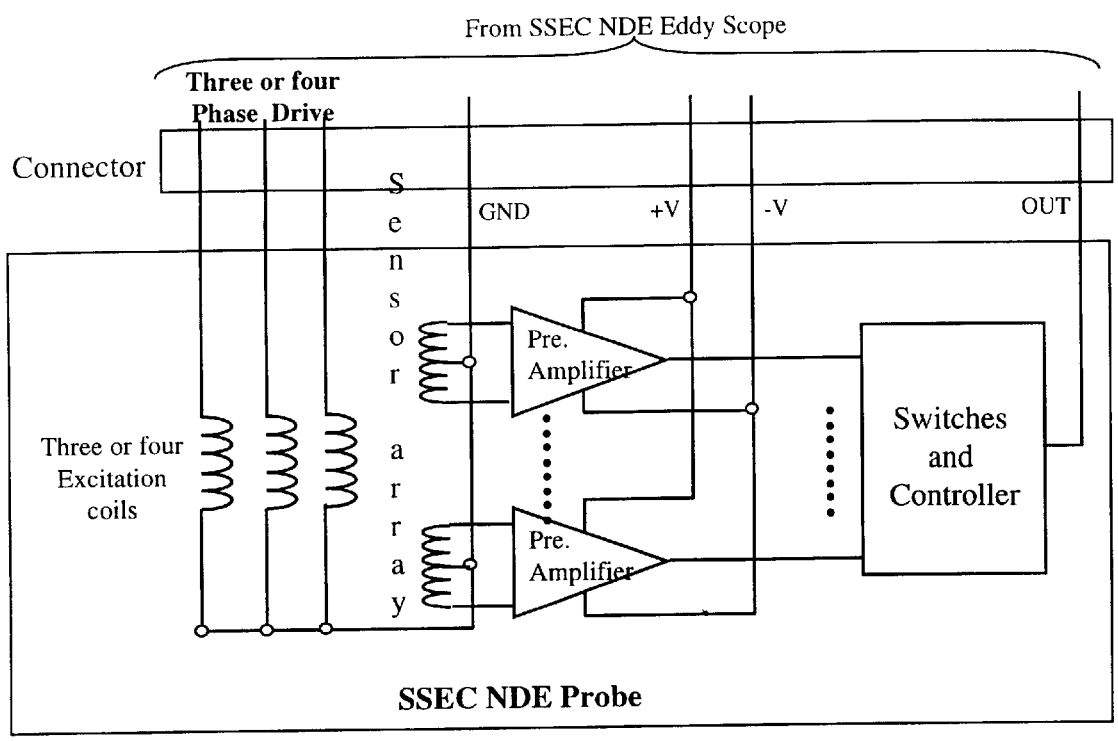
FIG. 11H Rotating-magnetic-field probe 1100H with a sensor array of differential pickup coils

SUPER SENSITIVE EDDY-CURRENT ELECTROMAGNETIC PROBE SYSTEM AND METHOD FOR INSPECTING ANOMALIES IN CONDUCTING PLATES

FIELD OF THE INVENTION

This invention relates to the field of non-destructive magnetic probe testing and more particularly to an eddy-current probe and methods for using it for non-destructive testing of metallic objects, for example plates, and in particular, for example, aluminum aircraft skin.

BACKGROUND OF THE INVENTION

The need and demand for inspection of metallic plates in an aging infrastructure has been increasing within the last decade due to an increase in both public awareness and concern for the environment. The non-destructive evaluation ("NDE") techniques currently in use do not meet all the requirements for such inspections. Recent market research indicates that there is a call for better inspection techniques.

One NDE technique is described in U.S. Pat. No. 6,002,251, which issued Dec. 14, 1999 to Yushi Sun, entitled "ELECTROMAGNETIC-FIELD-FOCUSING REMOTE-FIELD EDDY-CURRENT PROBE SYSTEM AND METHOD FOR INSPECTING ANOMALIES IN CONDUCTING PLATES," which is incorporated herein by reference. Dr. Sun's patent describes a remote-field eddy-current (RFEC) inspection technique and apparatus. The probes described do not provide amplification in the probe.

Magnetic fields create eddy currents within metallic objects in their path. The eddy currents in turn affect the magnetic field. Cracks, discontinuities, holes, and changes in the material content all affect the eddy current flow within the object, and thus the magnetic field external to the object. Remote-field eddy-current techniques generally involve detecting magnetic-field changes remote from the excitation source (often, wherein the magnetic field passes twice through the object), while near-field eddy-current techniques generally involve detecting magnetic-field changes next to the excitation source.

Users desire probes and techniques that are fast, reliable, accurate, easy to operate, and inexpensive. There is a need to extend the RFEC technique, as well as other eddy-current techniques for better noise control and small-flaw detection for inspection of various objects with different geometries, for example, those with flat geometry, or with approximately flat geometry in at least a local area, as well as objects with other surface geometries.

SUMMARY OF THE INVENTION

The present invention provides devices and methods for improved inspections of conducting objects, such as flat-shaped conducting structures, as well as conducting structures having other different shapes.

One aspect of the present invention provides a method of transducing magnetic signals indicative of a flaw in a metal object. This method includes shielding an excitation coil on substantially all sides except an emission face, transmitting an alternating magnetic signal to the metal object from the shielded excitation coil, such that the alternating magnetic signal is modified by the metal object, shielding a magnetic detector within a probe on substantially all sides except a reception face. The method also includes receiving the alternating magnetic signal as modified by the metal object into the shielded magnetic detector, converting the received alternating magnetic signal into a first electrical signal within the shielded magnetic detector, shielding a signal-conditioning circuit within the probe on substantially all sides, providing electrical power to the shielded signal-conditioning circuit within the probe, amplifying the first electrical signal with the signal-conditioning circuit to create a second electrical signal, and analyzing phase and amplitude components of the second electrical signal to provide an indication of the flaw.

Another aspect of the present invention provides an eddy-current probe system for detecting a flaw in a metal object. The probe includes an excitation coil unit, a magnetic detector within the probe, a signal-conditioning circuit within the probe, and a signal channel. The excitation coil unit is shielded on substantially all sides except an emission face that transmits an alternating magnetic signal to the metal object, such that the alternating magnetic signal is modified by the metal object. The magnetic detector within the probe is also shielded on substantially all sides except a reception face, such that the alternating magnetic signal as modified by the metal object is received into the shielded magnetic detector and converted into a first electrical signal. The signal-conditioning circuit within the probe is shielded on substantially all sides and provided with electrical power. This circuit amplifies the first electrical signal to create a second electrical signal. The signal channel then transmits the second electrical signal to an instrument for analyzing phase and amplitude components of the second electrical signal to provide an indication of the flaw.

Another aspect of the present invention provides an eddy-current probe system for detecting a flaw in a metal object. This the probe includes an excitation coil unit within the probe shielded on substantially all sides except an emission face that transmits an alternating magnetic signal to the metal object, such that the alternating magnetic signal is modified by the metal object, a magnetic detector within the probe shielded on substantially all sides except a reception face, that receives the alternating magnetic signal as modified by the metal object, and generates a first electrical signal, and shielded means within the probe, powered by an external electrical supply, for amplifying the first electrical signal.

Another aspect of the present invention provides an eddy current system capable of providing multiple phase excitation to an eddy current or a remote-field eddy-current probe. The invention also provides various excitation field forms to enhance sensitivity of these techniques to flaws of different orientations and to increase signal image resolutions. In some embodiments, a multiple-phase excitation generates traveling magnetic fields or rotating magnetic fields on an object. Those fields may have a varying direction in an excitation cycle and high scanning speed at the inspected objects without involving any mechanical movement, hence provide sensitivity to a flaw of any orientations and small pitch of signal data.

BRIEF DESCRIPTION OF THE DRAWINGS

FIG. 1B is a block diagram of an eddy scope system 110.

FIG. 2A shows a cross section of one embodiment of a probe 200.

FIG. 2B shows an isometric view of one embodiment of probe 200.

FIG. 3C shows an excitation unit 230C capable of generating a traveling magnetic excitation field.

FIG. 3D shows a cross-sectional view of the excitation unit 230C of FIG. 3C.

FIG. 3E shows another cross-sectional view of the excitation unit 230C of FIG. 3C.

FIG. 4A shows a cross-sectional view of a sensor unit 440.

FIG. 4B shows a face view of sensor 440.

FIG. 6D shows an imaginary&real-signal vs. displacement graph of the results of the scanning operation of FIG. 6A.

FIG. 6E shows an imaginary&real-signal vs. displacement graph of the results of the scanning operation of FIG. 6B.

FIG. 6F shows an imaginary&real-signal vs. displacement graph of the results of the scanning operation of FIG. 6C.

FIG. 7D shows an imaginary&real-signal vs. displacement graph of the results of the scanning operation of FIG. 7A.

FIG. 7F shows an imaginary&real-signal vs. displacement graph of the results of the scanning operation of FIG. 7C.

FIG. 8A shows the configuration of a riveted sample having 10 rivets and two defects.

FIG. 8B shows the configuration of a scanning operation for the sample of FIG. 8A.

FIG. 8D shows an imaginary-signal vs. real-signal graph of the results of the scanning operation of FIG. 8A at 250 hertz.

FIGS. 11A–11H show block diagrams of various probe configurations of single-ended (absolute), and differential and multiple-phase excitation probes, as well as absolute and differential connections for probe sensors and sensor-arrays.

DESCRIPTION OF PREFERRED EMBODIMENTS

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

In the Figures, the same reference number is used throughout to refer to an identical component that appears in multiple Figures. The same reference number or label may refer to signals and connections, and the actual meaning will be clear from its use in the context of the description.

Figure 1A:
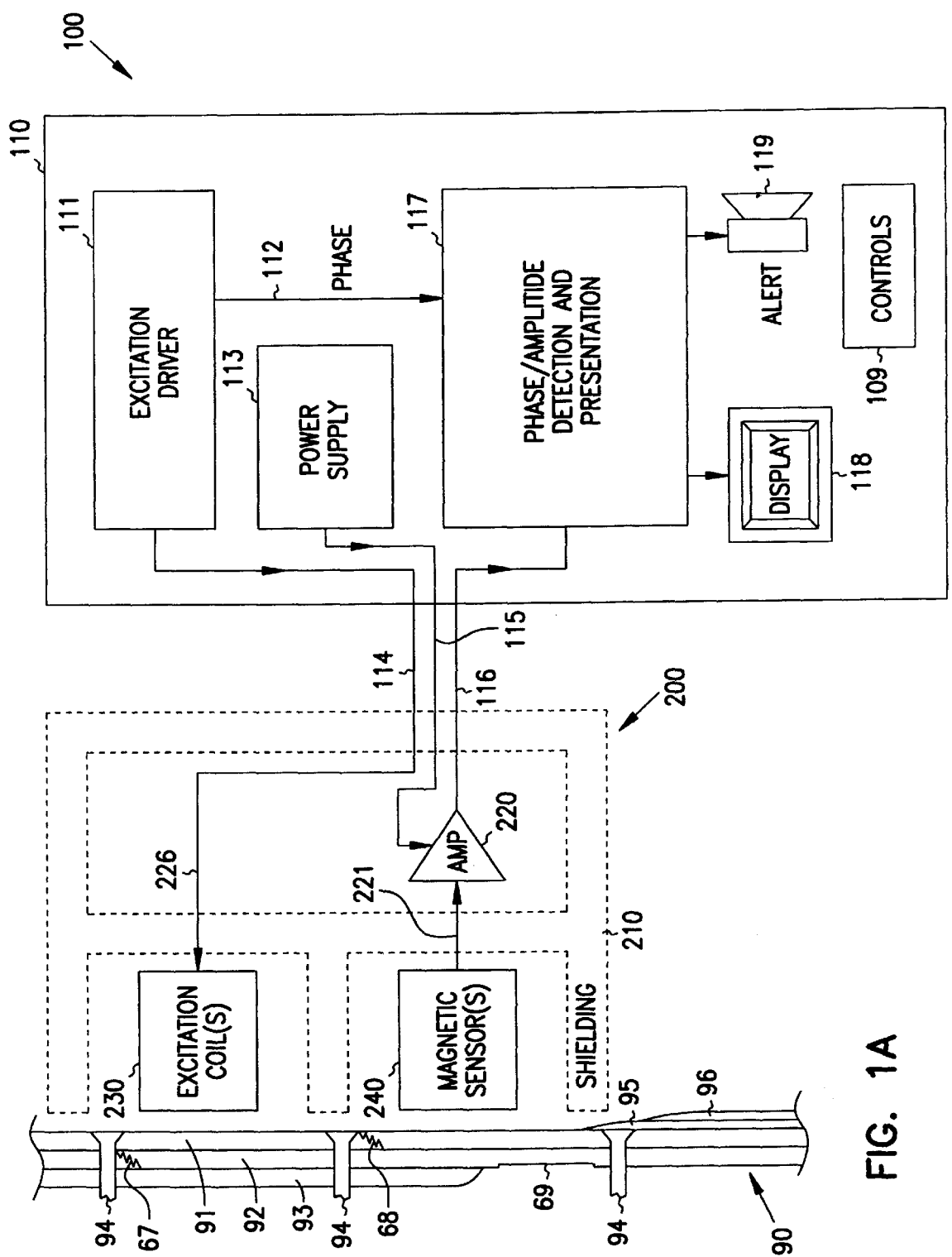
FIG. 1A is a block diagram of a super-sensitive eddy-current system 100.

FIG. 1A is a schematic diagram of super-sensitive eddy-current system 100 according to one embodiment of the present invention. System 100 includes an eddy-scope 110 and probe 200 coupled by a shielded electrical connector. Eddy-scope 110 includes excitation driver 111, power supply 113, phase/amplitude detection and presentation circuit 117, display 118, controls 109, and optionally audio alert 119. Excitation driver circuit 111 provides one or more phases of excitation signal 114 to drive one or more excitation coils 230 in probe 200. Power supply 113 provides electrical power 115 to drive amplifier 220 within probe 200, as well as to other components of eddy-scope 110. Phase and amplitude detection and presentation circuit 117 receives phase signal 112, and conditioned sensor signal 116, and, in one embodiment, generates a signal to display 118 that includes real and/or imaginary components of the sensed signal 116. In some embodiments, distance or time is plotted horizontally, and real and/or imaginary amplitude is plotted vertically. In some embodiments, the amplitude is plotted on one axis (e.g., horizontally), and the phase is plotted on the other axis (e.g., vertically). In other embodiments, the amplitude of the real component is plotted on one axis (e.g., horizontally), and the amplitude of the imaginary component is plotted on the other axis (e.g., vertically). Sensor 200 further includes shielding 210, which in various embodiments includes one or more layers of shielding made of such materials as aluminum, copper, steel, and/or other suitable magnetic and electrically shielding materials. In some embodiments, magnetic sensor or sensors 240 include sensor coils mounted on a ferromagnetic core. Excitation coil or coils 230 typically include a ferromagnetic core and one or more coils of wire.

Display 118 can include graphical displays of phase and amplitude or the relative phases of the output and input signals, and/or other indications of the real and imaginary portions of the received signal 116, as compared to a phase reference 112 of the excitation driver. These displayed signals are used to detect anomalies in the scanned object being tested. Various embodiments of the present invention are used to scan the metal surfaces of materials such as airplane wings having rivets and/or paint and applique surfaces under which the metal is being tested for cracks or other indications of failure or fatigue.

Figure 9A:
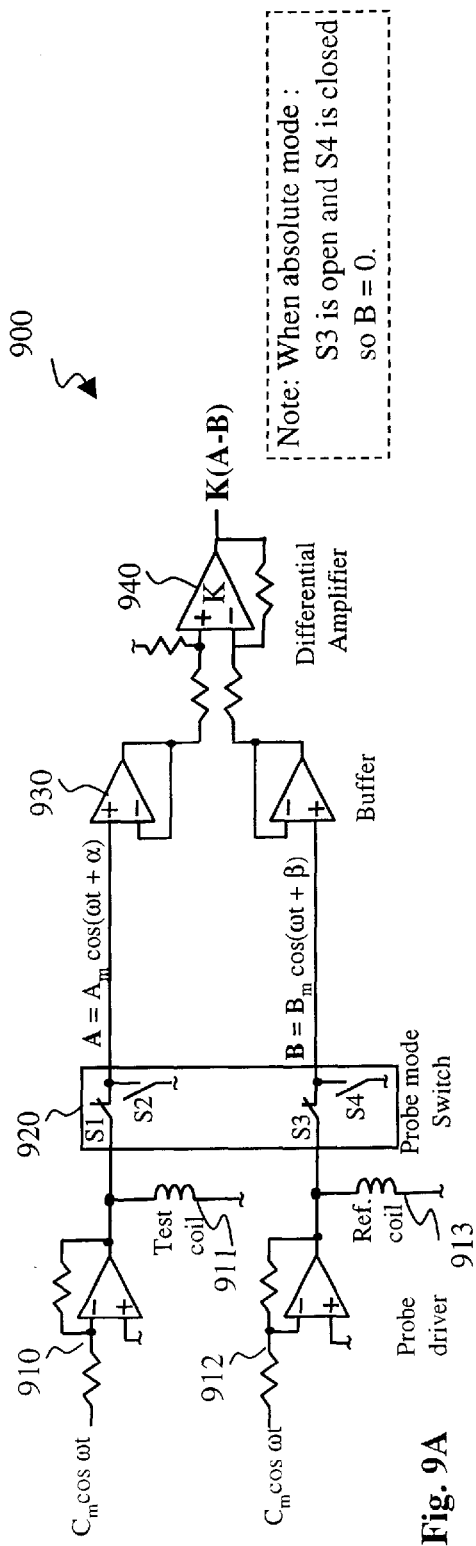
FIG. 9A shows a bridge circuit useful for driving probe 200 from driver 111.

FIG. 1B is a block diagram of a single-phased eddy scope system 110. System 110 includes driver 111 and receiver/analyzer 117. In some embodiments, driver 111 includes a sine- and cosine-wave generator 510 that outputs $\sin\omega t$ and $\cos\omega t$ signals (collectively signal 112), wherein the $\cos\omega t$ is amplified by one or more constants (e.g., A and B) by blocks 512 and 513, and are driven by output stages 514 and 515 respectively into bridge circuit 520 (shown in more detail in FIG. 9A) to drive probe 200. FIG. 9A shows a schematic of an exemplary bridge circuit useful for driving probe 200 from driver 111. Receiver/analyzer 117 receives one or more preamplified signals from probe 200 (e.g., signals $C^*\cos(\omega t+\alpha 1)$, and $D^*\cos(\omega t+\alpha 2)$ from bridge 520, wherein C/A is the amplitude ratio for the first signal, and $\alpha 1$ is its phase shift due to the probe interaction with the structure and material being tested, and D/B is the amplitude ratio for the second signal, and $\alpha 2$ is its phase shift. These signals are combined in differential gain and pre-gain stage 531 to generate signal $E^*\cos(\omega t+\alpha)$, where $\alpha=\alpha 1-\alpha 2$. The signal $E^*\cos(\omega t+\alpha)$ is then multiplied in demodulators 532 and 533 by $\cos\omega t$ and $\sin\omega t$ respectively, and the respective results are passed through low-pass filters 534 and 535 respectively, and then H-channel post-gain amplifier 536 and V-channel post-gain amplifier 537 respectively, thus resulting in signals labeled X and Y, respectively. Rotation circuit 540 provides a linear transformation to rotate (relative to the analyzer or display screen) the X and Y signals by an angle $\theta$ set by a user on the eddy-scope screen, (having inputs $\sin\beta$ and $\cos\beta$, and generating outputs labeled signals H and V, respectively. The controls of the instrument allow the user to set this rotation (i.e., rotating the X-Y signals for plotting), in order to more easily separate changes due to defects from those that are not related to defects. In some embodiments, the phase rotation is initially set to 0 degrees for a non-defect signal, e.g. lift-off signal, so that the vertical indications fully represent defect signals.

Analog-to-digital converters 542 and 543 then digitize the results to create a stream of digital output values H-O and V-O which can be stored in a digital memory and/or displayed and/or further processed to extract other information.

Figure 1C:
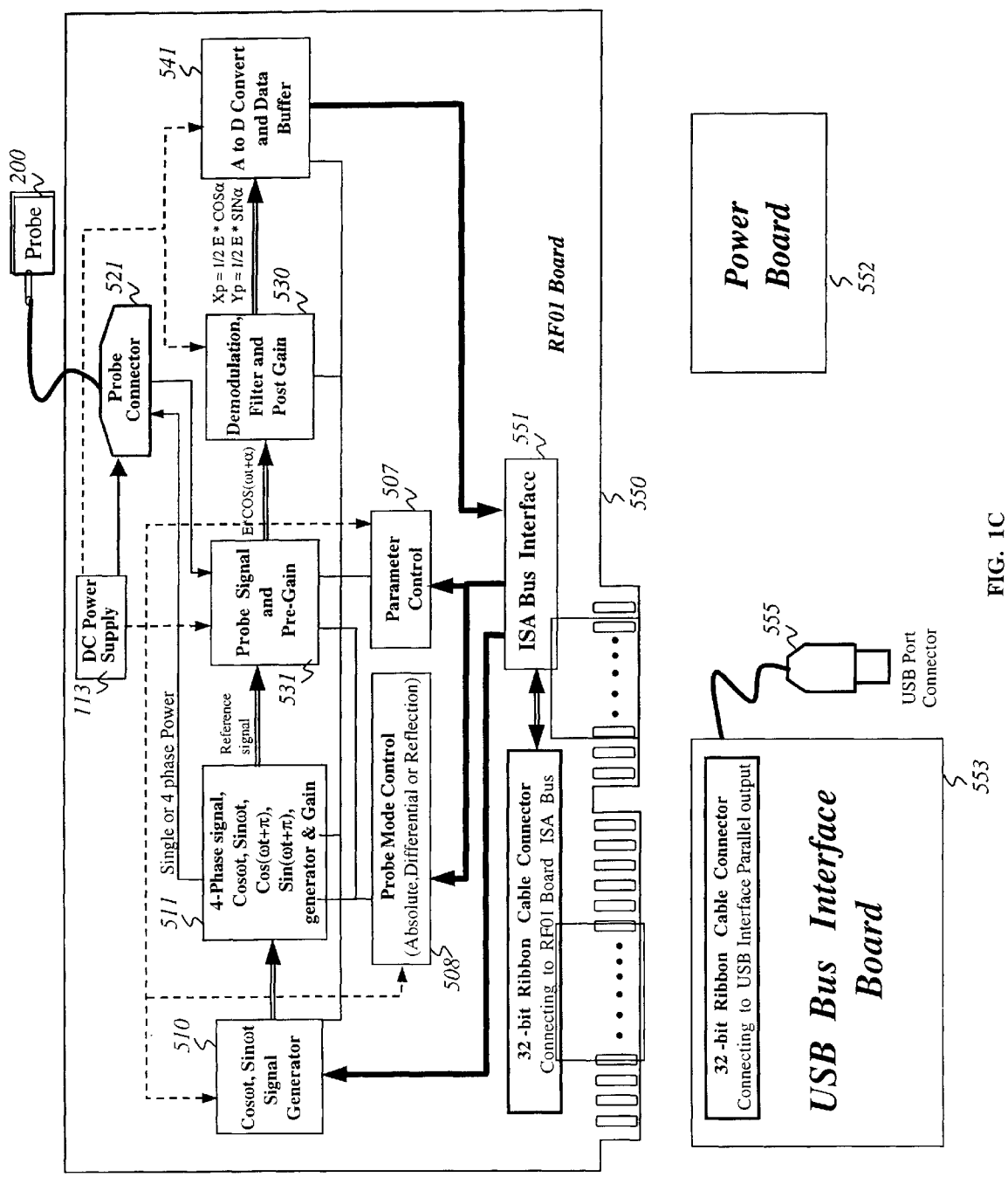
FIG. 1C is a block diagram of an eddy-scope board for an eddy scope system 110.

FIG. 1C is a block diagram of an eddy-scope board for a four-phased eddy scope system 110. In this embodiment, signal generator 510 provides $\cos\omega t$ and $\sin\omega t$ signals to drive 4-phase circuit 511. Circuit 511 generates either single-phase (such as described in FIG. 1B above) or four phase (i.e., the plus and minus phases values (unity gain and unity inversion) of both the $\cos\omega t$ and $\sin\omega t$, thus yielding four signals each 90 degrees from the last and the next). Circuit 511 also provides one phase of the four-phase power to the bridges circuit 520/531 that is connected to probe connector 521 and then to probe 200, and four-phase power to connector 521 and then to probe 200. Four-phase signals (and other multiple-phase signals) are useful for driving traveling-wave and rotating-wave probes such as described below. The drive signals (either single-phase or four-phase) are controlled by probe mode control 508 that selects either: absolute, differential, or reflection drive-receive configuration mode under program control of the personal computer, laptop computer, or other major controller.

In some embodiments, an operator practices with a test object having known cracks or thinning, and learns to recognize the indications of flaws. This provides the simplest instrument, but requires a trained operator. In other embodiments, eddy scope instrument 110 is calibrated by scanning a known good part or object, and the indications of the received good signal are recorded. Then a similar object having possible flaws is scanned using the same or similar pattern of scanning, and the resulting received signal is compared to the known good signal to detect differences indicative of flaws. In yet other embodiments, the signatures of certain flaws are recorded in eddy scope instrument 110 (e.g., a memory within control functional block 109), and a pattern-recognition program is used to distinguish "good" signals (indicative of non-flawed parts) from "bad" signals (indicative of flaws), and an indication or the results is provided to display 118 and/or audio alert-device 119.

The present invention provides an excitation signal in the form of an alternating magnetic field, which is coupled to and into the specimen 90 under test. In turn, eddy-current fields are generated within object 90. When the magnetic field and the eddy-current fields interact with an anomaly such as a rivet or a crack or a thinning of a sheet of metal, the magnetic field above that anomaly is affected, in both phase and amplitude. A probe is called an eddy-current probe if it detects a magnetic field affected by eddy-currents in the object 90. Remote-field eddy-current probes are a subset of embodiments that detect fields wherein the magnetic field has passed through a conducting plate or tube 90 twice, i.e., from the excitation unit 230, through plate 90, then back through plate 90 and is received by detector 240.

In some embodiments, this alternating magnetic field is an "absolute" field, wherein a single-pole electromagnet (see, e.g., FIG. 3A below) is driven with a single-phase electrical signal 114. Over time, such a magnetic field travels radially outward, along and within conducting object 90. That is, such fields propagate relative to detector 240 along the line between excitation unit 230 and detector 240 (i.e., radially outward). In other embodiments, a rotating magnetic field is provided, wherein the field is generated by a plurality of coils (arranged, for example, along a circle), each driven with a different phase of an excitation signal 114, such that a phase front of the signal is rotated around the circumference of the face 250 of the excitation coil unit 230B (e.g., see FIG. 3B below, wherein each of six coils is driven by a different phase (e.g., a phase that is 60 degrees (for a six-phase excitation signal) or 120 degrees (for a three-phase excitation signal) offset from the last phase of signal 114)). Such fields propagate relative to detector 240 at a tangent to the line between excitation unit 230 and detector 240. In yet other embodiments, a traveling magnetic field is provided, wherein the field is generated by a plurality of coils (arranged, for example, along a straight line), each driven with a different phase of an excitation signal 114, such that a phase front of the signal is move linearly along the face 250 of the excitation coil unit 230C (e.g., see FIGS. 3C and 3D below, wherein each of three coils is driven by a phase that is 120 degrees offset from the last phase of signal 114). Such fields propagate relative to detector 240 linearly between excitation unit 230 and detector 240. One conducting object 90 that is examined by some embodiments of the present invention is the outer metal skin of aircraft. Such objects can include multiple layers 91, 92, and/or 93 of similar or dissimilar metals (such as aluminum, titanium, and steel), even when rivets 94 and/or paint or other appliques 95 and/or 96 are present. In some embodiments, the paint layer 95 and/or applique layer 96 extends across the area being scanned (i.e., such layers are between the scanner 200 and the aluminum layers) and the defects are still detected whether or not such paint and/or applique layers are present. Cracks 67 or 68 or layer thinning 69 (for example due to metal fatigue or corrosion) can be detected because the phase and/or amplitude of the detected signal is changed due to such anomalies. Even though rivets 94 change the received signal, a rivet without a nearby crack will provide a different signal from a rivet having a crack in either the rivet or the adjacent sheet of metal. In some embodiments, the phase and amplitude (or alternatively, the amplitudes of the real and the imaginary components) of the received signal are displayed (e.g., as a graph on a display screen), and an experienced operator can visually distinguish displayed signals (signature patterns) indicative of normal situations from signatures indicative of thinning corrosion, cracks, or poor welds. In other embodiments, pattern recognition software is used to analyze and augment the displayed signals to identify signals indicative of flaws. Further, both cracks in the surface metal 91 (e.g., crack 67) as well as cracks 68 in underlying (hidden) sheets 92 provide signatures that are different than signals of objects that do not have such flaws.

In typical embodiments designed for detecting multi-layered aircraft aluminum skin, an excitation signal (and thus a received signal) having a frequency of between about 100 and about 5000 hertz is used. Generally, higher frequencies are used when inspecting thinner plates or structures, and lower frequencies are used when inspecting thicker plates or structures. In some embodiments, frequencies as low as about 10 hertz are used in order to penetrate and inspect thicker plates. In some embodiments, a probe designed to provide a penetration depth, when driven by an excitation signal of appropriate amplitude and detected with a probe-preamplifier system of appropriate sensitivity and noise immunity, of at least approximately four millimeters (4 mm), for example is used. In other embodiments, probes are designed for other depths, depending on the structure that is to be examined. Pure aluminum has a higher conductivity that the aluminum typically used for aircraft surfaces and structures, and a probe that is designed for a given depth assuming pure aluminum will work for deeper flaws in metal having lower conductivity. In practice, such a 4 mm design-point probe is often capable of detecting cracks as deep as thirteen millimeters or more (i.e., defect-free in the top 13 mm, but a break or other large defect just below that), and capable of detecting corrosion thinning of 1% or less in plate structures of up to about 6 mm. Further, cracks as short as 0.031 inch long and 0.446 inches deep on the side of a fastener hole (a quite complex geometry having a small crack deep in the test object) are detectable by some embodiments of the invention. Conventional probes for such applications did not have a preamplifier in the probe, nor sufficient shielding of both the magnetic and electrical circuits. Thus, the present invention provides, for the first time, both low-noise preamplification and good magnetic and electrical shielding within the probe (as well as a very short connecting wire between the sensor 230 and the preamplifier 220), and thus is better able to provide information regarding cracks, thinning, rivets, and other details of and within the conducting object 90, for example, an airplane wing or other structure.

One major advantage of the present invention is in providing shielded preamplification in the probe 200. There is a need to detect very small signals associated with the eddy-current effects on the alternating magnetic field from excitation unit 230. In some embodiments, the received signal is on the order of a fraction of a microvolt to a few microvolts. In some embodiments, signal-conditioning circuit provides an amplification of 1000 times. In other embodiments, signal-conditioning circuit provides an amplification of 100 times. In some embodiments, signal-conditioning circuit also provides a low-pass filter function, in order to remove high-frequency noise.

Other embodiments of the present invention provide preamplification wherein preamplifier circuit 220 is not shielded.

FIG. 2A shows a cross section of one embodiment of probe 200. In one embodiment, probe 200 includes an aluminum shielding container 210 that includes an excitation unit 230, a sensor unit 240, and a shielded amplifier 220. Cable 260 connects probe 200 to an eddy-scope, for example, eddy-scope 110 of FIG. 1A. In one embodiment, cable 260 includes signal connectors for the excitation (input) drive signal 225, power conductors 224, and sensed and conditioned (output) signal 223 which provides the results back to the eddy-scope. In one embodiment, excitation unit 230 is inserted into a pocket 273 (see FIG. 2D) in aluminum case 210, and includes a cup-shaped copper shield 231 (which has a pocket 283) surrounding a ferrite core 232, the ferrite core 232 having a center post surrounded by coil 233. Steel ring 237 is provided in some embodiments to reduce flux leakage from coil 233. A small hole is drilled through copper shield 231 and housing 210 to facilitate each of one or more signal wires 226 connecting the excitation coil 233 to the circuit board of circuit 220. In one embodiment, sensor unit 240 includes a cup-shaped copper shield 241, a C-shaped steel flux bypass structure 247, an E-shaped ferrite core 242, and a coil 243 having a high number of turns of fine wire in order to provide high sensitivity to small magnetic fields. In one embodiment, coil 243 and the other components within cup 240 are imbedded in an epoxy or other suitable potting material. In one embodiment, a small hole is drilled through copper shield 241 (which has a pocket 284—see FIG. 2D), aluminum housing 210 in order to route one or more signal wires 221 from coil 243 to circuit 220. In the embodiment shown, circuit 220 includes operational amplifier 222 along with other suitable feedback and/or other conditioning circuit components to provide a preamplification and signal-conditioning function to the sensed signal. The output of amplifier 222 is indicated on wire 223 of FIG. 2A and signal 116 of FIG. 1A. Sensing face 250 of sensor 200 is placed next to, and moved along, the surface of the item being tested. When sensor 240 or excitation coil 230 is adjacent features such as rivets or cracks or other anomalies, the eddy-current excited by excitation unit 230 within the device being tested will cause phase and/or amplitude of the magnetic field under the sensor unit to change. In some embodiments, there is a larger signal when excitation coil 230 passes an anomaly than when sensor 240 passes the same anomaly.

FIG. 2B shows an isometric view of one embodiment of sensor 200. This view shows sensing face 250 having a sensor unit 240 and an excitation unit 230.

Figure 2C:
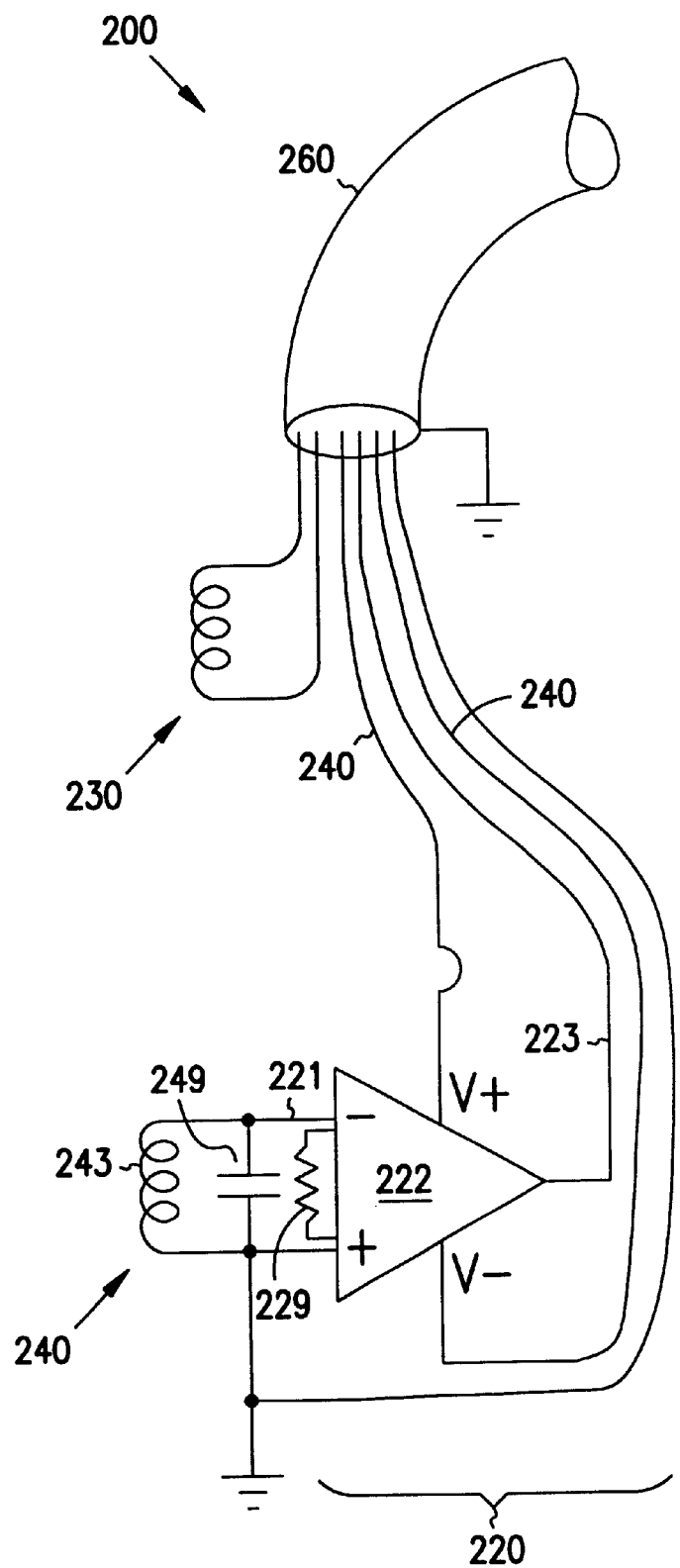
FIG. 2C shows a schematic diagram of probe 200.

FIG. 2C shows a schematic diagram of probe 200. Sensing unit 240, shown here as including a coil 243, provides input to amplifier 220, which typically includes op amp 222 and gain-setting resistor 229. In one embodiment, op amp 222 is implemented as an LT1167A low-noise operational amplifier (available from Linear Technologies, Inc.) is used, wired to a printed circuit board with an appropriate gain-setting circuit (e.g., replacing the gain-setting resistor 229 shown in FIG. 2C) to provide the desired amplification factor and stability. FIG. 2F shows one such embodiment. In some embodiments, a capacitor 249 (e.g., 100 picoFarads) is wired across coil 243 to reduce high-frequency noise (i.e., this provides a low-pass filter function). In some embodiments, suitable offset-nulling circuitry (such as recommended by the supplier of op amp 222) is also used to reduce offset errors and drift. In one embodiment, op amp 222 is provided plus and minus voltage (V+ and V-) power 240 from cable 260 and thus from eddy-scope 110 (see FIG. 1A). In other embodiments, sensor unit 240 includes one or more giant magneto-resistive (GMR) sensors (or magneto-resistive (MR) sensors) in other embodiments) along with suitable biasing circuitry. FIG. 2C also shows schematically excitation unit 230 as an electromagnetic coil. In some embodiments, cable 260 includes rounded shields surrounding each separate signal conductor, for additional grounding and shielding. The sensitivity and low noise characteristics of the present invention are particularly enhanced by providing a powered preamplifier circuit 220 within, and shielded by, probe 200, and more particularly, by keeping the wires 221 (and the traces on any circuit board holding circuit 222) that connect sensor 240 to preamplifier 220 very short, in order to minimize electromagnetic noise picked up by these conductors. In one embodiment, e.g., short wires are obtained by feeding the wires from the back of the coil 243 through holes in the back of the shield pocket and pulling them tight as the coil assembly is inserted into the shield. The wires then thread through holes in the preamplifier circuit board and the circuit board is slid down over the wires as the circuit board is inserted into its pocket on the opposite side of the shield case, the wires are pulled tight and soldered them in place, wherein the preamplifier op-amp circuit 222 is located next to where the wires come onto the circuit board.

Figure 2D:
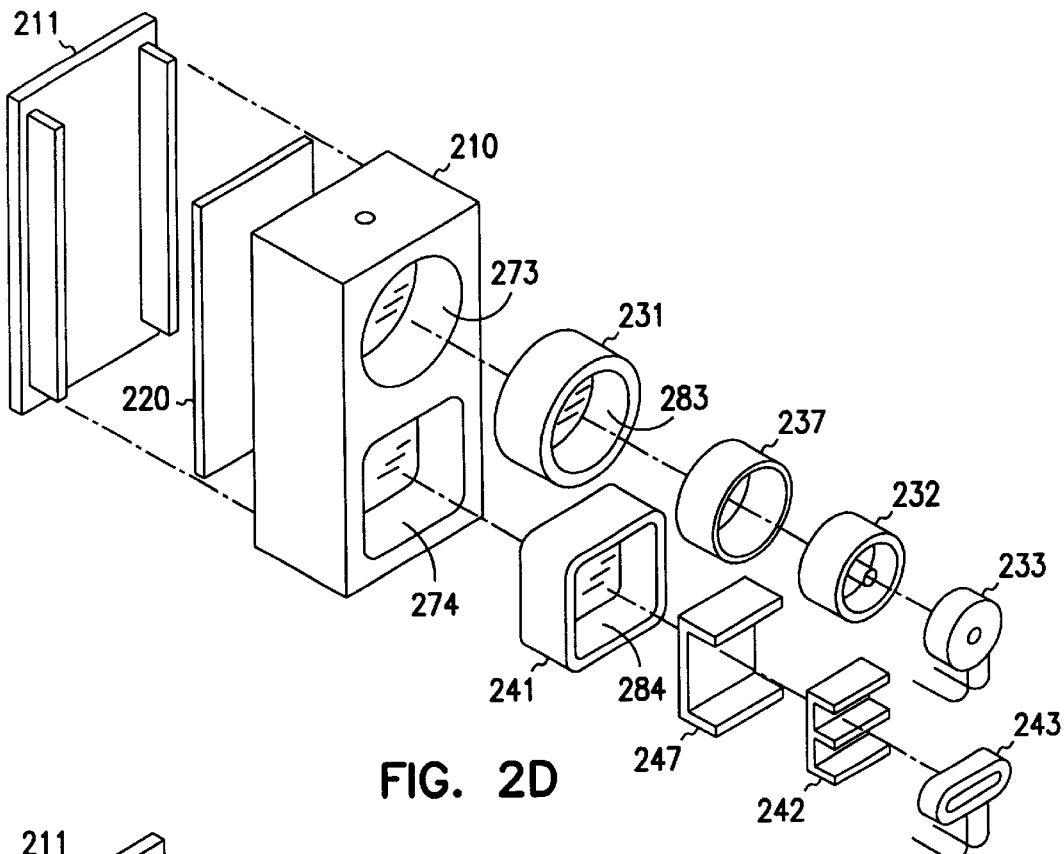
FIG. 2D shows an exploded view of probe 200.

FIG. 2D shows an exploded view of probe 200. The various parts of this embodiment are described above.

Figure 2E:
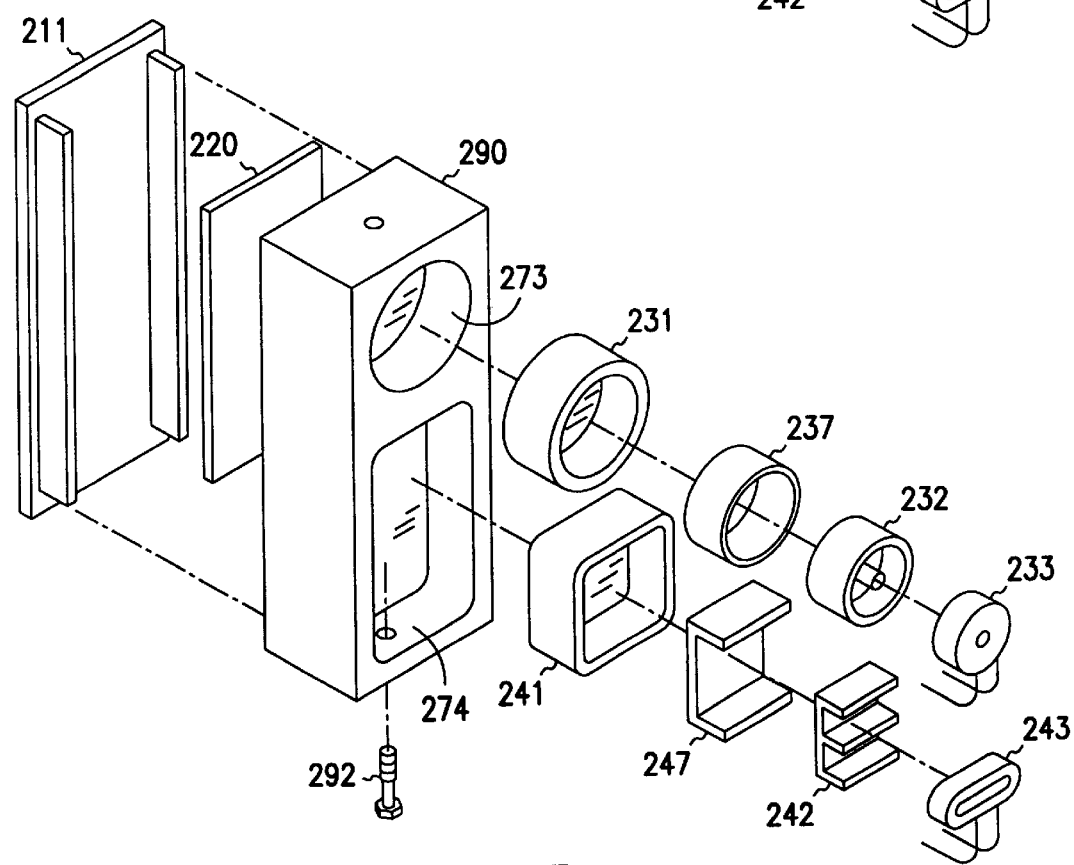
FIG. 2E shows an exploded view of an adjustable probe 200.
Figure 2F:
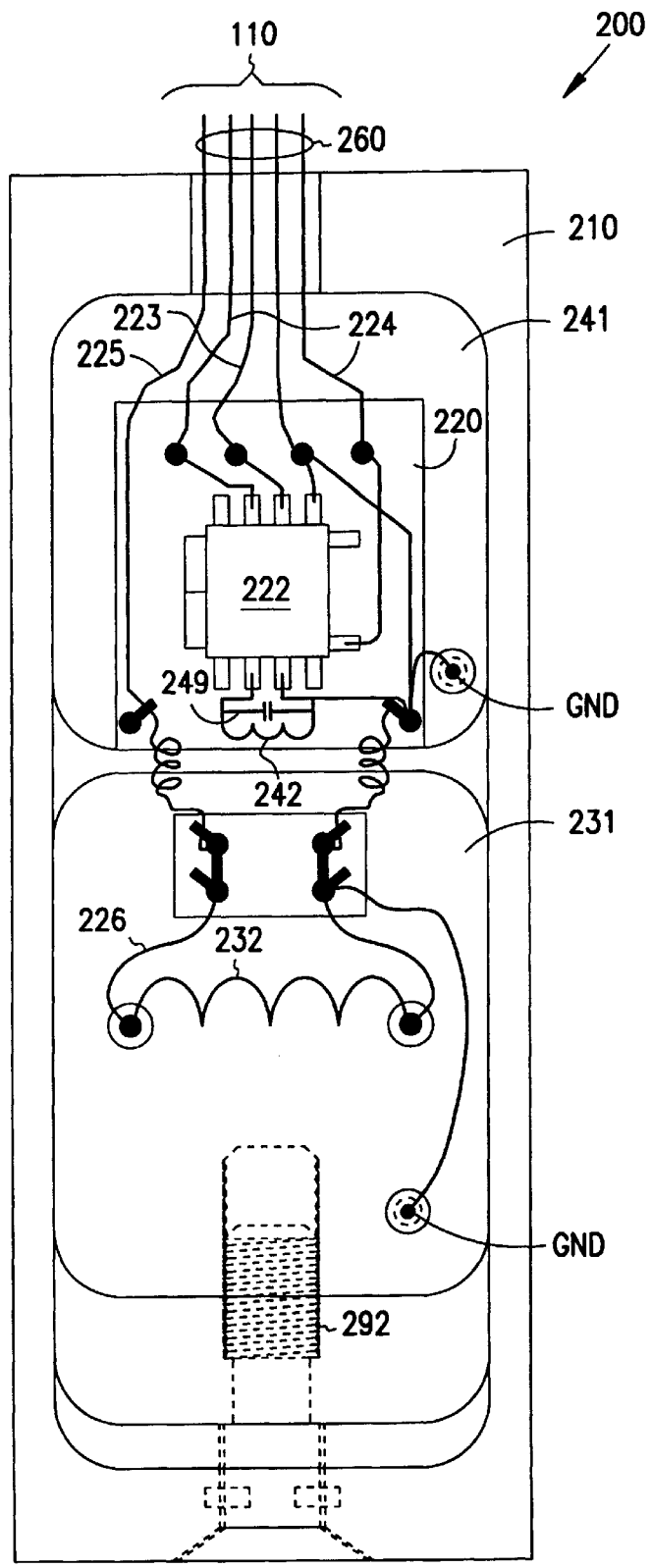
FIG. 2F shows a back view of an adjustable probe 200.

FIG. 2E shows an exploded view of an adjustable probe 200. This embodiment's adjustable probe 200 includes the same inner parts as the non-adjustable probe 200 of FIG. 2D and 2A, except that pocket 274 in aluminum case 290 is elongated to allow the spacing between the excitation unit 230 and the pickup unit 240 to be adjusted (screw 292, made of brass in one embodiment, moves pickup unit 240). In some embodiments, this allows various spacings to be empirically tried to determine an optimal spacing for the material being tested and the frequencies being used. This optimal spacing is then used to build a non-adjustable unit such as in FIG. 2D. In other embodiments, the adjustable unit is used in production situations to allow the user to optimize the spacing for each different measurement situation.

FIG. 2F shows a schematic back view of an adjustable probe 200. In this view, a pocket in the back of block 210 houses circuit board 220, on which pre-amp 222 is mounted opposite sensor 241. Coiled wires connect from sensor block 241 to movable excitation block 231, in order to facilitate movement of the excitation block 241 by screw 292, thus adjusting the excitation-to-sensor spacing. Capacitor 249 provides a low-pass filter function, limiting high-frequency noise. In some embodiments, an aluminum shield plate is used underneath circuit board 220, to prevent signals from the front of the probe face, and an aluminum shield cover seals the back of block 210, with block 210 shielding the sides, thus enclosing and shielding amplifier circuit 222 and the signal wires from picking up external noise signals.

Figure 3B:
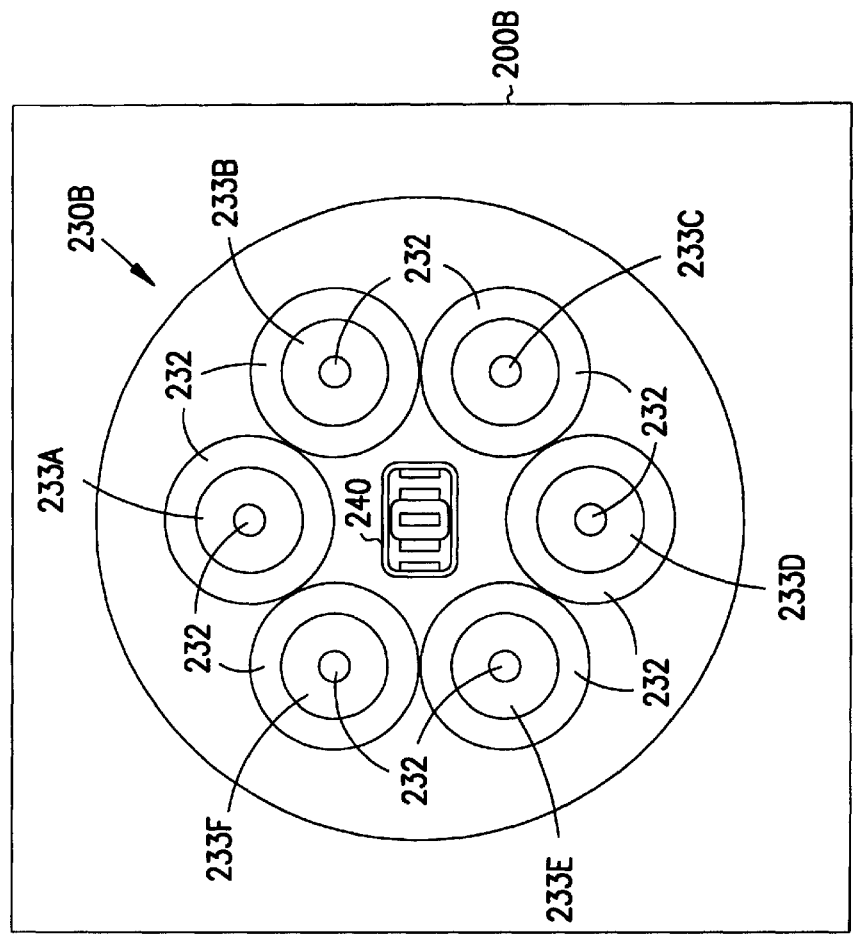
FIG. 3B shows an alternative excitation unit 230B, capable of generating a rotating excitation magnetic field.
Figure 3A:
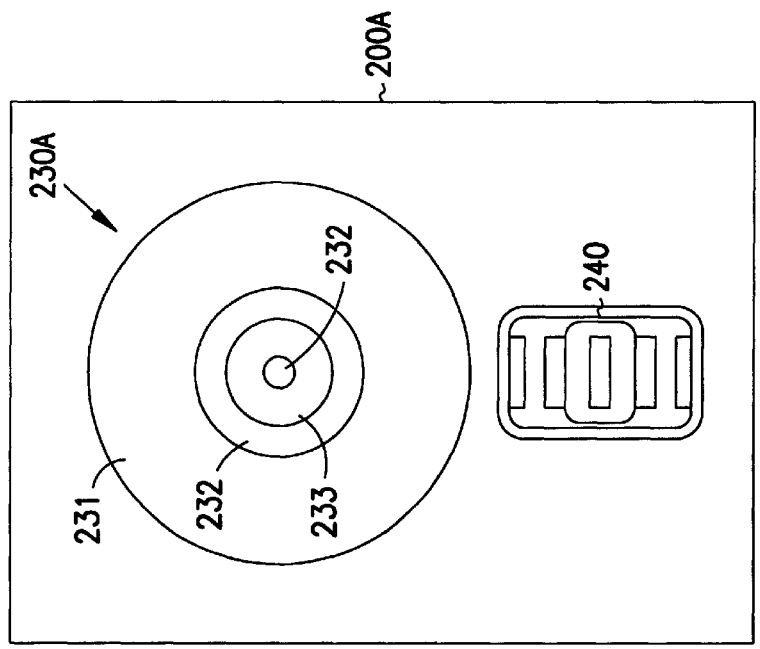
FIG. 3A shows a face view of a single-pole excitation coil 230A.

FIG. 3A shows a face view of a single pole excitation coil 230A. Excitation unit 230A includes a shield 231, for example, made of high purity copper. Ferrite core 232 includes a cup-shaped outer structure and a post inner structure, the inner post surrounded by a coil 233 having a suitable impedance for being driven by excitation circuit 111 (see FIG. 1A). The cross-section view of excitation unit 230A corresponds to the cross-section view of excitation unit 230, as shown in FIG. 2A.

FIG. 3B shows an alternative excitation unit 230B, capable of generating a rotating excitation magnetic field (i.e., the field traveling or moving in a circumferential direction relative to the planar face, also called a planar rotating magnetic field). In this embodiment, excitation unit 230B includes an outer cup-shaped copper shield 231 having six pockets, each pocket containing a ferrite core 232, each ferrite core having a respective coil 233A, 233B, and 233C. In one embodiment, copper shield 231 includes six pockets not all the way through the copper shield. Each pocket containing its own ferrite core 232 having a cross-section appearance similar to the cross section of ferrite core 232 of FIG. 2A. In these embodiments, a three-phase or six-phase excitation signals is used. In some such embodiments (for example, a three-phase excitation circuit), a look-up table contains digital values corresponding to successive points along a sine wave, and three digital-to-analog (D/A) converters are loaded with values from the table (e.g., the first D/A is fed values starting at 0 degrees, the second D/A is fed values starting at 120 degrees, and the third D/A is fed values starting at 240 degrees). For six-phase excitation, three D/A converters are used, and the three signals are inverted to provide the other three phases (the inverted 0-degree signal provides the 180-degree phase, the inverted 240-degree signal provides the 60-degree phase, and the inverted 120-degree signal provides the 300-degree phase), for a total of six phases. In other embodiments, an off-the-shelf sine-and-cosine generator is used to provide 0 degree and 90 degree phases of the excitation signal, respectively, and the inverted versions of these signals provide the 180 and 270 degree phases respectively, for a total of four phases. This can provide a lower-cost signal source. In such embodiments, four, eight, twelve (or other multiple of four) ferrite cores are used, arranged in a circle. In some such embodiments, a plurality of sensors 240 are arranged around the periphery of the excitation structure, thus allowing the field to be scanned (moved) around the probe without moving the probe. By not moving the probe, a cleaner (having less noise and variation) signal can be obtained than if the probe is moved during the measurement.

FIG. 3C shows cross-section view of a sensor unit 240 capable of detecting a traveling magnetic excitation field. FIG. 3E shows cross-section view of an excitation unit 230C capable of generating a traveling magnetic excitation field (i.e., the field traveling or moving in a linear direction). In some embodiments, excitation unit 230C includes a cup-shaped copper shield 231, the pocket in shield 231 enclosing a plurality of individual coils 233, the coils 233 on individual prongs of a ferromagnetic core 232.

In some embodiments, excitation unit 230C includes a cup-shaped copper shield 231, the pocket in shield 231 enclosing a plurality of individual coils 233, the coils 233 on individual prongs of a ferromagnetic core 232. In some embodiments, two or more linear excitation units 230C are provided, in a parallel orientation on either side of one or more sensors 240 which are located between the excitation units 230C, in order to obtain a more uniform traveling magnetic wave (see FIG. 10A for one example). In the embodiment shown in FIG. 3D, the plurality of core fingers 232 and coils 233 are aligned along a straight line to generate a straight linear traveling wave.

In other embodiments, the plurality of core fingers 232 and coils are aligned along other open or closed shapes (and having either a planar face or a non-planar face) such as polygons or curves, depending on the object to be measured.

FIG. 3D shows a face view of the probe 200C having the excitation unit 230C of FIG. 3C. In the embodiment shown, ferrite core 232 is an E-shaped block, having twelve coils, 233A, 233B, and 233C–233J, each coil formed around its own respective prong of multi-pronged E-shaped ferromagnetic core 232. In some embodiments of the excitation unit of FIG. 3B and the excitation unit of FIG. 3C, the excitation signal driving the coils, 233A–233l is a multi-phase sign wave signal such that the magnetic field generated travels in a rotating fashion (for FIG. 3B) or a linear fashion (as in FIG. 3D). In some embodiments, a four-phase excitation signal is used; in other embodiments, a three-phase or six phase or N-phase excitation signal used. As discussed above, a single sine-value lookup table (e.g., read-only memory) is used for some embodiments to load values into N D/A converters (or N/2 D/A converters each feeding an inverter to each provide two phases) in order to generate an arbitrary number of phases to drive a multi-phase excitation probe (either linear or rotating).

FIG. 3E shows an isometric view of a rotating-field probe 200E used to test pipe-like structures from the inside. Probe 200E generates a cylindrical rotating field (i.e., the field traveling or moving in an outside circumferential direction relative to the outside cylindrical face, also called an outside cylindrical rotating magnetic field). In some embodiments, twelve excitation coils 233A–233L are placed on fingers of core 232 and are driven by three or four phases (each shifted in phase 120 or 90 degrees, respectively from the others), however other embodiments use fewer or more coils, fewer or more fingers, and fewer or more phases of excitation signal. Some embodiments use four phases because of the readily available and inexpensive sine/cosine wave generators. The magnetic field thus is rotated in the direction shown by an arrow in the figure, and pickup units 240 detect the eddy-current signal to locate any flaws. FIG. 3E'. In contrast to the probe of FIG. 3B that generates a rotating field on a planar surface, the probe of FIG. 3F provides a rotating field for a tubular structure probed from the inside.

In some embodiments, each coil is placed around three successive cores (e.g., coil 233A around cores 1, 2, and 3, coil 233B around cores 2, 3, and 4, and so on until coil 233L around cores 12, 1, and 2). In some other embodiments, each coil is placed around four successive cores (e.g., coil A around cores 1, 2, 3 and 4, coil B around cores 2, 3, 4 and 5, and so on until coil J around cores 12, 1, 2 and 3). In some embodiments, multiple sensors are provided on a cylindrical outer face in a separate unit that is axially spaced from the excitation unit.

Figure 3F:
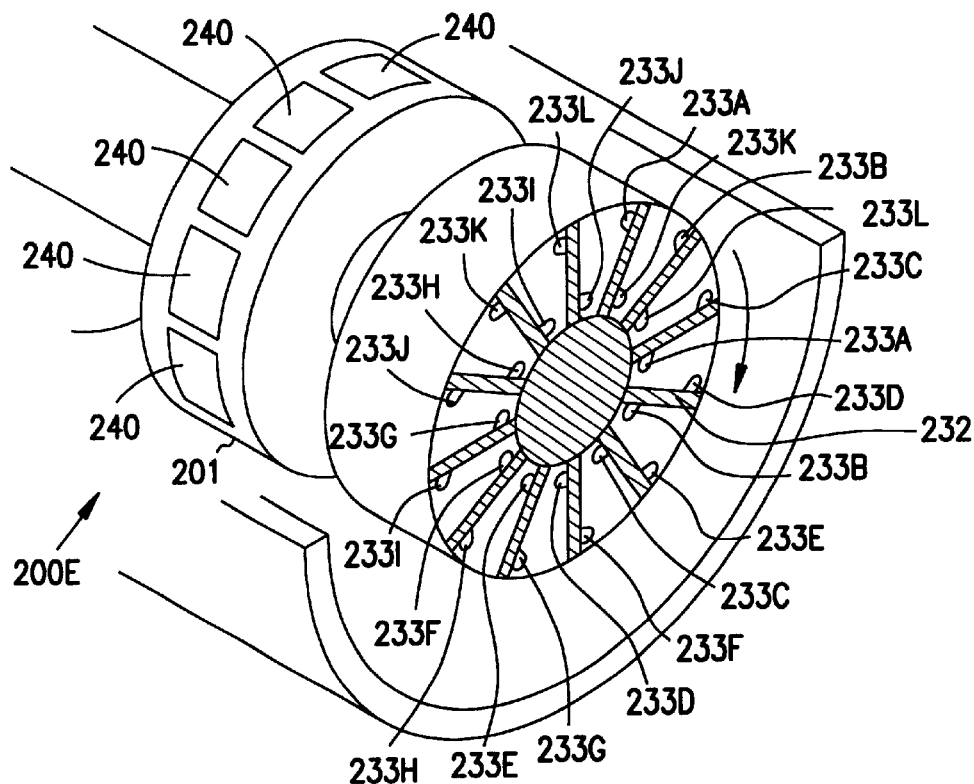
FIG. 3F shows a cross-section isometric view of a rotating-field probe 200E used to test pipe-like structures from the inside.

FIG. 3F shows a cross-section isometric view of a rotating-field probe 200E used to test pipe-like structures from the inside. FIG. 3G shows an isometric view of the rotating-field probe 200E of FIG. 3F.

Figure 3H:
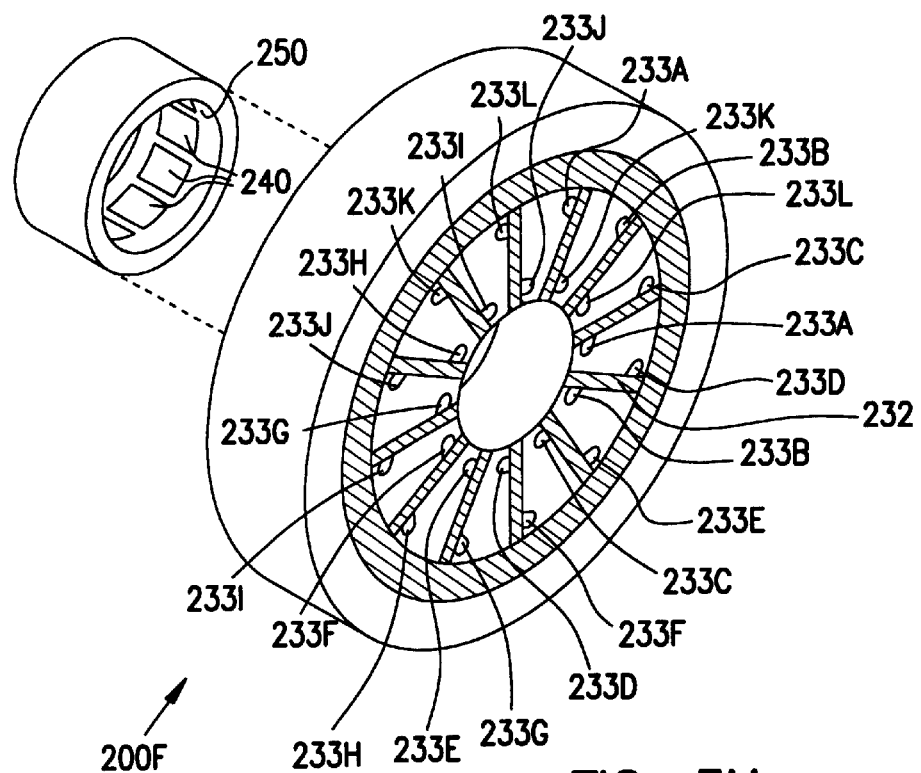
FIG. 3H shows an isometric view of a rotating-field probe 200F used to test pipe-like structures from the outside.
Figure 3G:
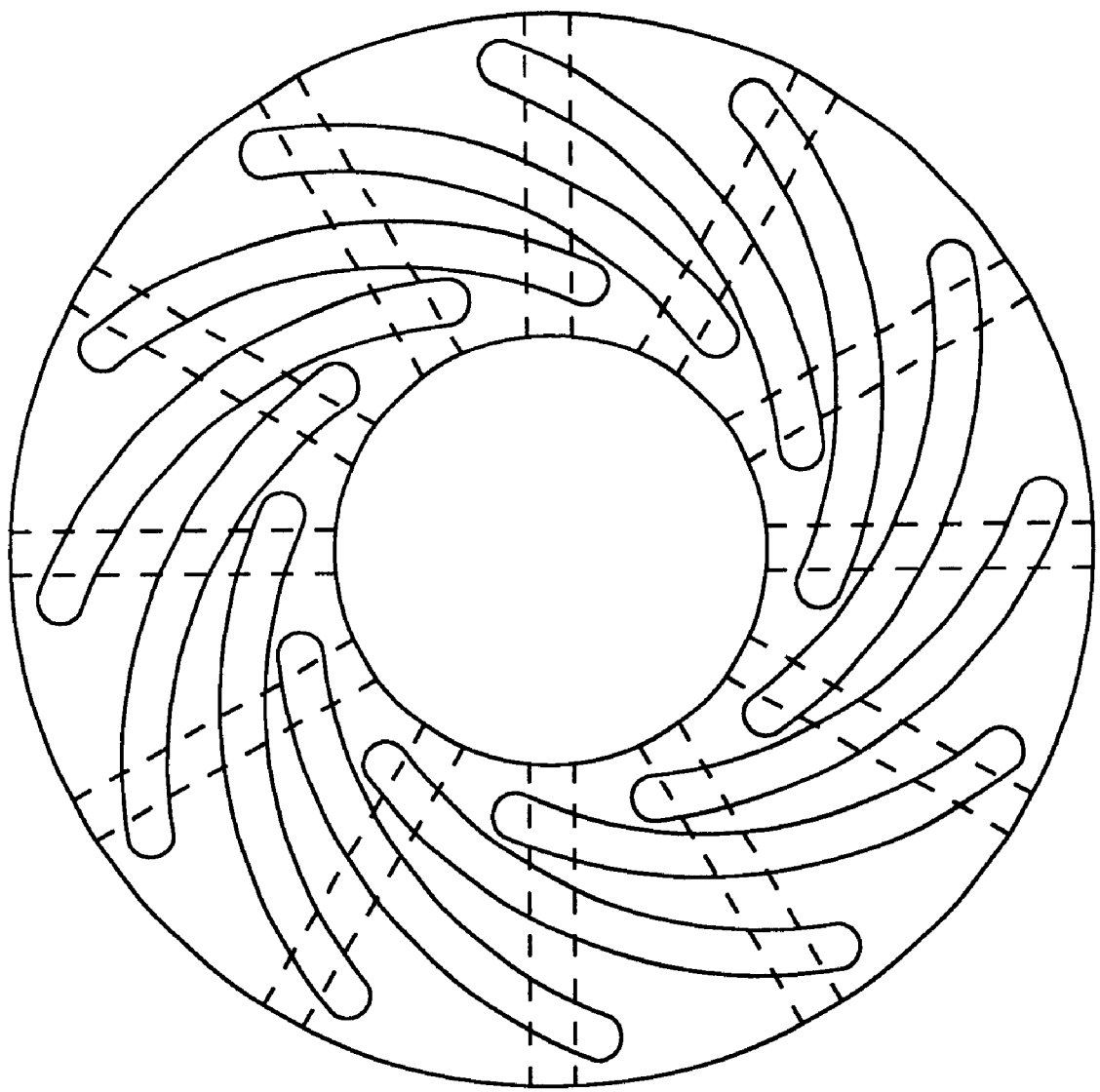
FIG. 3G shows an isometric view of the rotating-field probe 200E of FIG. 3F.

FIG. 3H shows an isometric view of a rotating-field probe 200F used to test pipe-like structures from the outside. Probe 200E generates a cylindrical rotating field (i.e., the field traveling or moving in an inside circumferential direction relative to the inside cylindrical face, also called an inside cylindrical rotating magnetic field). This embodiment shows six coils 233A–233F that can be driven by a three-phase or a six-phase excitation signal to generate a rotating magnetic field in the pipe being tested. In some embodiments, multiple sensors are provided on a cylindrical inner face in a separate unit that is axially spaced from the excitation unit. Other embodiments provide multiple sensors on a cylindrical inner face in the same unit as the excitation coils.

FIG. 4A shows a cross-sectional view of an alternative embodiment of a sensor unit 440 (which can be substituted for sensor unit 240 of FIG. 2A). In this embodiment, sensor unit 440 includes cup-shaped copper shield 241, C-shaped steel flux bypass structure 247, C-shaped ferromagnetic core 442, and two coils, 443A and 443B, wired in a differential manner. Reference numeral 250 indicates the sensing face of sensor 440.

FIG. 4B shows a face view of sensor 440. Again, sensor 440 includes copper shield 241, steel flux bypass structure 247, ferrite core 442, and differentially connected coils 443A and 443B, all imbedded in potting compound 244.

Figure 4C:
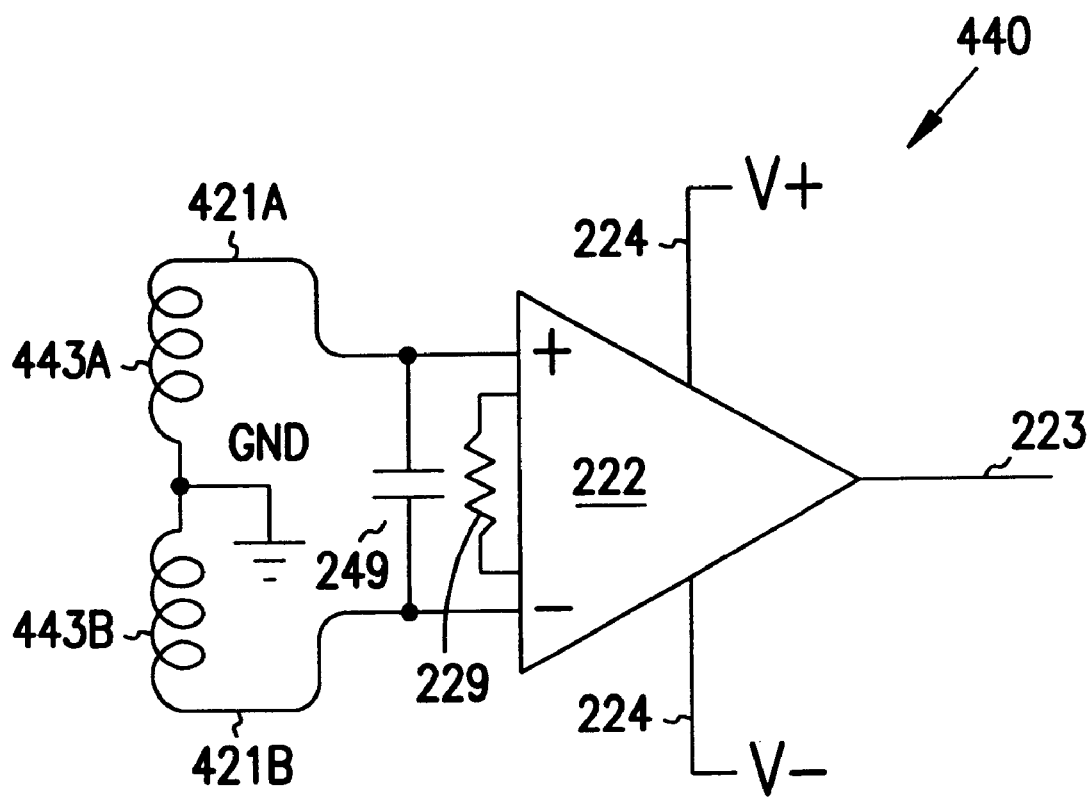
FIG. 4C shows a circuit diagram of sensor unit 440.

FIG. 4C shows a circuit diagram of sensor unit 440. In this embodiment, sensor coils 443A and 443B are differentially wired and the resultant differential signals 421A and 421B are input to differential amplifier 222. In one embodiment gain resister 229 provides stabilization and sets the gain for op amp 222, and plus and minus voltage power connections 224 are provided for op amp 222. As above, this preamplifier is shielded within probe 200.

In other embodiments, various combinations of the single excitation unit 230A of FIG. 3A or the rotating excitation unit 230B of FIG. 3B or the traveling wave excitation unit 230C of FIGS. 3C and 3D are combined in a probe with any one of the sensor units shown in FIG. 2A or 4A.

Figure 5A:
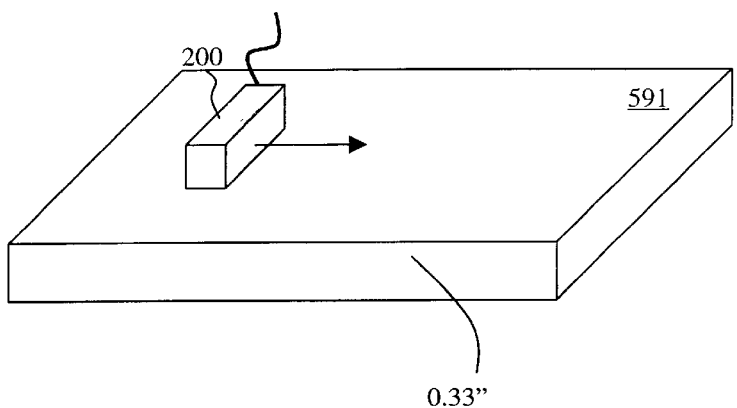
FIG. 5A shows the configuration of a scanning operation for a defect-free aluminum-sheet case.

FIG. 5A shows the configuration of an exemplary scanning operation for a defect-free aluminum-sheet case. In this example, probe 200 (such as that shown and described in FIG. 2A) is placed face down on a sheet 591 of clear (defect free) aluminum 0.33 inches thick (about 8.4 millimeters), and moved from left to right. Plot line 510A of FIG. 5D shows an imaginary-signal vs. displacement graph of the output signal for this operation. Plot line 512A of FIG. 5E shows an imaginary-signal vs. real-signal graph of the output signal for this operation.

Figure 5B:
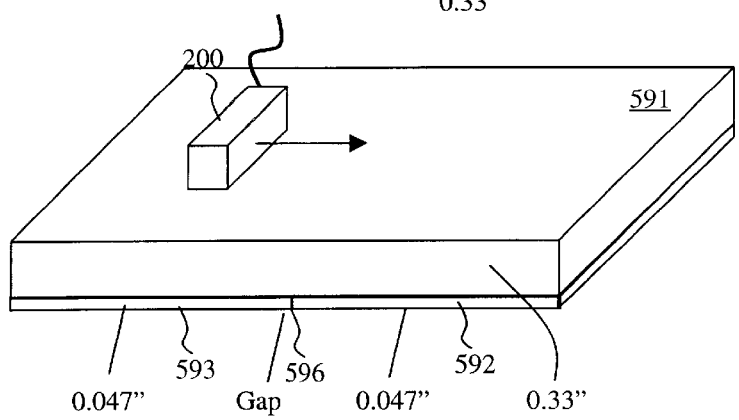
FIG. 5B shows the configuration of a scanning operation for a discontinuity defect behind a 0.33-inch clear aluminum-sheet.

FIG. 5B shows the configuration of a scanning operation for a discontinuity defect behind a 0.33-inch clear aluminum-sheet. In this example, probe 200 is again placed face down and moved from left to right. The sample includes sheet 591 of clear aluminum 0.33 inches thick (about 8.4 millimeters), under which are two aluminum sheets 592 and 593 (each 0.047 inch (1.19 mm) thick) butted tightly against one another to leave a "gap" 596 along the line where they meet. Plot line 510B of FIG. 5D shows an imaginary-signal vs. displacement graph of the output signal for this operation. Plot line 512B of FIG. 5E shows an imaginary-signal vs. real-signal graph of the output signal for this operation.

Figure 5C:
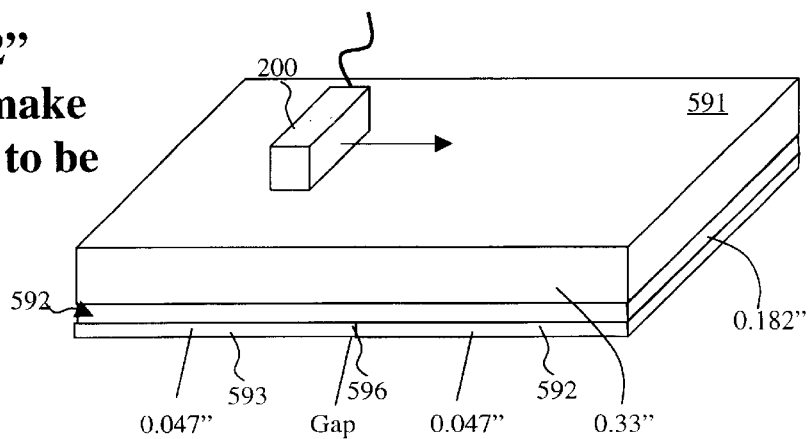
FIG. 5C shows the configuration of a scanning operation for a discontinuity-defect behind stacked 0.33-inch and 0.182-inch clear aluminum sheets.
Figure 5D:
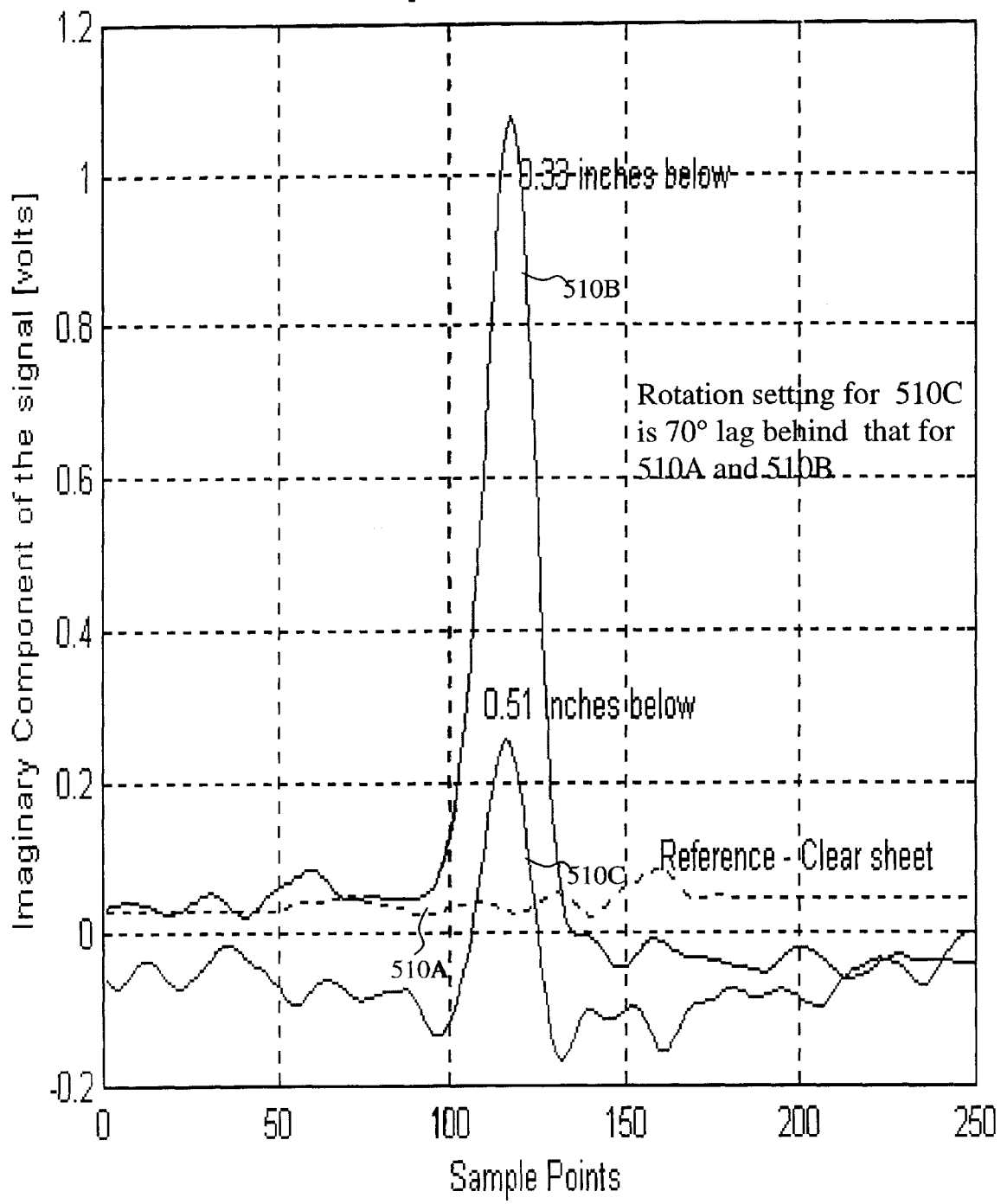
FIG. 5D shows an imaginary-signal vs. displacement graph of the three results of the scanning operations of FIGS. 5A, 5B, and 5C.
Figure 5E:
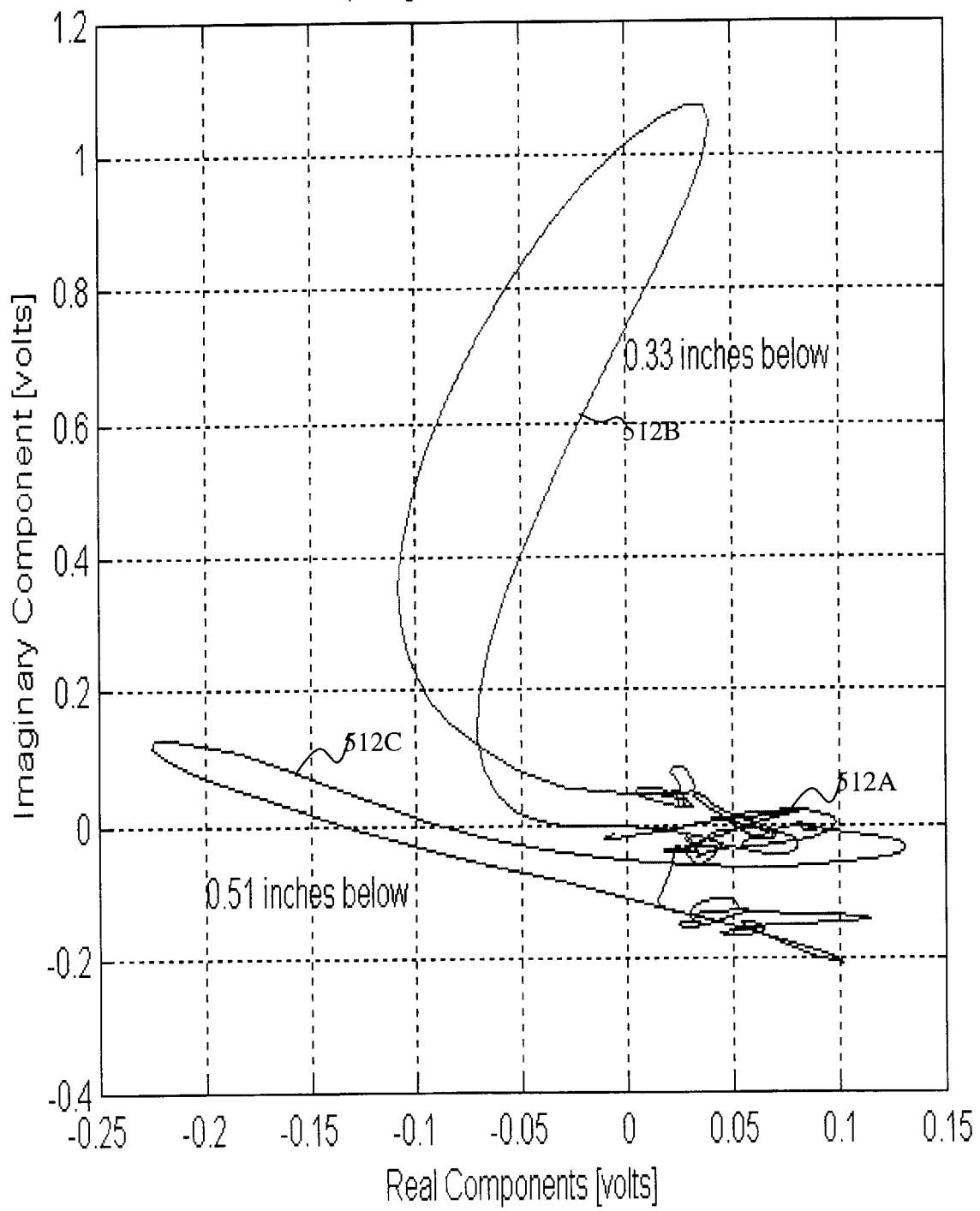
FIG. 5E shows an imaginary-signal vs. real-signal graph of the three results of the scanning operations of FIGS. 5A, 5B, and 5C.

FIG. 5C shows the configuration of a scanning operation for a discontinuity-defect behind stacked 0.33-inch and 0.182-inch clear aluminum-sheets. In this example, probe 200 is again placed face down and moved from left to right. The sample includes sheet 591 of clear aluminum 0.33 inches thick (about 8.4 millimeters), under which is sheet 594 of clear aluminum 0.182 inches thick (about 2.3 millimeters), under which are two aluminum sheets 592 and 593 (each 0.047 inch (1.19 mm) thick) butted tightly against one another to leave a "gap" 596 along the line where they meet. Plot line 510C of FIG. 5D shows an imaginary-signal vs. displacement graph of the output signal for this operation. Plot line 512C of FIG. 5E shows an imaginary-signal vs. real-signal graph of the output signal for this operation.

FIG. 5D shows an imaginary-signal vs. displacement graph of the three plot results 510A, 510B, and 510C of the scanning operations of FIGS. 5A, 5B, and 5C, respectively. The extraordinary spike in plot 510B and the well-defined spike in plot 510C clearly show the capability of detecting internal discontinuities and cracks, even when behind a considerably thickness of one or more defect-free aluminum sheets.

FIG. 5E shows an imaginary-signal vs. real-signal graph of the three plot results 512A, 512B, and 512C of the scanning operations of FIGS. 5A, 5B, and 5C, respectively. The extraordinary loop in plot 512B and the well-defined loop in plot 512C (especially as compared to the localized plot 512A) clearly show the enhanced capability of detecting internal discontinuities and cracks by displaying the real versus imaginary components.

Figure 6A:
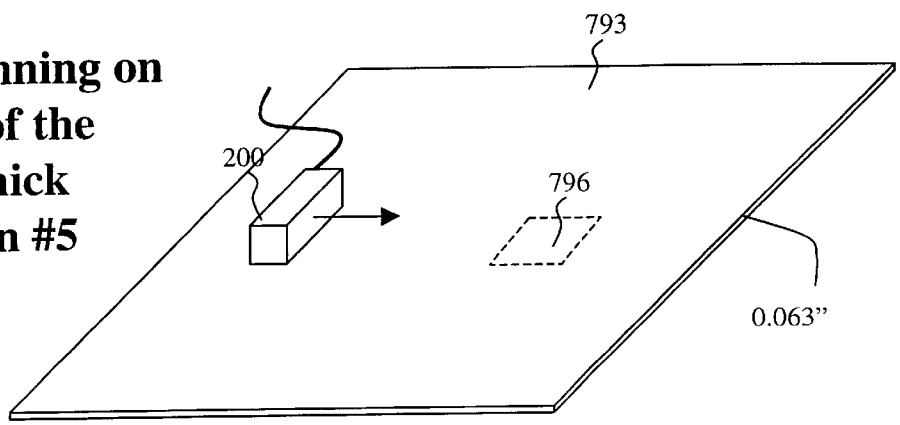
FIG. 6A shows the configuration of a scanning operation for a 10% thinning defect at the back side of a 0.063-inch aluminum sheet.
Figure 6A:
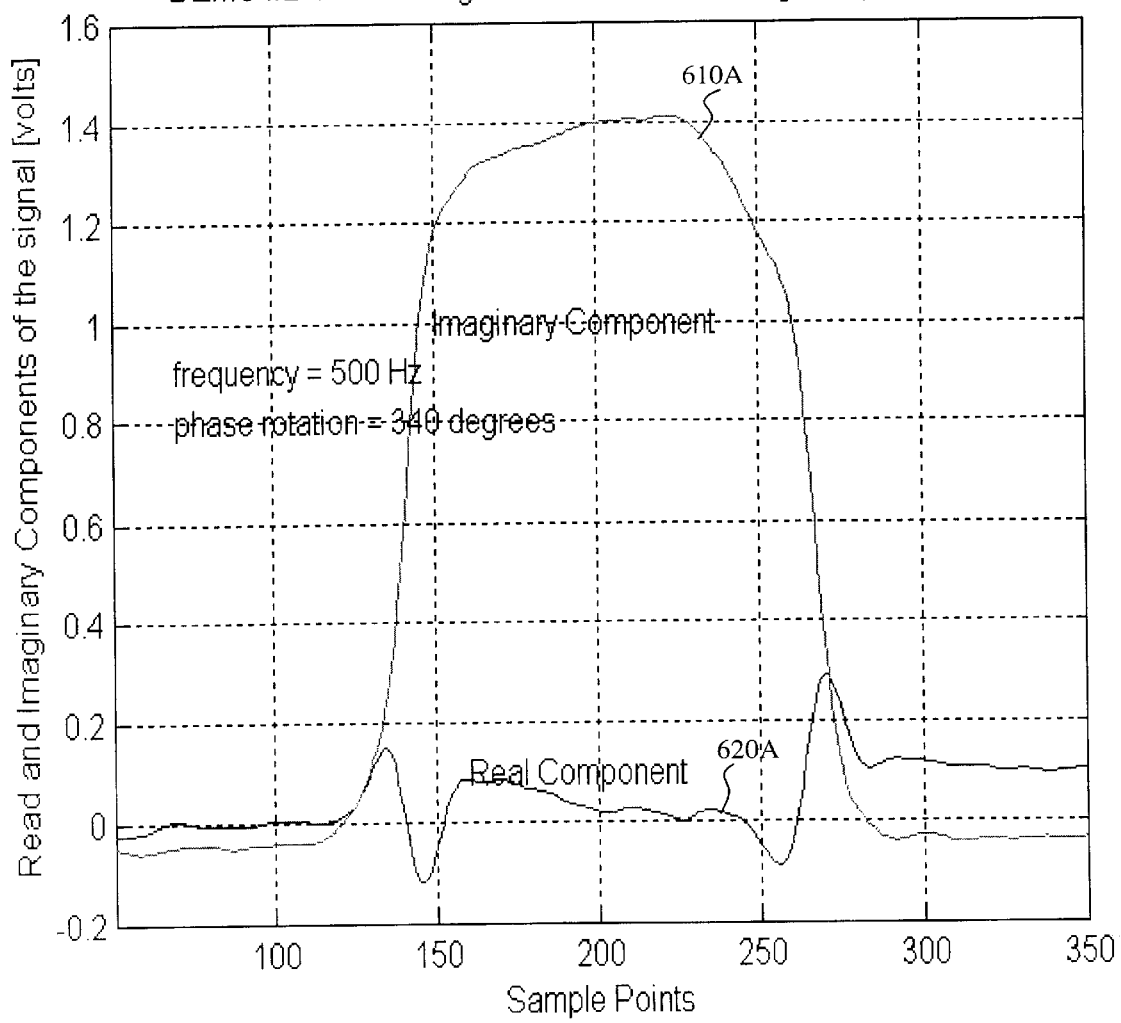

FIG. 6A shows the configuration of a scanning operation for a 10% thinning defect 796 at the backside of a 0.063-inch aluminum-sheet 793. In this example (as well as for FIGS. 6B and 6C), probe 200 is again placed face down and moved from left to right, with an excitation frequency of 500 hertz. For this example, a plot phase rotation of about 340 degrees is used (see above description of rotator 540 of FIG. 1B). The sample includes sheet 593 of aluminum 0.063 inches thick (about 1.6 millimeters) which has an area 596 etched to a depth of about 10% of its thickness (the etched rectangle is about 0.16 mm deep) on the bottom side (the side opposite to probe 200). FIG. 6D shows an imaginary-signal vs. displacement graph 610A and real-signal vs. displacement graph 620A (showing a peak as the probe 200 crosses each edge of region 796) of the results of the scanning operation of FIG. 6A.

Figure 6B:
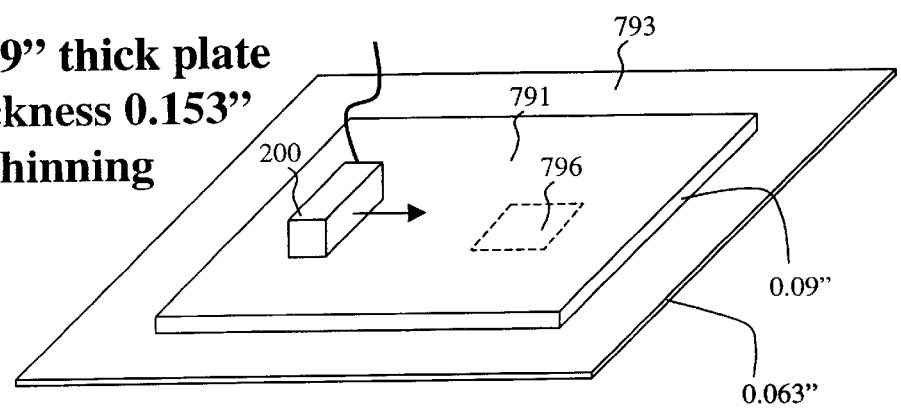
FIG. 6B shows the configuration of a scanning operation for the thinning defect of FIG. 6A beneath an additional 0.09-inch clear aluminum sheet.
Figure 6B:
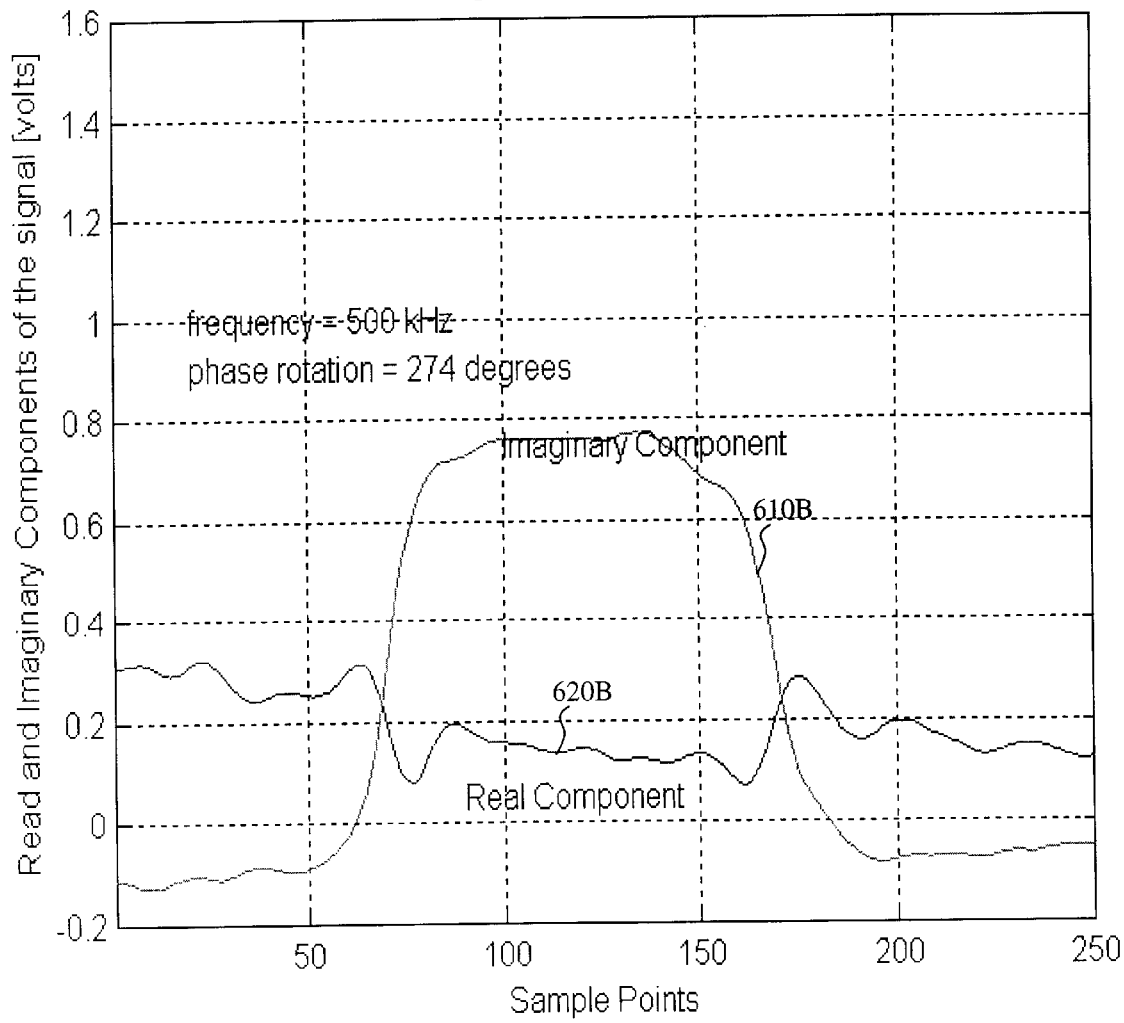

FIG. 6B shows the configuration of a scanning operation for the thinning defect 796 on sheet 793 of FIG. 6A, beneath an additional 0.09-inch (about 2.3 mm) clear aluminum-sheet 792. For this example, an excitation frequency of 500 hertz and a plot phase rotation of about 274 degrees is used (see above description of rotator 540 of FIG. 1B). In some embodiments, this phase rotation amount is empirically selected to "balance" the instrument to best show imaginary or real component changes due to defects and minimize noise signals contained in the same component. The thinned area 796 has a depth of about 4.1% of the total thickness of this sample. FIG. 6E shows an imaginary-signal vs. displacement graph 610B and real-signal vs. displacement graph 620B of the results of the scanning operation of FIG. 6B. The defect is clearly detectable under this added sheet of aluminum.

Figure 6C:
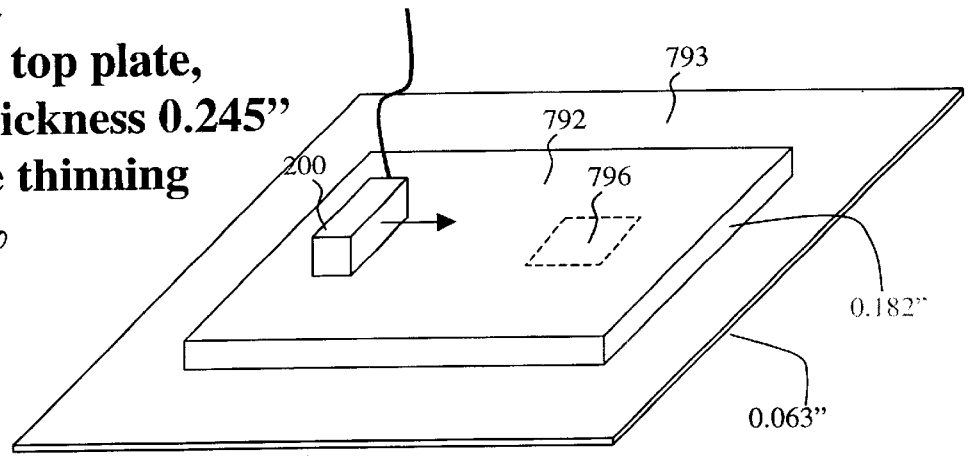
FIG. 6C shows the configuration of a scanning operation for the thinning defect of FIG. 6A beneath an additional 0.182-inch clear aluminum sheet.
Figure 6C:
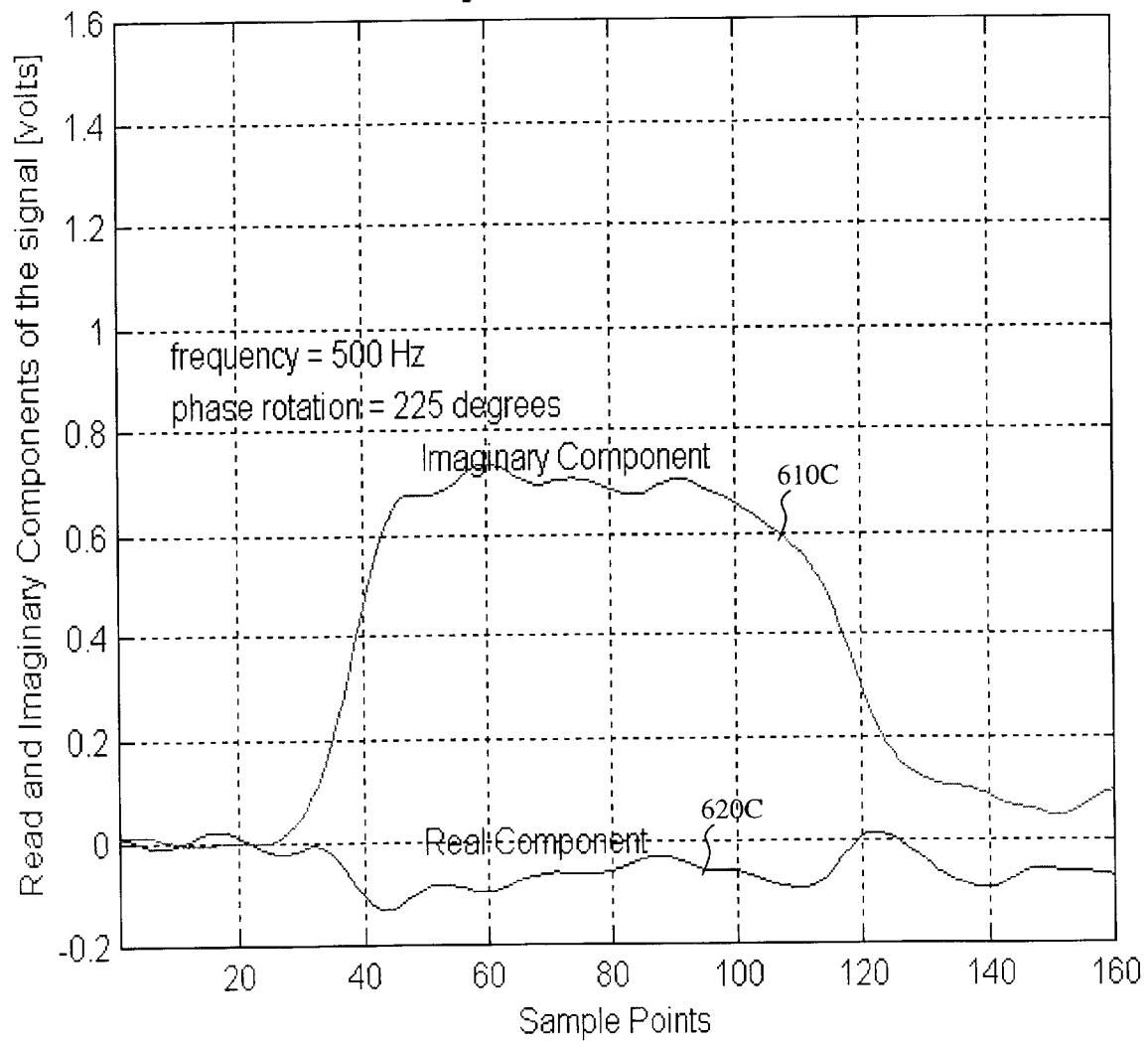

FIG. 6C shows the configuration of a scanning operation for the thinning defect of FIG. 6A beneath an additional 0.182-inch (about 4.6 mm) clear aluminum-sheet 791. The thinned area has a depth of about 2.57% of the total thickness of this sample. For this example, an excitation frequency of 500 hertz and a plot phase rotation of about 225 degrees is used (see above description of rotator 540 of FIG. 1B). FIG. 6F shows an imaginary-signal vs. displacement graph 610C and real-signal vs. displacement graph 620C of the results of the scanning operation of FIG. 6C. The defect is clearly detectable under this even thicker added sheet of aluminum.

Figure 6G:
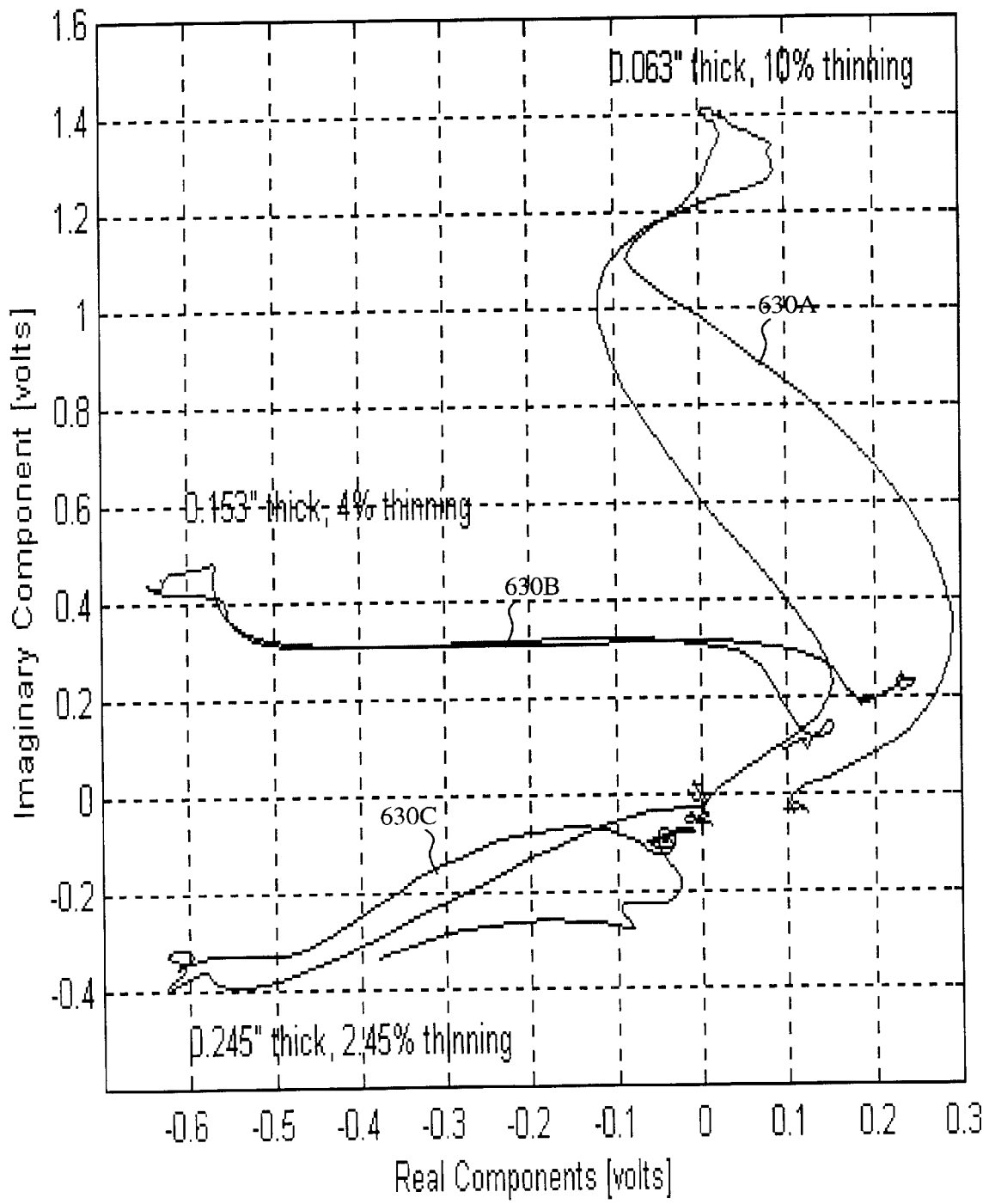
FIG. 6G shows an imaginary-signal vs. real-signal graph of the three results of the scanning operations of FIGS. 6A, 6B, and 6C.

FIG. 6G shows an imaginary-signal vs. real-signal graph of the three results 630A, 630B, and 630C of the scanning operations of FIGS. 6A, 6B, and 6C, respectively. This mode of signal analysis (i.e., having a computer pattern-recognition program analyze the real vs. imaginary signals) and/or display presentation provide enhanced flaw detection for some embodiments.

Figure 7A:
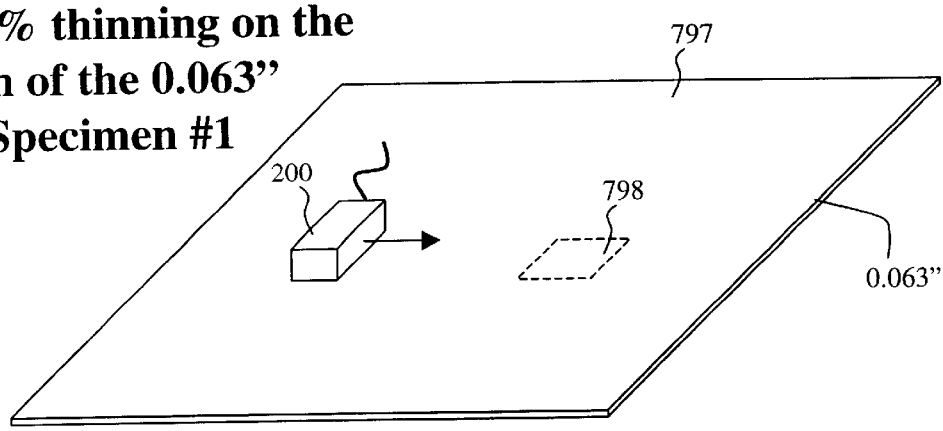
FIG. 7A shows the configuration of a scanning operation for a 3.17% thinning defect at the back side of a 0.063-inch aluminum-sheet.
Figure 7A:
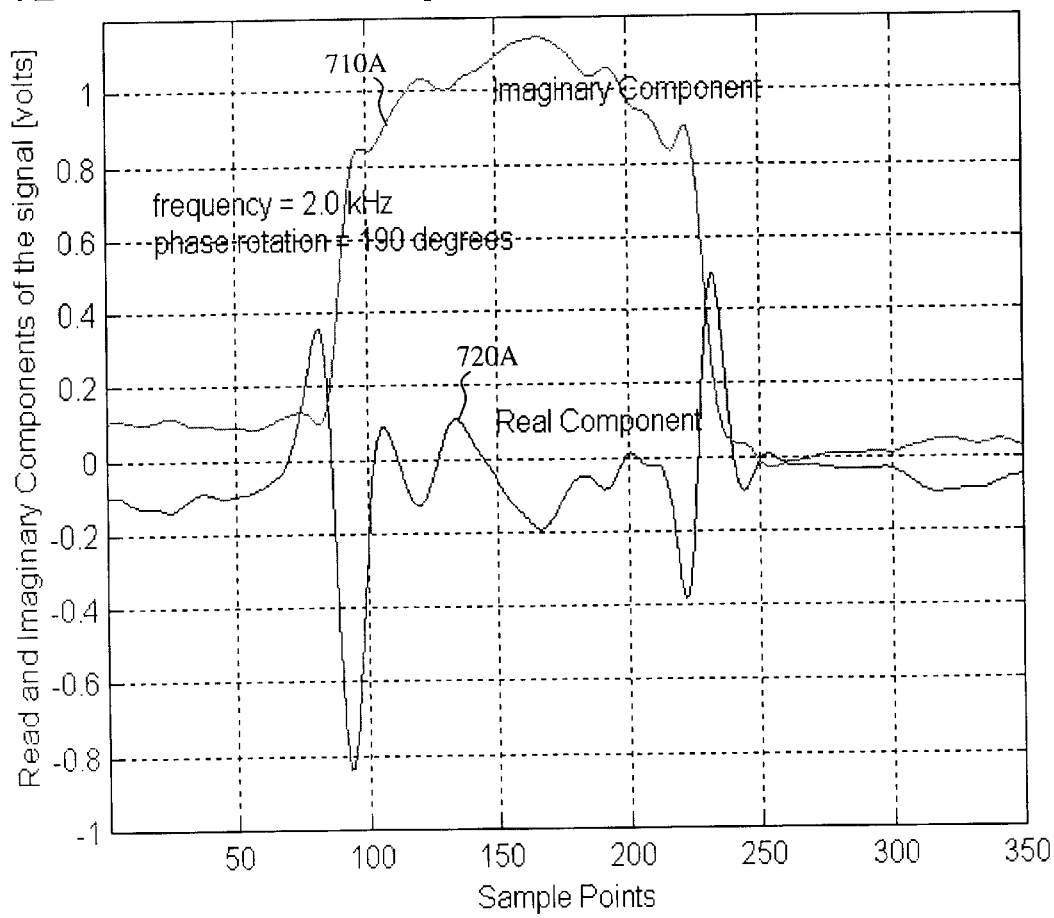

FIG. 7A shows the configuration of a scanning operation for a 3.17% thinning defect at the backside of a 0.063-inch aluminum-sheet. In this example (as well as for FIGS. 7B and 7C), probe 200 is again placed face down and moved from left to right. For this example, an excitation frequency of 2000 hertz and a plot phase rotation of about 190 degrees is used (see above description of rotator 540 of FIG. 1B). A higher frequency (relative to the frequency used for FIGS. 6A–6C) is used here for better detection of relatively smaller thickness variations (only about 3.17% thinning), as well as for thinner samples in other cases. The sample includes sheet 797 of aluminum 0.063 inches thick (about 1.6 millimeters) which has an area 798 etched to a depth of about 3.17% of its thickness (the etched rectangle is about 0.002 inches= 0.05 mm deep) on the bottom side (the side opposite to probe 200). FIG. 7D shows an imaginary-signal vs. displacement graph 710A and real-signal vs. displacement graph 720A (showing a strong peak, due to the 2000 hertz excitation frequency, as the probe 200 crosses each edge of region 796) of the results of the scanning operation of FIG. 7A.

Figure 7B:
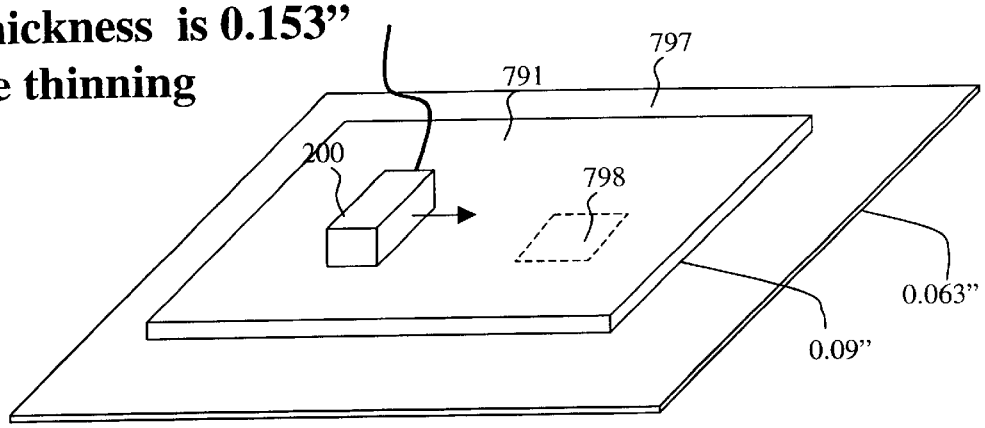
FIG. 7B shows the configuration of a scanning operation for the thinning defect of FIG. 7A beneath an additional 0.09-inch clear aluminum-sheet.
Figure 7E:
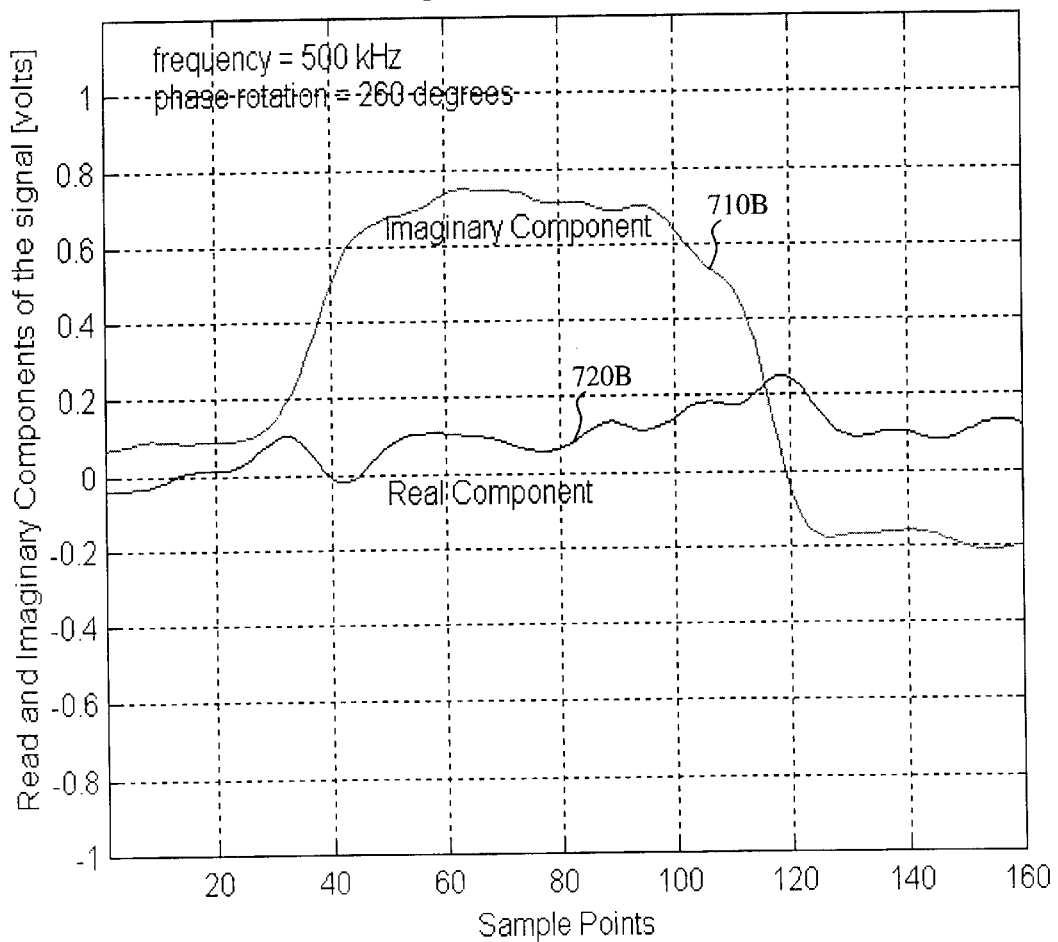
FIG. 7E shows an imaginary&real-signal vs. displacement graph of the results of the scanning operation of FIG. 7B.

FIG. 7B shows the configuration of a scanning operation for the thinning defect of FIG. 7A beneath an additional 0.09-inch clear aluminum-sheet. For this example, an excitation frequency of 500 hertz and a plot phase rotation of about 260 degrees is used (see above description of rotator 540 of FIG. 1B). The thinned area has a depth of about 1.32% of the total thickness of this sample. FIG. 7E shows an imaginary-signal vs. displacement graph 710B and real-signal vs. displacement graph 720B of the results of the scanning operation of FIG. 7B. The defect is detectable under this added sheet of aluminum.

Figure 7C:
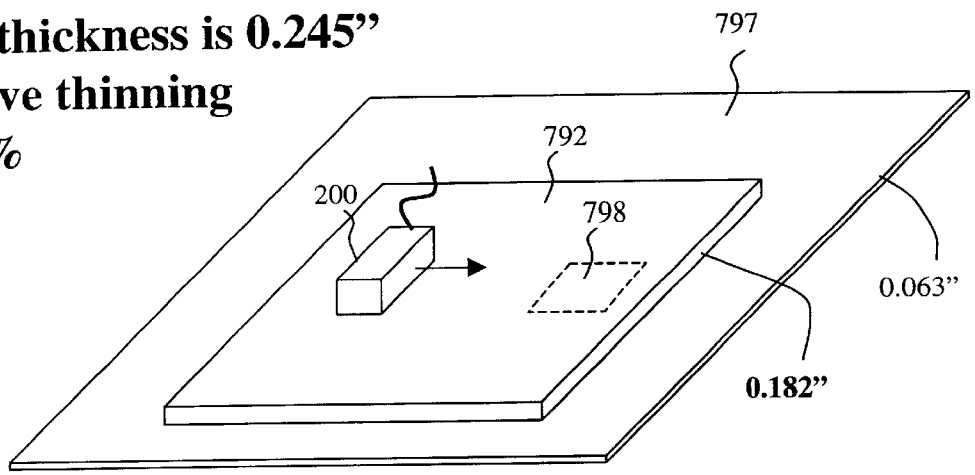
FIG. 7C shows the configuration of a scanning operation for the thinning defect of FIG. 7A beneath an additional 0.182-inch clear aluminum-sheet.
Figure 7C:
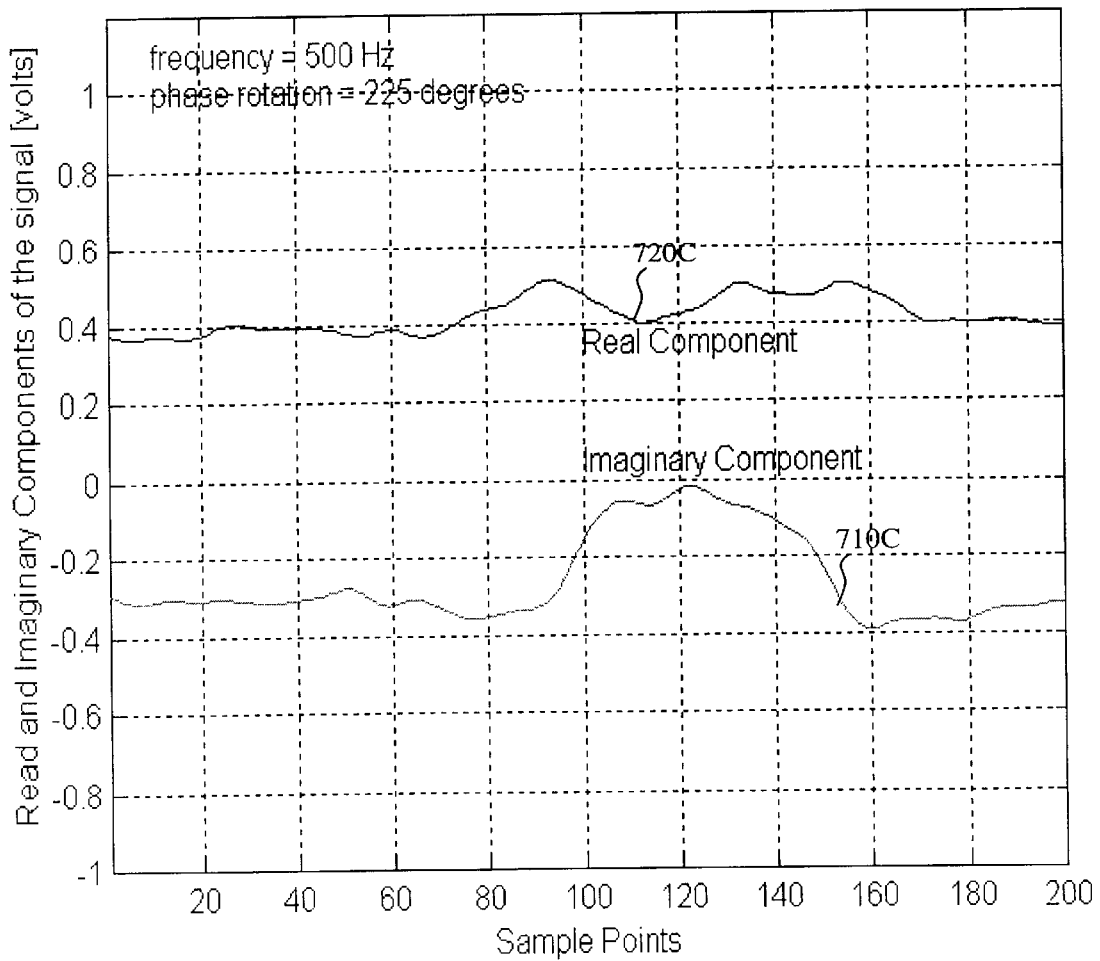

FIG. 7C shows the configuration of a scanning operation for the thinning defect of FIG. 7A beneath an additional 0.182-inch clear aluminum-sheet. For this example, an excitation frequency of 500 hertz and a plot phase rotation of about 225 degrees is used (see above description of rotator 540 of FIG. 1B). FIG. 7F shows an imaginary-signal vs. displacement graph 710C and real-signal vs. displacement graph 720C of the results of the scanning operation of FIG. 7C. The defect is still detectable under this even thicker added sheet of aluminum.

Figure 7G:
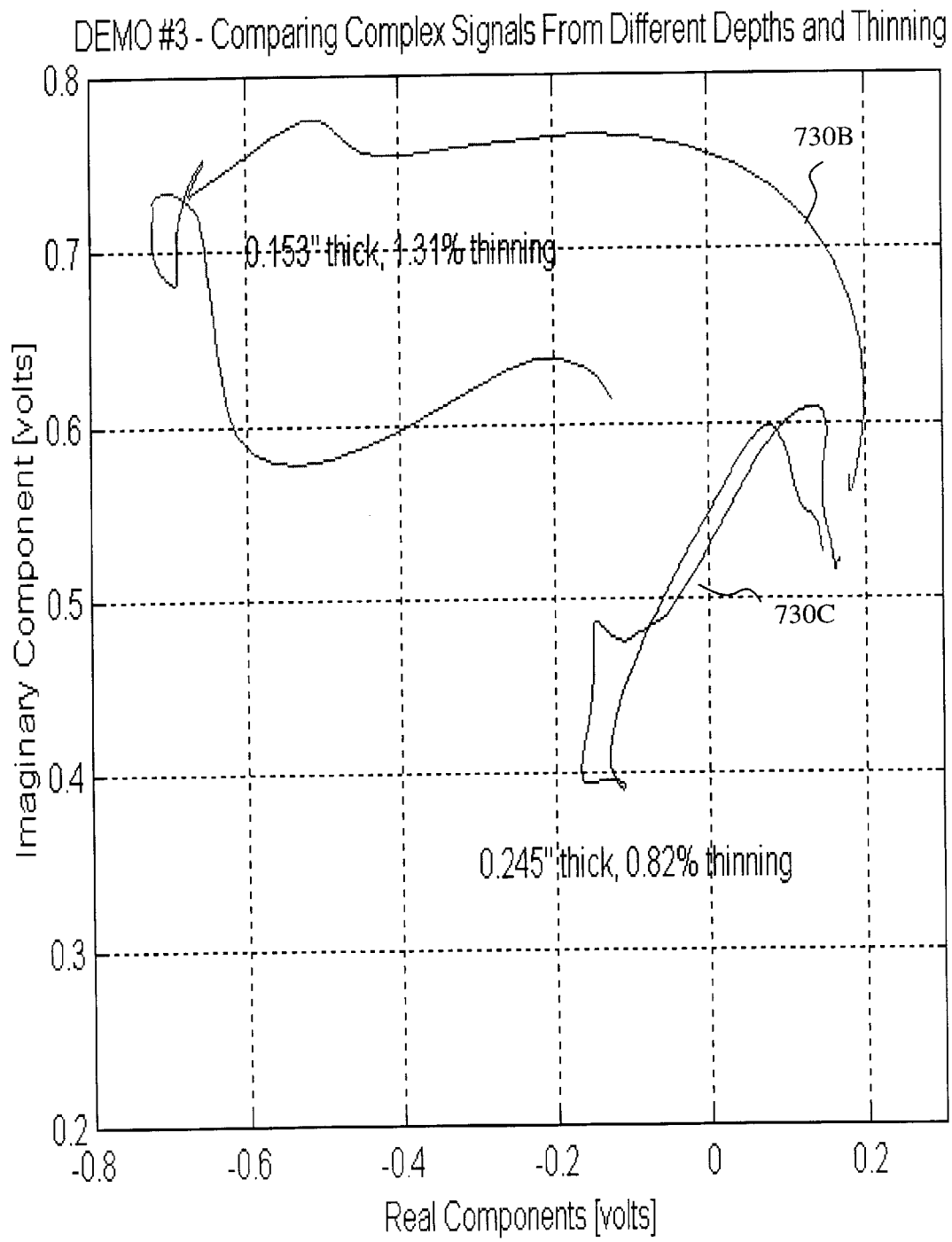
FIG. 7G shows an imaginary-signal vs. real-signal graph of the two results of the scanning operations of FIGS. 7B and 7C.

FIG. 7G shows an imaginary-signal vs. real-signal graph of two results of the scanning operations of FIGS. 7B and 7C. This mode of signal analysis (i.e., having a computer pattern-recognition program analyze the real vs. imaginary signals) and/or display presentation provide enhanced flaw detection for some embodiments.

FIG. 8A shows the configuration of a riveted sample 810 having 10 rivets and two defects. Sample 810 includes two sheets of aluminum (sheet 811 which is 0.27 inches=6.86 mm thick, and sheet 812 which is 0.176 inches=4.47 mm thick) held together with ten fasteners, nine of which are titanium, and one of which (rivet 825) is steel (considered to be one type of defect, since this may comprise the wrong rivet material for certain applications). Sheet 812 also has a small fatigue crack made radially outward to a length of 0.031 inches=0.79 mm from rivet 828 (considered to be a second type of defect).

FIG. 8B shows the configuration of a scanning operation for the sample of FIG. 8A. Probe 200 is scanned, face down, right to left across the sample 810, as shown in FIG. 8B. The fatigue crack next to rivet 828 is in the sheet 812 that is on the side opposite to probe 200 when the hand-held scanning operation is performed.

Figure 8C:
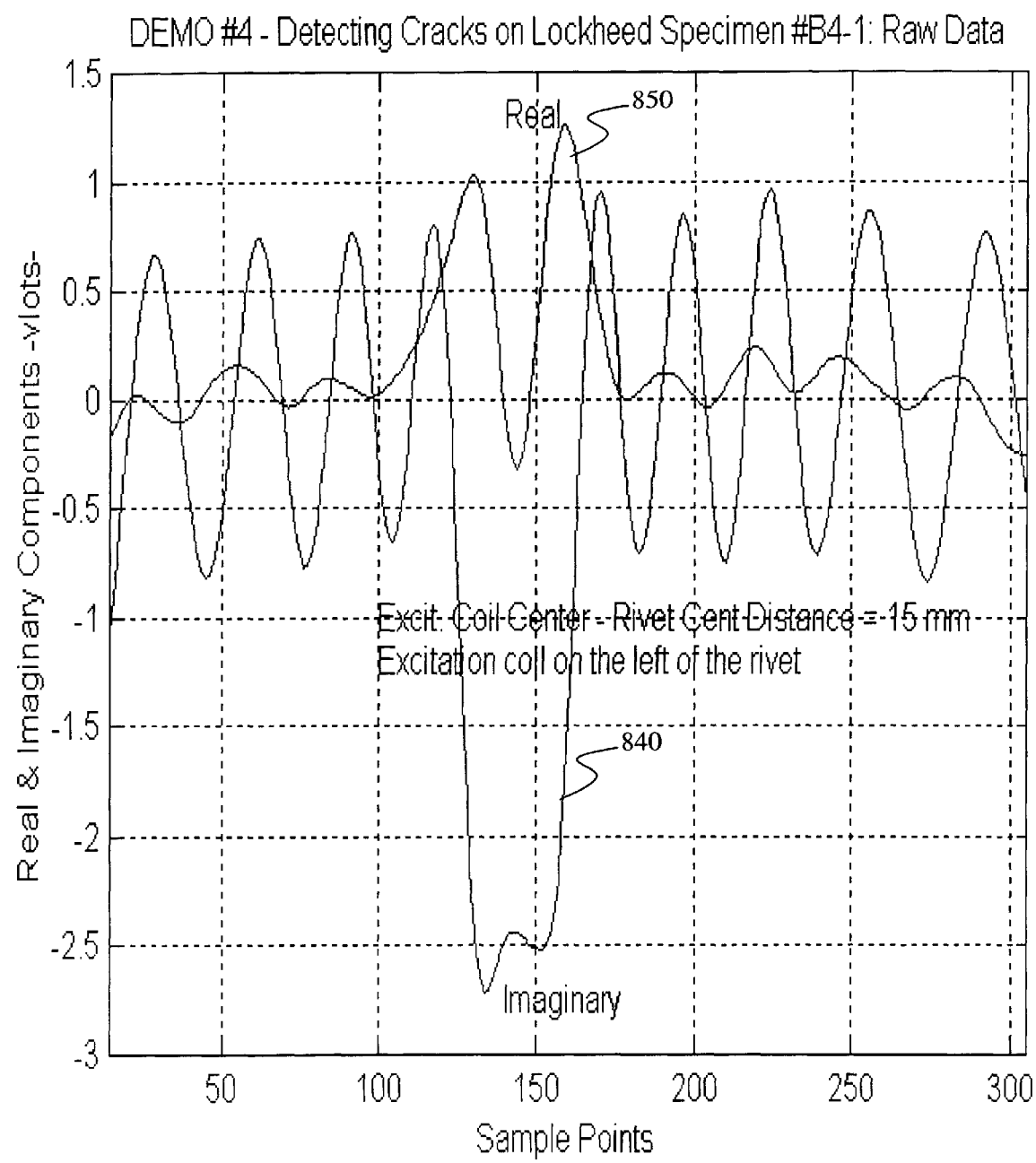
FIG. 8C shows an imaginary&real-signal vs. displacement graph of the results of the scanning operation of FIG. 8A.

FIG. 8C shows an imaginary-signal vs. displacement graph 840 and real-signal vs. displacement graph 850 of the results of the scanning operation of FIG. 8B. The excitation coil 230 was about 15 mm from the rivet centers. The steel-rivet defect is clearly detectable on imaginary-component plot 840, and somewhat on real component plot 850, and each titanium rivet is also detected, however the small crack from rivet 828 is not clearly identifiable here.

FIG. 8D shows an imaginary-signal vs. real-signal graph 880 of the results of the scanning operation of FIG. 8A at 250 hertz. The steel-rivet defect is also clearly detectable on imaginary-real plot 880 at loop 885, as well as at portion 886 where the probe is over neighboring titanium rivets, and the small crack from rivet 828 is somewhat identifiable here as loop 888 which is to the right and higher as compared to the loops for the other rivets.

Figure 8E:
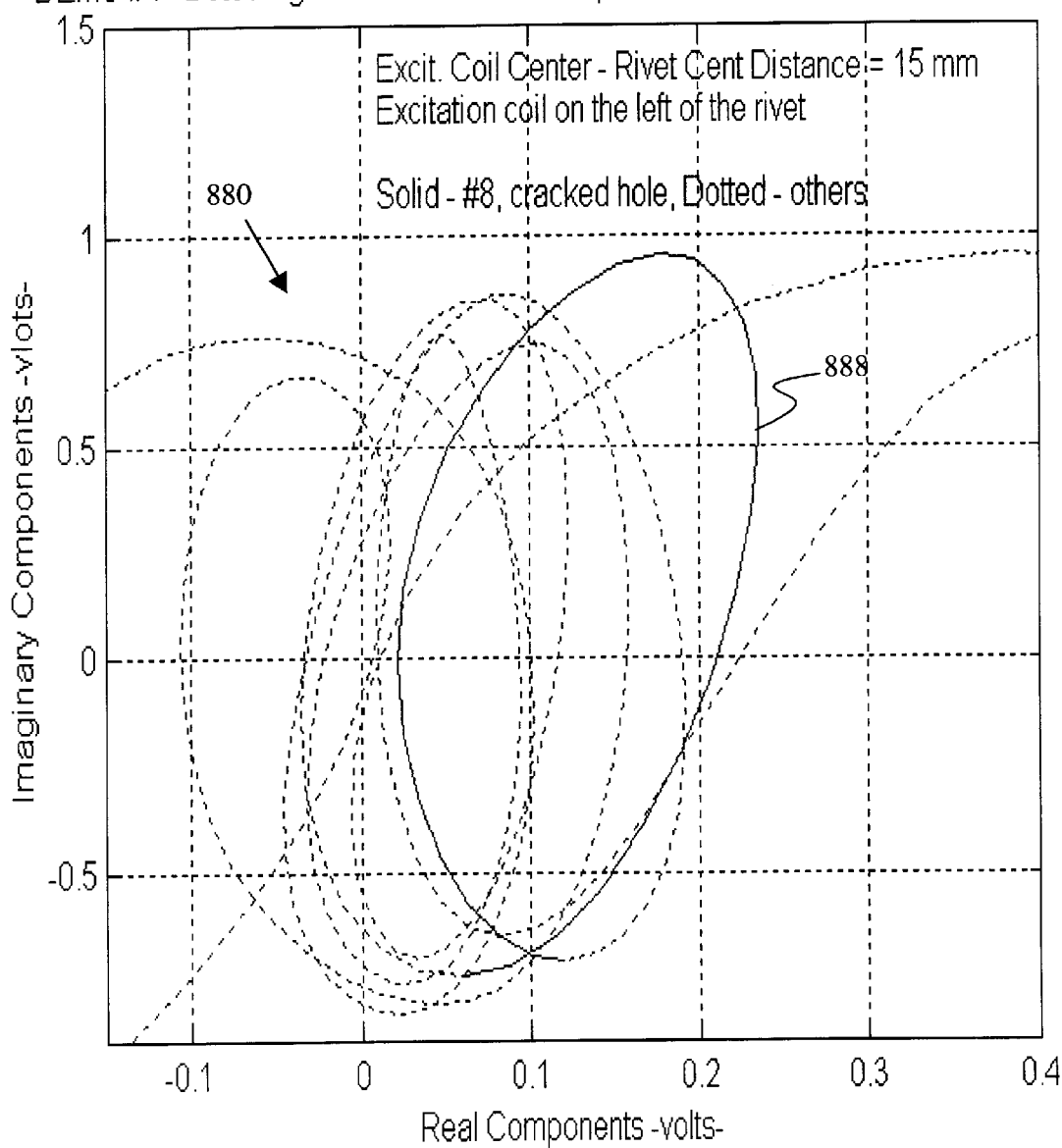
FIG. 8E shows a close-up of a portion of the graph of FIG. 8D.

FIG. 8E shows a close-up of a portion of the graph of FIG. 8D. Here, the small crack from rivet 828 is more identifiable here as loop 888 that is to the right and higher as compared to the loops for the other rivets.

Figure 8F:
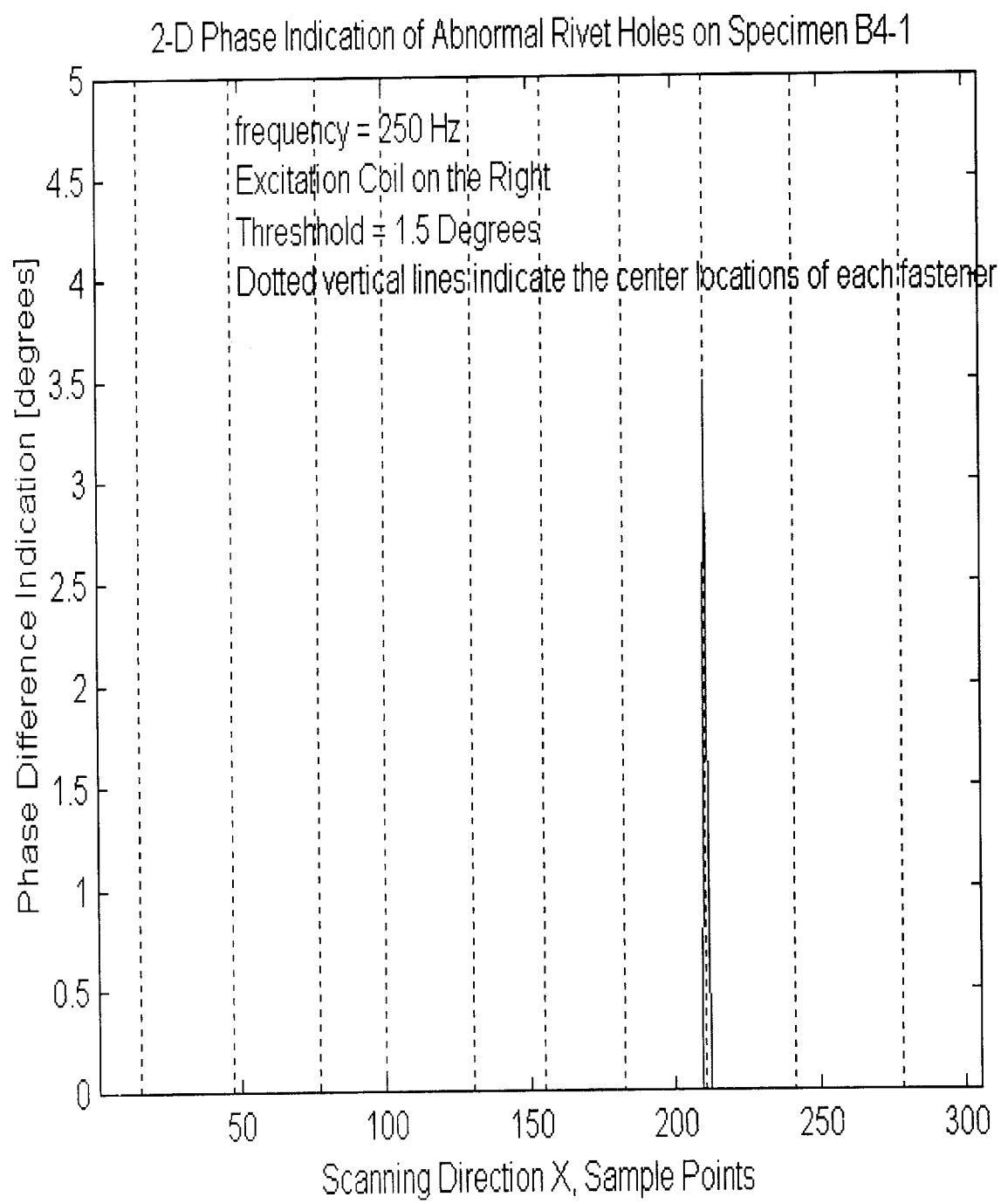
FIG. 8F shows a phase-difference vs. displacement graph of the results of the scanning operation of FIG. 8A at 250 hertz.

FIG. 8F shows the after-signal-processing results of the scanning operation of FIG. 8A at 250 hertz. The signal processing uses a phase-difference-based algorithm. The dotted vertical lines show the locations of the ten rivets, 821 through 830 left-to-right. Here, the small crack from rivet 828 is even more identifiable here as the peak phase difference (of about 3.5 degrees) at about displacement 210. It is the unique abnormal signal identified by the algorithm with a given threshold of 1.5 degrees.

Figure 8G:
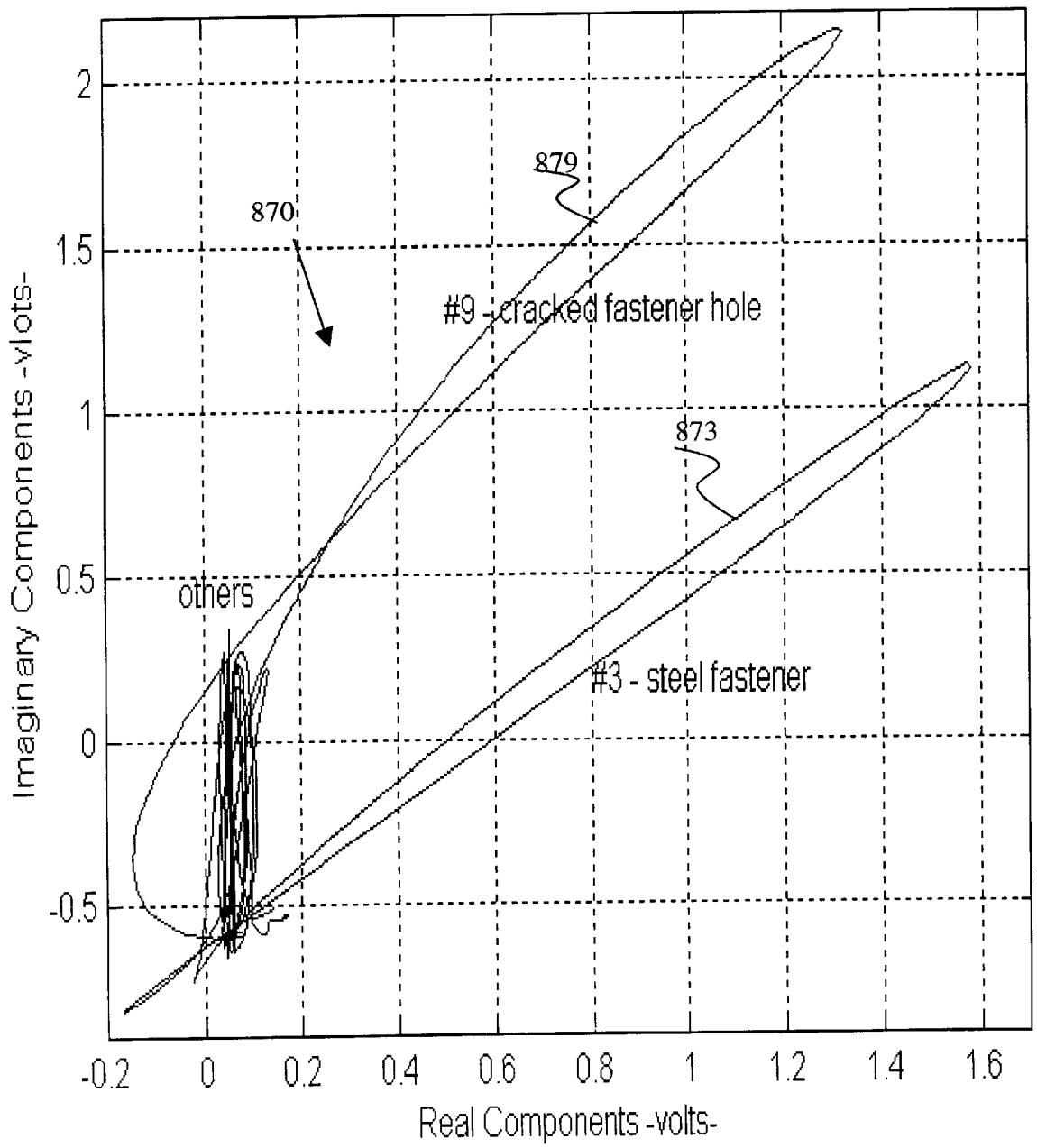
FIG. 8G shows an imaginary-signal vs. real-signal graph of the results of the scanning operation of FIG. 8A at 3000 hertz.

FIG. 8G shows an imaginary-signal vs. real-signal graph 870 of the results of a scanning operation similar to that of FIG. 8A at 3000 hertz. Here, a different sample is used, having a steel fastener at the number three hole and a cracked fastener hole on the number nine hole. At this higher frequency, both the defect and the steel fastener are clearly shown, with loop 879 due to the cracked fastener hole, and loop 873 due to the steel fastener, while other non-defect fasteners obtain confined small loops on the lower left of the plot 870.

Figure 8H:
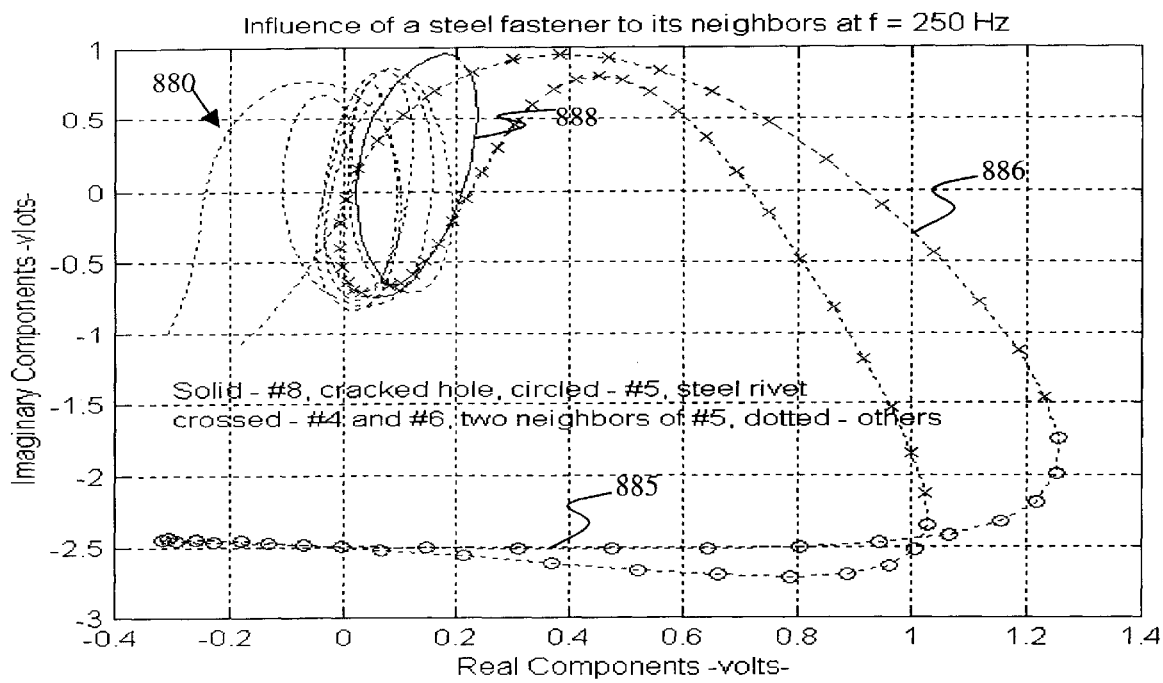
FIG. 8H shows another view of the graph of FIG. 8D at 250 hertz for side-by-side comparison to the graph of FIG. 8I.
Figure 8I:
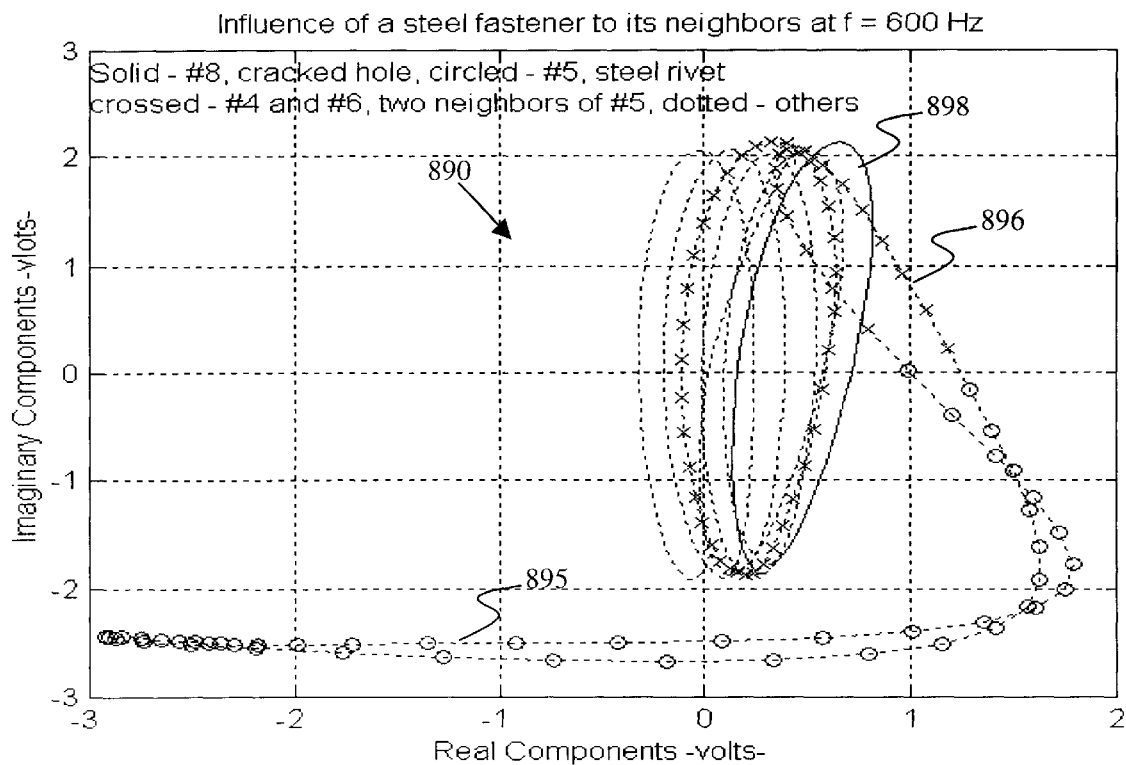
FIG. 8I shows an imaginary-signal vs. real-signal graph of the results of the scanning operation of FIG. 8A at 600 hertz.

FIG. 8H shows another view of the graph of FIG. 8D at 250 hertz for side-by-side comparison to the graph of FIG. 8I. Loop portion 885 shows the steel fastener 825, and loop portion 888 shows the crack next to fastener 828. Loop 886 shows the signals from fasteners 824 and 826 that are severely distorted by the influence from the steel fastener 825.

FIG. 8I shows an imaginary-signal vs. real-signal graph of the results of the scanning operation of FIG. 8A at 600 hertz. Loop portion 895 shows the steel fastener 825, and loop portion 898 shows the crack next to fastener 828, measured at the higher frequency. Loop 896 shows the signals from fasteners 824 and 826. Comparing it with Loop 886 in FIG. 8H, we can clearly see that the signal distortion due to the steel fastener 825 is minimized at 600 hertz. This shows the possibility of minimizing steel fastener influence to its neighboring signals by proper choice of excitation frequency.

Figure 9B:
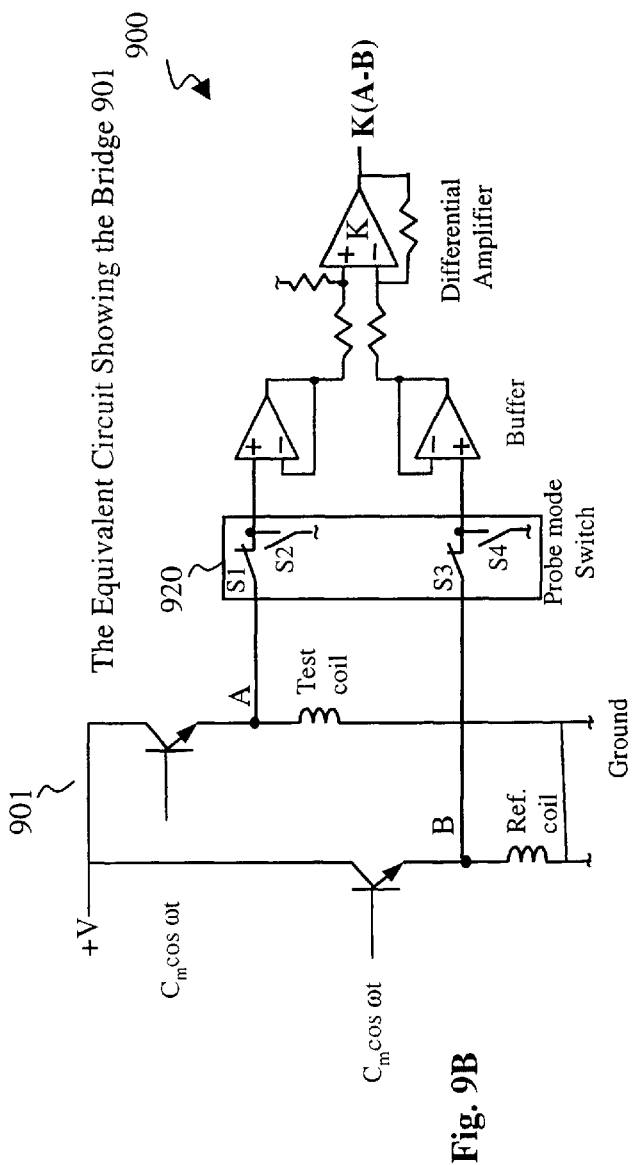
FIG. 9B shows a block diagram of the bridge circuit of FIG. 9A.

FIG. 9A shows a bridge circuit useful for driving probe 200 from driver 111. FIG. 9B shows a block diagram of the bridge circuit of FIG. 9A. In this embodiment, two identical excitation coils 230 are driven in a differential bridge mode, rather than using the excitation coil 230/sensor coil 240 configuration of FIG. 2B. Excitation signal $C_m \cos\omega t$ feeds buffer op amps 910 and 912, which drive two excitation coils 230 such as shown in FIG. 2B (in the FIG. 9A, one coil 230 is labeled test coil 911 and the other is labeled reference coil 913). Rather than sensing the signal from a separate sensor coil 240 or GMR sensor, the bridge circuit detects the differential signal in the bridge of the two excitation coils 911 and 913. The output of the bridge 901 passes through mode switches 920, wherein switches S1 and S3 are closed and switches S2 and S4 are open to operate in differential mode, and switches S1 and S4 are closed and switches S2 and S3 are open to operate in single-ended (absolute) mode. The output of the switches 920 ($A_m \cos\omega t$ for one and $B_m \cos\omega t$ for the other, where $B_m=0$ if in single-ended (absolute) mode) go to separate respective non-inverting unity-gain buffers 930, and the output of buffers 930 serve as inputs to differential amplifier 940. In some embodiments, bridge circuit 520 and probe 200 of FIG. 1B are represented by coils 911 and 913, switches 920 and buffers 930 of FIG. 9A, and output drivers 514 and 515 of FIG. 1B are represented by buffer op amps 910 and 912 of FIG. 9A, and differential gain and pregain circuit 531 of FIG. 1B is represented by differential amplifier 940 of FIG. 9A. FIG. 9B is a schematic representation of the circuit 900, showing the buffer op amps 910 and 912 as emitter-follower transistors, to more clearly indicate the bridge circuit 901. The rest of FIG. 9B is identical to FIG. 9A.

Figure 10A:
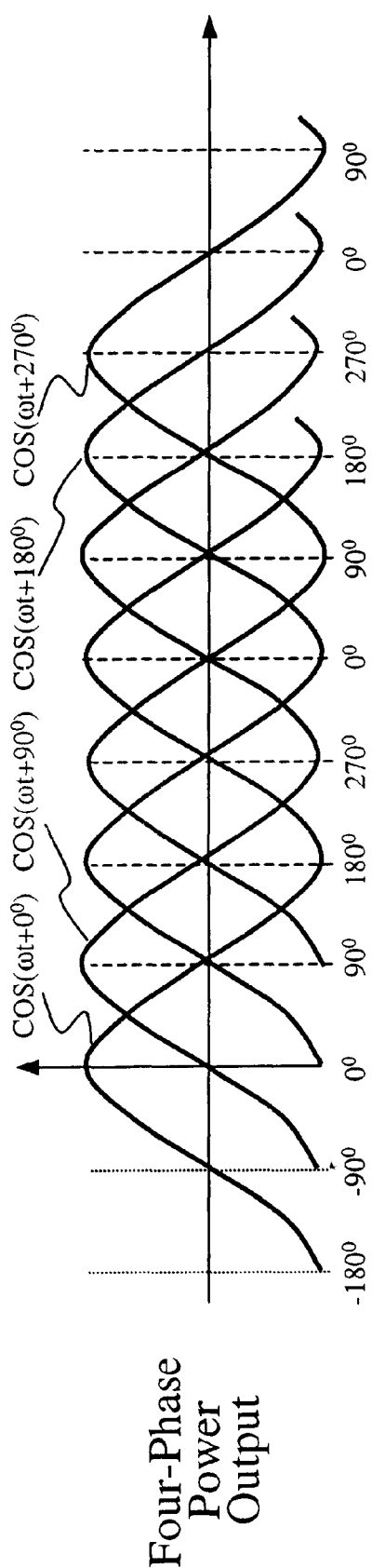
FIG. 10A shows the waveform of a four-phase excitation signal.
Figure 10B:
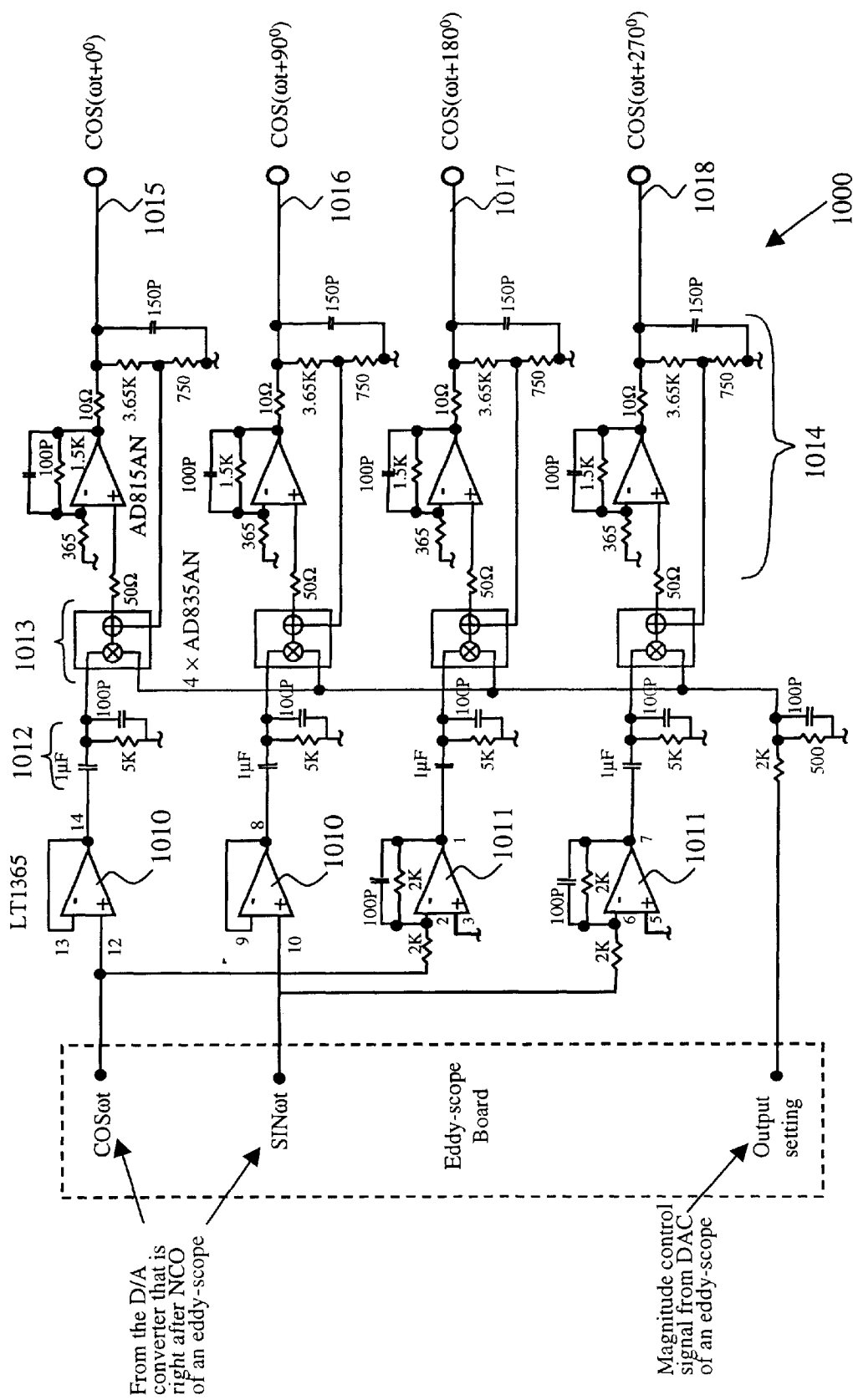
FIG. 10B shows a block diagram of a four-phase excitation signal circuit 1000.

FIG. 10A shows the waveform of a four-phase excitation signal such as produced by outputs 1015, 1016, 1017, and 1018 of FIG. 10B.

FIG. 10B shows a block diagram of a four-phase excitation signal circuit 1000. Circuit 100 includes a sine/cosine source (such as described above), wherein the $\cos\omega t$ and sinωt source provide the 0 degrees phase (for reference number 1015), and the 90 degrees phase (for reference number 1016), each coupled through non-inverting unity-gain amplifiers 1010, while the cosωt and sinωt source passed through inverting unity-gain amplifiers 1011 provide the 180 degree (for reference number 1017) and 270 degree (for reference number 1018) phases respectively. In some embodiments, amplifiers 1010 and 1011 use LT1365 op amps. In some embodiments, each signal is passed through band-pass filters 1012, magnitude-adjustment circuits 1013, and output driver amplifiers 1014.

Conclusion

One aspect of the present invention provides a method of transducing magnetic signals indicative of a flaw in a conducting object. This method includes shielding an excitation coil 233 on substantially all sides except an emission face 250, transmitting an alternating magnetic signal to the conducting object 90 from the shielded excitation coil 233, such that the alternating magnetic signal is modified by the conducting object 90, shielding a magnetic detector 243 within a probe 200 on substantially all sides except a reception face 250. The method also includes receiving the alternating magnetic signal as modified by the conducting object into the shielded magnetic detector 243, converting the received alternating magnetic signal into a first electrical signal 221 within the shielded magnetic detector, shielding a signal-conditioning circuit 220 within the probe on substantially all sides, providing electrical power 224 to the shielded signal-conditioning circuit 220 within the probe, amplifying the first electrical signal with the signal-conditioning circuit 220 to create a second electrical signal 223, and analyzing phase and amplitude components of the second electrical signal 223 to provide an indication of the flaw.

In some embodiments of the method, the shielding the excitation coil includes providing a cup-shaped copper shield 231 that surrounds a ring-shaped steel shield 237 that in turn surrounds an excitation coil 233 having a ferromagnetic core 232.

In some embodiments of the method, the shielding of the magnetic detector 243 includes providing a cup-shaped copper shield 241 that surrounds a steel flux-bypass shield 247 that in turn surrounds a receiver coil 243 having a ferromagnetic core 242.

In some such embodiments, the ferromagnetic core 242 of the magnetic detector is E-shaped, and the receiver coil 243 is mounted on a central prong of the E-shaped ferromagnetic core 242.

In some embodiments of the method, the shielding of the signal-conditioning circuit 220 includes providing an aluminum shield 210, 211 that surrounds the signal-conditioning circuit 220 on substantially all sides;

In some embodiments of the method, the transmitting of the alternating magnetic signal includes transmitting a rotating magnetic field.

In some embodiments of the method, the transmitting of the alternating magnetic signal includes transmitting a traveling magnetic field.

In some embodiments of the method, the receiving and the converting of the received alternating magnetic signal provides a differential first electrical signal.

Another aspect of the present invention provides an eddy-current probe system 100 for detecting a flaw (e.g., 68 or 67) in a conducting object 90. The probe 200 includes an excitation coil unit 230, a magnetic detector 240 within the probe 200, a signal-conditioning circuit 220 within the probe 200, and a signal channel 260. The excitation coil unit 230 is shielded on substantially all sides except an emission face 250 that transmits an alternating magnetic signal to the conducting object 90, such that the alternating magnetic signal is modified by the conducting object 90. The magnetic detector 240 within the probe 200 is also shielded on substantially all sides except a reception face 250, such that the alternating magnetic signal as modified by the conducting object 90 is received into the shielded magnetic detector 240 and converted into a first electrical signal 221. The signal-conditioning circuit 220 within the probe is shielded on substantially all sides and provided with electrical power 224. This circuit 220 amplifies the first electrical signal 221 to create a second electrical signal 223. The signal channel 260 then transmits the second electrical signal 223 to an instrument 110 for analyzing phase and amplitude components of the second electrical signal 223 to provide an indication of the flaw (e.g., 68, or 67).

In some embodiments, the system further includes an eddy-scope 110, operatively coupled to the signal channel 260, that receives the transmitted second electrical signal 223 and provides the analyzing phase and amplitude function for components of the second electrical signal 223, and that presents the indication 118 or 119 of the flaw (e.g., 68 or 67).

In some embodiments of the system 100, the excitation coil unit 230 includes a coil 233 having a ferromagnetic core 232, and is surrounded radially and axially by a cup-shaped first shield 231 that surrounds substantially all sides except the emission face 250.

In some embodiments of the system 100, the ferromagnetic core 232 of the excitation coil unit 230 is surrounded radially by a ring-shaped second shield 237, located inside the cup 283 of the first shield 231. In some such embodiments, the first shield 231 is substantially made of copper.

In some embodiments of the system 100, the magnetic detector 240 includes a coil 243 having a ferromagnetic core 242, and is surrounded radially and axially by a cup-shaped first shield 241 that surrounds substantially all sides except the emission face 250. In some such embodiments, the first shield 241 is substantially made of copper.

In some embodiments of the system 100, the magnetic detector 240 includes an E-shaped ferromagnetic core 242 having a coil 243 mounted around a central prong of the E-shaped ferromagnetic core 242, a C-shaped steel flux bypass structure 247 around and magnetically coupled to the E-shaped ferromagnetic core 242, and a copper shield 241 surrounding C-shaped steel flux bypass structure 247 and the E-shaped ferromagnetic core 242 on substantially all sides except the reception face 250.

In some embodiments of the system 100, the excitation coil unit 230 includes a coil 233 having a ferromagnetic core 232, and is surrounded radially and axially by a cup-shaped first shield 231 that surrounds substantially all sides except the emission face 250, wherein the ferromagnetic core 232 of the excitation coil unit 230 is surrounded radially by a ring-shaped second shield 237, located inside the cup of the first shield 231, wherein the first shield 231 is substantially made of copper, and wherein the magnetic detector includes an E-shaped ferromagnetic core 242 having a coil 243 mounted around a central prong of the E-shaped ferromagnetic core 242, a C-shaped steel flux bypass structure 247 around and magnetically coupled to the E-shaped ferromagnetic core 242, and a copper shield 241 surrounding C-shaped steel flux bypass structure 247 and the E-shaped ferromagnetic core 242 on substantially all sides except the reception face 250.

In some embodiments of the system 100, the excitation coil unit 230 includes a multiple-phase coil system having a ferromagnetic core, and the eddy scope 110 includes a multiple-phase excitation circuit 111 that generates a plurality of phases of excitation signal to the excitation coil unit 230.

Another aspect of the present invention provides an eddy-current probe system 100 for detecting a flaw in a conducting object 90. This the probe includes an excitation coil unit 230 within a probe 200 shielded on substantially all sides except an emission face that transmits an alternating magnetic signal to the conducting object 90, such that the alternating magnetic signal is modified by the conducting object 90, a magnetic detector 240 within the probe shielded on substantially all sides except a reception face 250, that receives the alternating magnetic signal as modified by the conducting object 90, and generates a first electrical signal, and shielded means within the probe, powered by an external electrical supply, for amplifying the first electrical signal.

Another aspect of the present invention provides a traveling-wave eddy-current probe system for detecting a flaw in a conducting object. The traveling-wave probe includes an excitation coil unit within the probe, the excitation coil unit having a plurality of coil sections and an emission face that transmits an alternating magnetic signal to the conducting object, a multiple-phase excitation circuit operatively coupled to the excitation coil unit to generate a traveling-wave alternating magnetic signal object, such that the alternating magnetic signal can be directionally controlled, and a magnetic detector that receives the alternating magnetic signal as modified by the conducting object, and generates a first electrical signal.

In some embodiments of the traveling-wave probe, a shielded preamplification circuit is provided within the probe. In some embodiments of the traveling-wave probe, the traveling-wave alternating magnetic signal is a linear traveling wave. In some embodiments of the traveling-wave probe, the traveling-wave alternating magnetic signal is a rotating traveling wave. In some such embodiments of the traveling-wave probe, the traveling-wave alternating magnetic signal is a cylindrical rotating traveling-wave electrical supply, for amplifying the first electrical signal.

Thus, some of the various embodiments of the present invention provide:

1. A super-sensitive eddy-current non-destructive evaluation (SSEC NDE) system that includes three fundamental parts:
   a) an SSEC NDE probe having an eddy-current (EC), remote-field eddy-current (RFEC) or travelling-magnetic-field or rotating-magnetic-field coils installed in a housing with shielding;
   b) a signal-conditioning circuit built in the probe; and
   c) an eddy-scope or instrument connected to the probe via a cable.
2. A SSEC NDE probe can be of any of the following configurations; see FIGS. 11A–11H. FIG. 11A shows an absolute probe 1100A with one excitation coil. FIG. 11B shows a differential probe 1100B with two excitation coils. FIG. 11C shows a reflection-drive absolute-pickup probe 1100C with one excitation and one pickup coil. FIG. 11D shows a reflection-drive differential-pickup 1100D, probe with one excitation and two pickup coils. FIG. 11E shows a rotating- or traveling-magnetic-field probe 1100E (absolute probe) with one multi-phase excitation unit and a pickup coil. FIG. 11F shows a rotating- or traveling-magnetic-field probe 1100F (differential probe) with one multi-phase excitation unit and two pickup coils. FIG. 11G shows a rotating-or traveling-magnetic-field probe 1100G (sensor-array probe) with one multi-phase excitation unit and a sensor array of absolute pickup coils and corresponding array-controlling system. FIG. 11H shows a rotating- or traveling-magnetic-field probe 1100H (sensor-array probe) with one multi-phase excitation unit and a sensor array of differential pickup coils and corresponding array-controlling system.
3. The housing of an SSEC NDE probe can optionally be made, or partially made of, highly conducting materials or a proper combination of highly conducting and ferromagnetic materials. Examples of such conducting materials include copper, aluminum, and steel. The housing acts as a shield for the coils and for the signal-conditioning circuit. The housing should cover all the sides of the coils except the side facing the specimen-under-inspection. In some embodiments, the coils in an SSEC NDE probe are all covered by a single shield, while in other embodiments, each is shielded individually.
4. The signal-conditioning unit includes at least a high-sensitivity and low-noise pre-amplifier. The input of the pre-amplifier are directly, using a shortest possible wiring route, connected to the leads of corresponding pickup coil(s) and share with the coil(s) the same grounding point(s). In some embodiments, the signal-conditioning unit is shielded separately by the housing for all its sides with no exception.
5. The differences of a SSEC NDE eddy-scope from a conventional eddy-scope include:
   a) Its probes may contain a properly shielded, extremely low noise signal conditioning unit and an SSEC NDE eddy-scope provides dc power lines to feed the signal-conditioning unit of the probe;
   b) compared to conventional eddy-scopes, an SSEC NDE eddy-scope has higher sensitivity and signal/noise ratio;
   c) while being capable of providing a single-phase ac current to the excitation coil(s) of an SSEC NDE probe, an SSEC NDE eddy-scope is also capable of supplying multi-phase ac currents to a rotating- or traveling-magnetic-field probe; and
   d) compared to conventional eddy-scopes, an SSEC NDE eddy-scope can be sensitive to flaws of different orientations.
   e) An SSEC NDE system is capable of accommodating variety of different sensors, such as MR, GMR, Hall elements, etc. In contrast, in a conventional eddy current system the only sensor can be used is coil. Coil sensor does not work well in lower frequencies, because the voltage induced in a coil is proportional to frequency. An SSEC NDE system is capable of working at very low frequencies, e.g. a few hertz, while remain its high sensitivity when an MR or GMR sensor is used, because the sensitivity of an MR or GMR is independent of frequency. The feature allows an SSEC NDE system to be used for detection of very deeply hidden corrosion and/or cracks.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method of transducing magnetic signals indicative of a flaw in a conducting object, comprising:
   shielding an excitation coil on substantially all sides except an emission face;
   transmitting an alternating magnetic signal to the conducting object from the shielded excitation coil, such that the alternating magnetic signal is modified by the conducting object;
   shielding a magnetic detector within a probe on substantially all sides except a reception face;
   receiving the alternating magnetic signal as modified by the conducting object into the shielded magnetic detector;
   converting the received alternating magnetic signal into a first electrical signal within the shielded magnetic detector;
   shielding a signal-conditioning circuit within the probe on substantially all sides;
   providing electrical power to the shielded signal-conditioning circuit within the probe;
   amplifying the first electrical signal with the signal-conditioning circuit to create a second electrical signal; and
   analyzing phase and amplitude components of the second electrical signal to provide an indication of the flaw.

2. The method of claim 1, wherein the shielding the excitation coil comprises providing a cup-shaped copper shield that surrounds a ring-shaped steel shield that in turn surrounds an excitation coil having a ferromagnetic core.

3. The method of claim 1, wherein the shielding the magnetic detector comprises providing a cup-shaped copper shield that surrounds a steel flux-bypass shield that in turn surrounds a receiver coil having a ferromagnetic core.

4. The method of claim 3, wherein the ferromagnetic core of the magnetic detector is E-shaped, and the receiver coil is mounted on a central prong of the E-shaped ferromagnetic core.

5. The method of claim 1, wherein the shielding the signal-conditioning circuit comprises providing an aluminum shield that surrounds the signal-conditioning circuit on substantially all sides.

6. The method of claim 1, wherein the transmitting the alternating magnetic signal comprises transmitting a rotating magnetic field.

7. The method of claim 6, wherein the receiving and the converting the received alternating magnetic signal provides a differential first electrical signal.

8. The method of claim 1, wherein the transmitting the alternating magnetic signal comprises transmitting a traveling magnetic field.

9. The method of claim 8, wherein the receiving and the converting the received alternating magnetic signal provides a differential first electrical signal.

10. The method of claim 1, wherein the receiving and the converting the received alternating magnetic signal provides a differential first electrical signal.

11. The method of claim 1, wherein the shielding the signal-conditioning circuit includes shielding between the signal conditioning circuit and the magnetic detector.

12. The method of claim 1, wherein the amplifying the first electrical signal to create a second electrical signal also includes low-pass filtering.

13. An eddy-current probe system for detecting a flaw in a conducting object, the probe comprising:
   an excitation coil unit shielded on substantially all sides except an emission face that transmits an alternating magnetic signal to the conducting object, such that the alternating magnetic signal is modified by the conducting object;
   a magnetic detector within the probe shielded on substantially all sides except a reception face, such that the alternating magnetic signal as modified by the conducting object is received into the shielded magnetic detector and converted into a first electrical signal;
   a signal-conditioning circuit within the probe, shielded on substantially all sides and provided with electrical power, which amplifies the first electrical signal to create a second electrical signal; and
   a signal channel that transmits the second electrical signal to an instrument for analyzing phase and amplitude components of the second electrical signal to provide an indication of the flaw.

14. The system of claim 13, further comprising:
   an eddy-scope, operatively coupled to the signal channel, that receives the transmitted second electrical signal, provides power the signal conditioning circuit and provides the analyzing phase and amplitude function for components of the second electrical signal, and that presents the indication of the flaw.

15. The system of claim 14, wherein the excitation coil unit comprises a coil having a ferromagnetic core, and is surrounded radially and axially by a cup-shaped first shield that surrounds substantially all sides except the emission face, wherein the ferromagnetic core of the excitation coil unit is surrounded radially by a ring-shaped second shield, located inside the cup of the first shield, wherein the first shield is substantially made of copper, and wherein the magnetic detector comprises an E-shaped ferromagnetic core having a coil mounted around a central prong of the E-shaped ferromagnetic core, a C-shaped steel flux bypass structure around and magnetically coupled to the E-shaped ferromagnetic core, and a copper shield surrounding C-shaped steel flux bypass structure and the E-shaped ferromagnetic core on substantially all sides except the reception face.

16. The system of claim 14, wherein the excitation coil unit comprises a multiple-phase coil configuration, and the eddy scope includes a multiple-phase excitation circuit that generates a plurality of phases of excitation signal to the excitation coil unit.

17. The system of claim 16, wherein the excitation coil unit comprises a traveling-wave multiple-phase coil configuration.

18. The system of claim 16, wherein the excitation coil unit comprises a rotating-wave multiple-phase coil configuration.

19. The system of claim 13, wherein the excitation coil unit comprises a coil having a ferromagnetic core, and is surrounded radially and axially by a cup-shaped first shield that surrounds substantially all sides except the emission face.

20. The system of claim 19, wherein the ferromagnetic core of the excitation coil unit is surrounded radially by a ring-shaped second shield, located inside the cup of the first shield.

21. The system of claim 19, wherein the first shield is substantially made of copper.

22. The system of claim 13, wherein the magnetic detector comprises a coil having a ferromagnetic core, and is surrounded radially and axially by a cup-shaped first shield that surrounds substantially all sides except the emission face.

23. The system of claim 22, wherein the first shield is substantially made of copper.

24. The system of claim 13, wherein the magnetic detector comprises an E-shaped ferromagnetic core having a coil mounted around a central prong of the E-shaped ferromagnetic core, a C-shaped steel flux bypass structure around and magnetically coupled to the E-shaped ferromagnetic core, and a copper shield surrounding C-shaped steel flux bypass structure and the E-shaped ferromagnetic core on substantially all sides except the reception face.

25. The system of claim 13, wherein the excitation coil unit comprises:
- an E-shaped core having at least a first, second, third, fourth, and fifth pole portion all connected to a common back section;
  - a first coil positioned around the first, second and third pole portions;
  - a second coil positioned around the second, third, and fourth pole portions; and
  - a third coil positioned around the third, fourth, and fifth portions;
  - wherein the first, second, and third coils are driven by three different phases of an alternating electrical signal to generate a traveling magnetic field.

26. The system of claim 13, wherein the excitation coil unit comprises:
- an E-shaped core having at least a first, second, third, fourth, and fifth pole portion all connected to a common circular back section;
  - a first coil positioned around the first, second and third pole portions;
  - a second coil positioned around the second, third, and fourth pole portions; and
  - a third coil positioned around the third, fourth, and fifth portions;
  - wherein the first, second, and third coils are driven by three different phases of an alternating electrical signal to generate a rotating magnetic field.

27. The system of claim 13, wherein the signal-conditioning circuit is further substantially shielded between the magnetic detector and the signal-conditioning circuit.

28. The system of claim 13, wherein the signal-conditioning circuit also includes a low-pass filter.

29. An eddy-current probe system for detecting a flaw in a conducting object, the probe comprising:
- an excitation coil unit having a plurality of excitation coils that transmit a traveling magnetic signal to the conducting object, such that the alternating magnetic signal is modified by the conducting object;
- an excitation driving circuit, operatively coupled to the excitation coil unit, that provides a multiple-phase electrical signal to the plurality of excitation coils to generate the traveling magnetic signal;
- a magnetic detector within the probe shielded on substantially all sides except a reception face, such that the traveling magnetic signal as modified by the conducting object is received into the shielded magnetic detector and converted into a first electrical signal;
- a signal-conditioning circuit within the probe, provided with electrical power, which amplifies the first electrical signal to create a second electrical signal; and
- a signal channel from the probe that transmits the second electrical signal to be analyzed to provide an indication of the flaw.

30. The system of claim 29, further comprising:
shielding substantially surrounding the signal-conditioning circuit, wherein the shielding shields substantially all electrical and magnetic signals from affecting the signal-conditioning circuit.

31. The system of claim 29, further comprising:
an instrument, operatively coupled the signal channel, that analyzes phase and amplitude components of the second electrical signal to be analyzed to provide the indication of the flaw.

32. The system of claim 29, wherein the traveling magnetic signal is a rotating magnetic signal.

33. The system of claim 29, wherein the traveling magnetic signal is a linear magnetic signal.

34. The system of claim 29, wherein the signal-conditioning circuit is separated from the magnetic detector by shielding.

* * * * *